(12) United States Patent
Puri et al.

(10) Patent No.: US 7,541,040 B2
(45) Date of Patent: Jun. 2, 2009

(54) CHIMERIC MOLECULE FOR THE TREATMENT OF TH2-LIKE CYTOKINE MEDIATED DISORDERS

(75) Inventors: Raj K. Puri, Potomac, MD (US); Cory M. Hogaboam, Ann Arbor, MI (US); Claudia Jakubzick, Ann Arbor, MI (US); Steven L. Kunkel, Ann Arbor, MI (US)

(73) Assignees: The United States of America as represented by the Department of Health and Human Serivces, Washington, DC (US); The Regents of the University of Michigan, Office of Technology Transfer, Ann Arbor, MI (US)

( * ) Notice: Subject to any disclaimer, the term of this patent is extended or adjusted under 35 U.S.C. 154(b) by 290 days.

(21) Appl. No.: 10/497,804

(22) PCT Filed: Feb. 28, 2002

(86) PCT No.: PCT/IB02/00616

§ 371 (c)(1),
(2), (4) Date: Feb. 10, 2005

(87) PCT Pub. No.: WO03/047632

PCT Pub. Date: Jun. 12, 2003

(65) Prior Publication Data

US 2005/0142105 A1    Jun. 30, 2005

Related U.S. Application Data

(60) Provisional application No. 60/337,179, filed on Dec. 4, 2001.

(51) Int. Cl.
*C12P 21/00* (2006.01)
*C07K 19/00* (2006.01)
*C07K 14/54* (2006.01)

(52) U.S. Cl. ............... 424/236.1; 424/192.1; 424/193.1; 424/195.11; 424/172.1; 424/198.1; 435/69.1; 435/69.52; 530/351

(58) Field of Classification Search ........................ None
See application file for complete search history.

(56) References Cited

U.S. PATENT DOCUMENTS 5,919,456 A * 7/1999 Puri et al. ................. 424/181.1
6,664,227 B1 * 12/2003 Wynn et al. ..................... 514/8

FOREIGN PATENT DOCUMENTS

EP       1270595 A       1/2003
WO       WO 96/29417 A1  9/1996
WO       WO 00/04926 A2  2/2000

OTHER PUBLICATIONS

"The Cytokine FactsBook", 2nd ed., K.A. Fitzgerald et al., Academic Press New York, 2001; pp. 105-109 and frontspiece.*
Blease, K., et al., "IL-13 fusion cytotoxin ameliorates chronic fungal-induced allergic airway disease in mice," 2001, *J. Immunol.*, vol. 167(11), pp. 6583-6592.
Blease, K., et al., "Therapeutic effect of IL-13 immunoneutralization during chronic experimental fungal asthma," 2001, *J. Immunol.*, vol. 166, pp. 5219-5224.
Blease, K., et al., "Stat6-deficient mice develop airway hyper-responsiveness and peribronchial fibrosis during chronic fungal asthma," 2002, *Am. J. Pathol.*, vol. 160(2), pp. 481-490.
Blümchen, K., et al., Interleukin-5: a novel target for asthma therapy, 2001, *Expert Opinion in Biological Therapy*, vol. 1(3), pp. 433-453. (Abstract provided).
Chomarat, P. and J. Banchereau, "Interleukin-4 and interleukin-13: their similarities and discrepancies," 1998, *Int. Rev. Immunol.*, vol. 17(1-4), pp. 1-52.
Corry, D.B., "IL-13 in allergy: home at last," 1999, *Curr. Opin. Immunol.*, 1999, vol. 11(6), pp. 610-614.
de Vries, J.E., "The role of IL-13 and its receptor in allergy and inflammatory responses," 1998, *J. Allergy Clin. Immunol.*, vol. 102(2), pp. 165-169.
Grünig, G., et al., "Requirement for IL-13 independently of IL-4 in experimental asthma," 1998, *Science*, vol. 282, pp. 2261-2263.
Husain, S.R. and P.K. Puri, "Interleukin-13 fusion cytotoxin as a potent targeted agent for AIDS-Kaposi's sarcoma xenograft," 2000, *Blood*, vol. 95, pp. 3506-3513.
Husain, S.R., et al., "Interleukin-13 receptor as a unique target for anti-glioblastoma therapy," 2001, *Int. J. Cancer*, vol. 92, pp. 168-175.
Kaminski, A., et al., "IL-2 and IL-4 specific and control antisense oligonucleotides can induce apoptosis of the malignant B-CLL cell," 2000, *Blood*, vol. 96(11, pt. 2), pp. 276b-277b. (Abstract provided).
Kawakami, K., et al., "Interleukin-13 receptor targeted cancer therapy in an immunodeficient animal model of human head and neck cancer," 2001, *Cancer Res.*, vol. 61, pp. 6194-6200.
Lamkhioued, B. and P.M. Renzi, "Inhibition of IL-4a and IL-13a' receptors by antisense phosphorothioate oligonucleotides suppress IL-4-induced human IgE production and Th2 differentiation," 2000, *J. Allergy Clin. Immunol.*, vol. 105(1-2), p. S179. (Abstract provided).
McKenzie, A.N., "Regulation of T helper type 2 cell immunity by interleukin-4 and interleukin-13," 2000, *Pharmacol. Ther.*, vol. 88(2), pp. 143-151.

(Continued)

*Primary Examiner*—Lorraine Spector
(74) *Attorney, Agent, or Firm*—Townsend and Townsend and Crew LLP

(57) ABSTRACT

The invention provides uses and methods for alleviating respiratory tract symptoms of allergy, asthma, and of viral, bacterial, fungal and parasitic infections by shifting inappropriate TH2 responses to TH1 responses by administering IL-13 receptor-targeted immunotoxins to the respiratory tract.

**18 Claims, 9 Draw

OTHER PUBLICATIONS

Oshima, Yasou and Raj. K. Puri, "Characterization of a powerful high affinity antagonist that inhibits biological activities of human interleukin-" 2001, *J. Biol. Chem.*, vol. 276, pp. 15185-15191.

Weltman, J.K. and A.S. Karim, "IL-5: biology and potential therapeutic applications," 2000, *Expert Opinion on Investigational Drugs*, vol. 9(3), pp. 491-496. (Abstract provided).

Wills-Karp, M., et al., "Interleukin-13: central mediator of allergic asthma," 1998, *Science*, vol. 282, pp. 2258-2261.

Zhu, Z., et al., Pulmonary expression of interleukin-13 causes inflammation, mucus hypersecretion, subepithelial fibrosis, physiologic abnormalities, and eotaxin production, 1999, *J. Clin. Invest.*, vol. 103, pp. 779-788.

* cited by examiner

FIG. 2. A.
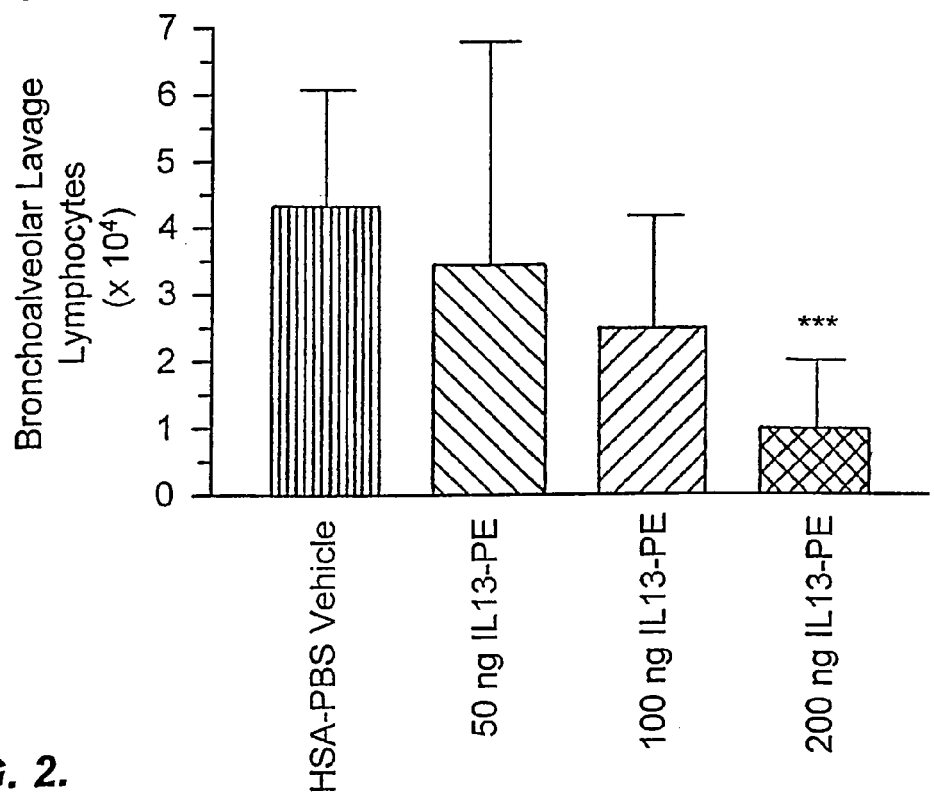
FIG. 2. B.
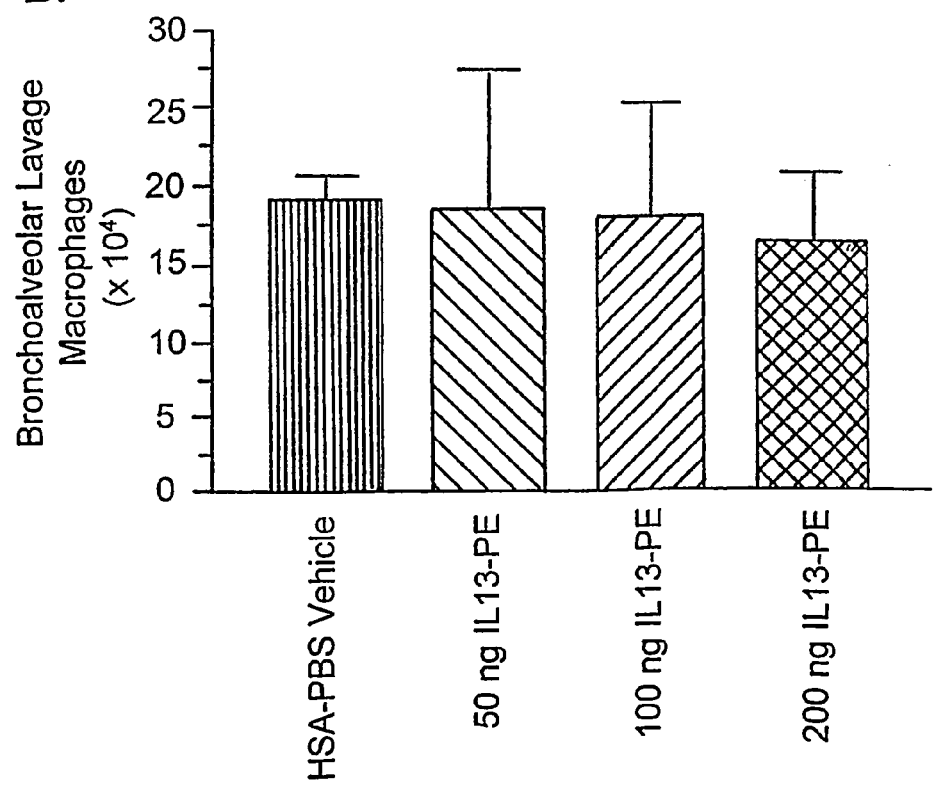

FIG. 5. A.
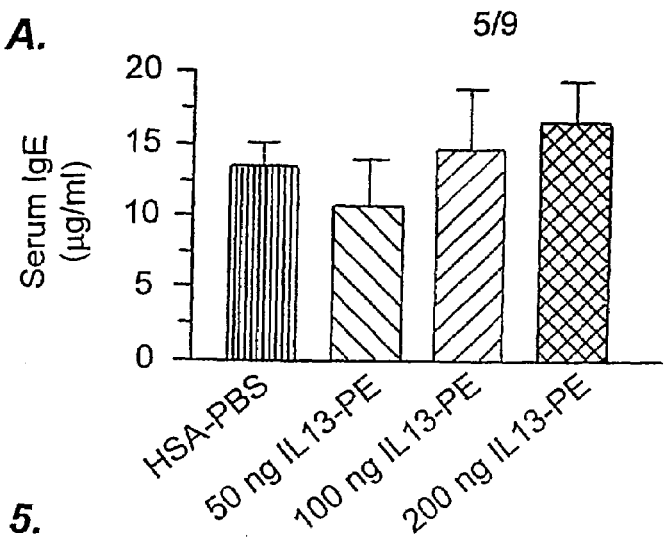
FIG. 5. B.
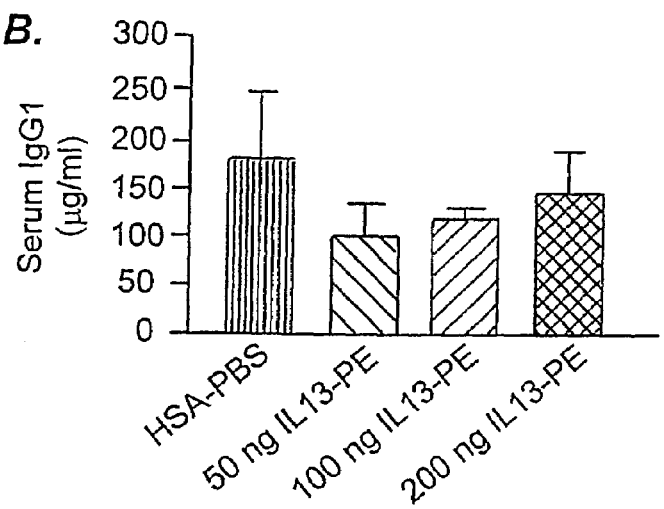
FIG. 5. C.
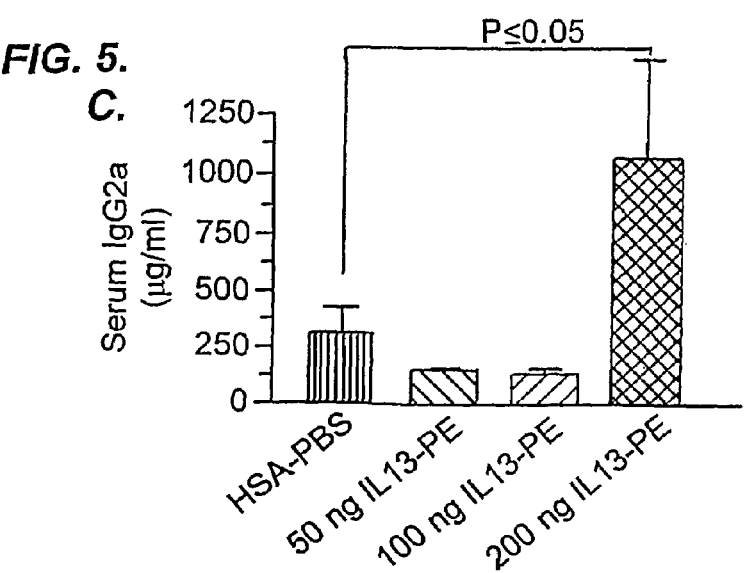

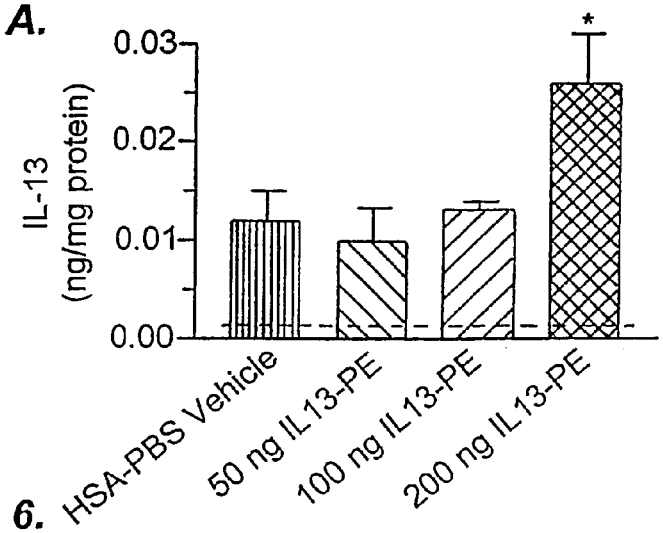
FIG. 6. A.
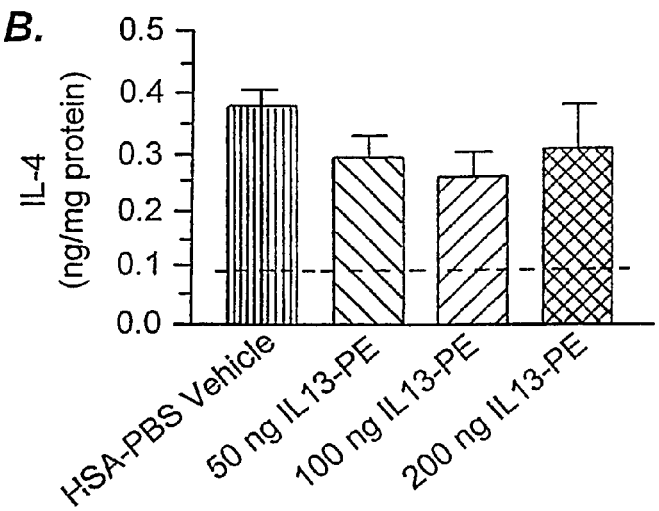
FIG. 6. B.
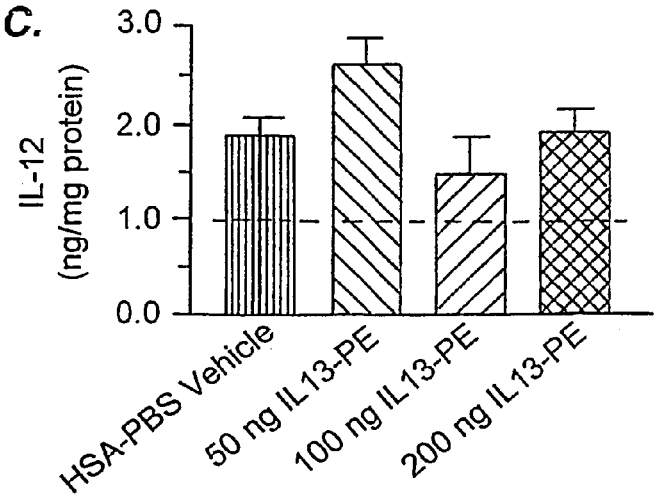
FIG. 6. C.

A.

B.

FIG. 9. A.
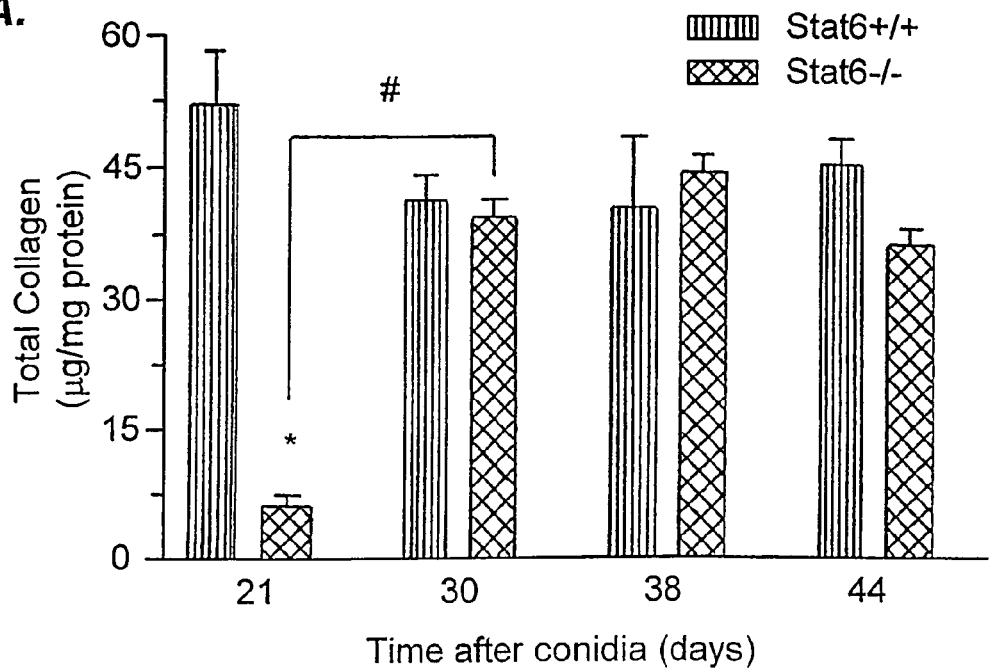
FIG. 9. B.
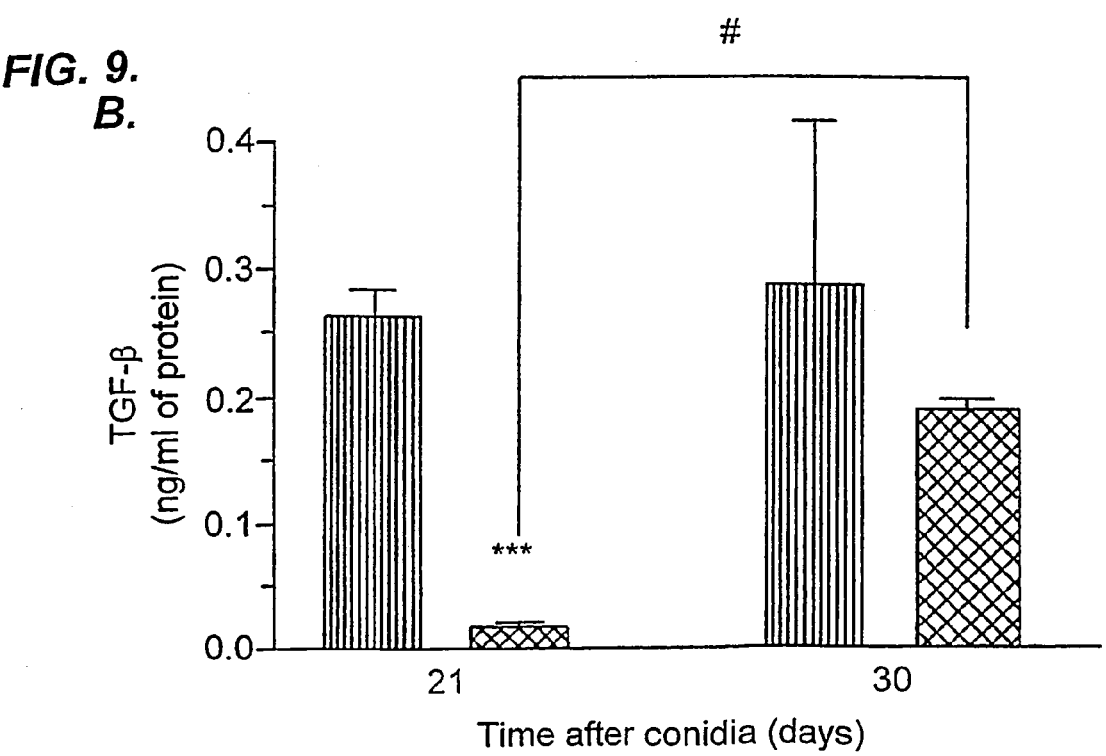

US 7,541,040 B2

CHIMERIC MOLECULE FOR THE TREATMENT OF TH2-LIKE CYTOKINE MEDIATED DISORDERS

CROSS-REFERENCES TO RELATED APPLICATIONS

This application claims the benefit of U.S. Provisional Application No. 60/337,179, filed Dec. 4, 2001, the contents of which are hereby incorporated for all purposes.

STATEMENT AS TO RIGHTS TO INVENTIONS MADE UNDER FEDERALLY SPONSORED RESEARCH AND DEVELOPMENT

This invention was made with government support under grant number HL073728, awarded by the U.S. National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK.

Not Applicable

FIELD OF THE INVENTION

This invention relates to the alleviation of symptoms of Th2-like cytokine mediated disorders, such as allergy, asthma, and to hyperinflammatory responses in the respiratory tract to infectious diseases and parasitic infections, including tuberculosis, schistosomiasis, leishmania, and filiarsis.

BACKGROUND OF THE INVENTION

Considerable clinical (Huang, S. K. et al., *J Immunol* 155: 2688 (1995); Devouassoux, G. et al., *J Allergy Clin Immunol* 104:811 (1999); Prieto, J., et al., *Respir Med* 94:806 (2000); KleinJan, A. et al., *J Allergy Clin Immunol* 103:441 (1999)) and experimental (Grunig, G. et al., *Science* 282:2261 (1998); Wills-Karp, M., *Science* 282:2258 (1998); Hogaboam, C. M. et al., *Aspergillus fumigatus. Am. J. Pathol.* 156:723 (2000)) evidence illustrates that asthma and atopy are characterized by the prominent expression of type 2 cytokines such as IL-4, IL-5 and IL-13, and a relative paucity of counterregulatory Th1 cytokines such as IFN-γ (Grunig, G. et al., *Science* 282: 2261 (1998); Wills-Karp, M., *Science* 282:2258 (1998); Hogaboam, C. M. et al., *Aspergillus fumigatus. Am. J. Pathol.* 156:723 (2000)). Consequently, this paradigm of cytokine imbalance during allergic airway disease has spawned numerous therapeutic strategies directed at the attenuation of the Th2 response and/or the enhancement of the Th1 response (Umetsu, D. T. et al. *Proc Soc Exp Biol Med* 215:11 (1997); Mavroleon, G. *Clin Exp Allergy* 28:917 (1998); Ferreira, M. B. et al., *J Investig Allergol Clin Immunol* 8:141 (1998)). Therapeutic strategies include regulation of the activation of signal transducers and activators of transcription and nuclear factor-κB; antibodies and soluble receptors directed against IgE, IL-4, and IL-5; as well as the unmethylated CpG oligodeoxynucleotides (Sur, S. et al., *J Immunol* 162:6284 (1999); Wong, W. S. et al., *Biochem Pharmacol* 59:1323 (2000)). Experimental studies have also shown that the systemic administration of anti-IL-4 (Corry, D. B. et al., *Mol Med* 4:344 (1998)), anti-IL-13 antibody (Grunig, G. et al., *Science* 282:2261 (1998); Blease, K. et al., *J. Immunol.* 166: 5219 (2001)) or the IL-13 inhibitor, soluble IL-13 receptorα2-Fc (Wills-Karp, M., *Science* 282:2258 (1998)), successfully abolishes the airway hyperresponsiveness and remodeling associated with allergic airway disease. One concern regarding all of these strategies, however, is that simply targeting a single transcription or cytokine pathway may not be sufficient to effectively eradicate asthmatic or allergic symptoms in all patients (Barnes, P. J. *Eur Respir J Suppl* 22:154s (1996)), particularly in light of recent experimental evidence that IL-4 and IL-13 appear to have redundant proinflammatory roles during aeroallergen challenge (Webb, D. C. et al., *J Immunol* 165:108 (2000)).

IL-4 shares receptor components and signaling pathways with IL-13, including the alpha chain of the IL-4 receptor and IL-13 receptorα1(IL-13Rα1) (Hilton, D. J. et al., *Proc Natl Acad Sci USA* 93:497 (1996); Schnyder, B. et al., *Blood* 87:4286 (1996); Miloux, B. et al., *FEBS Lett* 401:163 (1997)). However, IL-13 can also selectively bind to specific IL-13 receptors including IL-13Rα1 & IL-13Rα2 (Murata, T. et al., *Biochem Biophys Res Commun* 238:90 (1997); Donaldson, D. D. et al., *J Immunol* 161:2317 (1998)). Cells that respond to IL-13 are also excellent sources of the same cytokine. These cells include activated Th2 cells (Devouassoux G. et al., *J Allergy Clin Immunol* 104:811 (1999); Graber, P. et al., *Eur J Immunol* 28:4286 (1998)), B cells (Graber, P. et al., *Eur J Immunol* 28:4286 (1998)), mast cells (Toru, H. et al., *J Allergy Clin Immunol* 102:491 (1998); Lorentz, A. et al., *J Immunol* 164:43 (2000)), basophils (Devouassoux, G. et al., *J Allergy Clin Immunol* 104:811 (1999)) and alveolar macrophages (Prieto, J., et al., *Respir Med* 94:806 (2000); Hancock, A. et al., which the host processor has highest access priority to that memory section after completion of transfer of isochronous messages, but before completion of transfer of all messages.

These and other advantageous aspects of the bus system according to the invention will be described in more detail using the following figures.

FIG. 1 shows a bus system
FIG. 2 shows a sequence of time frames
FIG. 3 shows a transaction descriptor
FIG. 1 shows a USB system. The system contains a USB host 1, USB connections 17a,b and USB devices 18a,b. The USB host 1 contains a processor 10, a bus control unit 12, a common memory 14, all connected via an internal bus 16. The bus control unit 12 contains a host controller 120, a first memory 122a, a second memory 122b, a first access control unit 124a and a second access control unit 124b. The first and second memory 122a,b are coupled to the internal bus 16 via first and second access control unit 124a,b respectively, via a first access port of each of these access control units 124a,b.

The host controller 120 is connected to the USB connections 17a,b. Furthermore, the host controller 120 is connected to the internal bus 16, to a control input of the first and second access control unit 124a,b and to the first and second memory 122a,b via second ports of the first and second access control unit 124a,b. The host controller 120 has an interrupt line 15 coupled to processor 10.

In operation the system transfers messages to and from USB devices 18a,b via USB connections 17a,b. Data from the messages is produced or consumed by processor 10. In case data has to be sent to a USB device 18a,b processor 10 writes this data into one of the common memory 14 or first or second memory 122a,b (directly or using DMA). Host controller 120 reads this data from the relevant memory 14, 122a,b, encapsulates the data in a message and sends the message to an addressed device 18a,b via a USB connection 17a,b. Similarly, when a message has to be received from a USB device 18*a,b*, host controller 120 writes data from each message in one of the common memory 14 or the first and second memory 122*a,b*. In this case processor 10 subsequently reads this data from the relevant memory 14, 122*a,b* (directly or using DMA). *Am J Respir Cell Mol Biol* 18:60 (1998)). Given that the number of IL-4 and IL-13 producing cells are markedly increased during the course of airway inflammation associated with asthma and allergy (Devouassoux, G. et al., *J Allergy Clin Immunol* 104:811 (1999)), it is conceivable that adequate immunoneutralization of IL-4 or IL-13 may be difficult to maintain in these chronic diseases. A fusion protein comprised of IL-13 and a mutated form of *Pseudomonas* exotoxin (IL-13-PE38QQR or "IL13-PE") has been used to selectively target and eradicate solid tumor cells with endogenous (Husain, S. R. et al., *Blood* 95:3506 (2000)) and induced (Kawakami, K. et al., *Hum Gene Ther* 11:1829 (2000)) IL-13 receptor expression. Mice did not exhibit any adverse effects from the prolonged systemic in vivo administration of IL13-PE during parenteral tumor treatment (Husain, S. R. et al., *Blood* 95:3506 (2000)).

BRIEF SUMMARY OF THE INVENTION

This invention provides uses of a chimeric molecule comprising a toxic moiety and a targeting moiety that specifically binds to a cell surface receptor for IL-13, for the manufacture of a medicament for application to some or all of an airway of a mammal, to alleviate symptoms of a $T_H2$-type cytokine mediated disorder. The targeting moiety is typically selected from the group consisting of: an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor. In preferred embodiments, the anti-IL-13 receptor antibody is an scFv or dsFv. The toxic moiety can be selected from the group consisting of ricin A, abrin, ribotoxin, ribonuclease, saporin, calicheamycin, Diphtheria toxin or a cytotoxic fragment or mutant thereof, *Pseudomonas* exotoxin ("PE"), a cytotoxic portion thereof, a mutated *Pseudomonas* exotoxin which retains cytotoxicity, a cytotoxic portion thereof, and botulinum toxins A through F, pokeweed antiviral toxin or a cytotoxic fragment thereof, and bryodin 1 or a cytotoxic fragment thereof. In preferred embodiments, the toxic moiety is a *Pseudomonas* exotoxin or a cytotoxic fragment thereof or a mutated *Pseudomonas* exotoxin or a cytotoxic fragment thereof. In more preferred embodiments, the *Pseudomonas* exotoxin or mutated *Pseudomonas* exotoxin or cytotoxic fragment thereof is selected from the group consisting of PE35, PE38, PE38QQR, PE4E, and PE40. The $T_H2$-type cytokine mediated disorder can be, for example, an allergy, asthma, or a parasitic infection, or a viral, bacterial or fungal infection. In one group of embodiments, the allergy or asthma symptom to be alleviated is airway hyperresponsiveness. In another embodiment, the allergy or asthma symptom to be alleviated is excess mucus production. In some embodiments, the bacterial symptom to be alleviated is the formation of granulomas.

The invention further provides methods for alleviating a respiratory tract symptom of a $T_H2$-type cytokine mediated disorder in a mammal, said method comprising contacting an IL-13 receptor-expressing cell in some or all of a respiratory tract of said mammal with a chimeric molecule comprising a toxin moiety and a targeting moiety that specifically binds to an IL-13 receptor. The chimeric molecule can be administered intranasally, or through the mouth into the respiratory tract. The chimeric molecule can be in an aerosolized powder, or in an aerosolized liquid. The chimeric molecules can be administered into a bronchial tree or into a lung. The targeting moiety can be selected from the group consisting of: an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor. In preferred embodiments, the anti-IL-13 receptor antibody is an scFv or dsFv. The toxic moiety can be selected from the group consisting of ricin A, abrin, ribotoxin, ribonuclease, saporin, calicheamycin, Diphtheria toxin or a cytotoxic fragment or mutant thereof, *Pseudomonas* exotoxin ("PE"), a cytotoxic portion thereof, a mutated *Pseudomonas* exotoxin which retains cytotoxicity, a cytotoxic portion thereof, and botulinum toxins A through F, pokeweed antiviral toxin or a cytotoxic fragment thereof, and bryodin 1 or a cytotoxic fragment thereof. In preferred embodiments, the toxic moiety is a *Pseudomonas* exotoxin or a cytotoxic fragment thereof or a mutated *Pseudomonas* exotoxin or a cytotoxic fragment thereof. In particularly preferred embodiments, the *Pseudomonas* exotoxin or mutated *Pseudomonas* exotoxin or cytotoxic fragment thereof is selected from the group consisting of PE35, PE38, PE38QQR, PE4E, and PE40. In preferred embodiments, the $T_H2$-type cytokine mediated disorder alleviated is an allergy, asthma, or a viral, bacterial or parasitic infection. In some embodiments, the symptom of allergy or asthma alleviated is airway hyperresponsiveness. In other embodiments, the symptom of allergy or asthma alleviated is excess mucus production. In one set of embodiments, the bacterial infection is tuberculosis. The symptom of tuberculosis to be alleviated can be the formation of granulomas.

The invention further provides uses of a nucleic acid sequences encoding a chimeric molecule, said chimeric molecule comprising a toxic moiety and a targeting moiety that specifically binds to a cell surface receptor for IL-13, for the manufacture of a medicament for application to some or all of an airway of a mammal, to alleviate symptoms of a $T_H2$-type cytokine mediated disorder. The targeting moiety can be selected from the group consisting of: an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor. In preferred embodiments, the anti-IL-13 receptor antibody is an scFv or dsFv. The toxic moiety can be selected from the group consisting of ricin A, abrin, ribotoxin, ribonuclease, saporin, calicheamycin, Diphtheria toxin or a cytotoxic fragment or mutant thereof, *Pseudomonas* exotoxin ("PE"), a cytotoxic portion thereof, a mutated *Pseudomonas* exotoxin which retains cytotoxicity, a cytotoxic portion thereof, and botulinum toxins A through F, pokeweed antiviral toxin or a cytotoxic fragment thereof, and bryodin 1 or a cytotoxic fragment thereof. In preferred embodiments, the toxic moiety is a *Pseudomonas* exotoxin or a cytotoxic fragment thereof or a mutated *Pseudomonas* exotoxin or a cytotoxic fragment thereof. In particularly preferred embodiments, the *Pseudomonas* exotoxin or mutated *Pseudomonas* exotoxin or cytotoxic fragment thereof is selected from the group consisting of PE35, PE38, PE38QQR, PE4E, and PE40. In preferred embodiments, the $T_H2$-type cytokine mediated disorder alleviated is an allergy, asthma, or a viral, bacterial or parasitic infection. In some embodiments, the symptom of allergy or asthma alleviated is airway hyperresponsiveness.

The invention further provides methods for alleviating an airway symptom of a $T_H2$-type cytokine mediated disorder in a mammal, the methods comprising contacting a cell in a respiratory tract of the mammal with a nucleic acid encoding a chimeric molecule comprising a toxin moiety and a targeting moiety that specifically binds to an IL-13 receptor, or a vector comprising said nucleic acid, under conditions permitting said chimeric molecule to be expressed, and contacting an IL-13 receptor expressing cell of the respiratory tract with the expressed chimeric molecule. The nucleic acid or said vector can be administered intranasally or into a bronchial tree or lung and can be in an aerosolized powder or an aerosolized liquid. The targeting moiety can be selected from the group consisting of: an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor. The anti-IL-13 receptor antibody can be an scFv or dsFv. The toxic moiety can be selected from the group consisting of ricin A, abrin, ribotoxin, ribonuclease, saporin, calicheamycin, Diphtheria toxin or a cytotoxic fragment or mutant thereof, *Pseudomonas* exotoxin ("PE"), a cytotoxic portion thereof, a mutated *Pseudomonas* exotoxin which retains cytotoxicity, a cytotoxic portion thereof, and botulinum toxins A through F, pokeweed antiviral toxin or a cytotoxic fragment thereof, and bryodin 1 or a cytotoxic fragment thereof. In preferred embodiments, the $T_H2$-type cytokine mediated disorder alleviated is an allergy, asthma, or a viral, bacterial or parasitic infection. In some embodiments, the symptom of allergy or asthma alleviated is airway hyperresponsiveness.

In yet a further set of embodiments, the invention provides a use of a nucleic acid sequence for the manufacture of a medicament for application to some or all of an airway of a mammal to alleviate symptoms of a $T_H2$-type cytokine mediated disorder, which nucleic acid sequence hybridizes under stringent conditions to a sequence encoding a molecule selected from IL-13 and IL-13 receptor. The symptom of a $T_H2$-type cytokine mediated disorder alleviated can be of allergy or of asthma, or of a viral, bacterial, fungal or parasitic infection. The symptom to be alleviated can be airway hyperresponsiveness.

The invention further provides a method for alleviating a respiratory tract symptom of a $T_H2$-type cytokine mediated disorder in a mammal. The method comprises contacting an IL-13 expressing cell in an airway of said mammal with a first nucleic acid that hybridizes under stringent conditions with a second nucleic acid encoding IL-13 wherein hybridization of said first and said second nucleic acids inhibits expression of said IL-13.

The invention further provides a method for alleviating a respiratory tract of a $T_H2$-type cytokine mediated disorder in a mammal, said method comprising contacting an IL-13-receptor expressing cell in a respiratory tract of said mammal with a first nucleic acid that hybridizes under stringent conditions with a second nucleic acid encoding IL-13 receptor, wherein hybridization of said first and said second nucleic acids inhibits expression of said IL-13 receptor. The symptom of a $T_H2$-type cytokine mediated disorder alleviated can be of allergy or of asthma.

BRIEF DESCRIPTION OF THE DRAWINGS

FIG. 2: Leukocyte counts in bronchoalveolar lavage (BAL) samples at day 28 after *A. fumigatus* conidia challenge in the control (HSA-PBS vehicle or diluent) and IL-13-PE38QQR (IL13-PE) treatment groups. *A. fumigatus*-sensitized mice received diluent or 50, 100 or 200 ng of IL13-PE every other day starting at day 14 to concluding at day 28 after a conidia challenge (see Materials and Methods). BAL cells were dispersed onto microscope slides. FIG. 2A: T lymphocytes. FIG. 2B: macrophages. Both figures: cells were differentially stained with Wright-Giesma stain. A minimum of 15 high-powered-fields or 300 cells was examined in each cytospin. A total of 1×10⁶ BAL cells-were cytospun onto each slide to compensate for differences in cell retrieval from each mouse. Values are expressed as mean±SE. ***P≦0.001 compared with levels measured in the control treatment group at day 28 after the conidia challenge.

FIG. 5: Panel 5A: Total serum IgE levels in *A. fumigatus*-sensitized rice at day, 28 after *A. fumigatus* conidia challenge in the control (HSA-PBS vehicle) and IL-13-PE38QQR (IL13-PE) treatment groups. Panel 5B: Total serum IgG1 levels in *A. fumigatus*-sensitized mice at day 28 after *A. fumigatus* conidia challenge in the control (HSA-PBS vehicle) and IL-13-PE38QQR (IL13-PE) treatment groups. Panel 5C: Total serum IgG2a levels in *A. fumigatus*-sensitized mice at day 28 after *A. fumigatus* conidia challenge in the control (HSA-PBS vehicle) and IL-13-PE38QQR (IL13-PE) treatment groups. *A. fumigatus*-sensitized mice received diluent or 50, 100 or 200 ng of IL13-PE every other day starting at day 14 and concluding at day 28 after a conidia challenge. Total IgE, IgG1 and IgG2a were measured using specific ELISAs as described in the Examples. No differences in serum IgE levels were detected between the two groups at any point prior to or after the conidia challenge (see panel 5A). Data are expressed as mean±SE; n=5-10 mice/group. Statistical differences between the control (HSA-PBS vehicle or diluent) and 200-ng IL13-PE treatment groups at day 28 after conidia are indicated in Panels 5B and 5C.

FIG. 6: Levels of cytokines IL-13 (FIG. 6A), IL-4 (FIG. 6B) and IL-12 (FIG. 6C) levels in whole lung homogenates at day 28 after *A. fumigatus* conidia challenge in the control (HSA-PBS vehicle or diluent) and IL-13-PE38QQR (IL13-PE) treatment. groups. *A. fumigatus*-sensitized mice received diluent or 50, 100 or 200 ng of IL13-PE every other day starting at day 14 and concluding at day 28 after a conidia challenge. Immunoreactive levels of IL-13, IL-4 and IL-12 were measured using a specific ELISA. The dashed lines indicate cytokine levels in whole lung samples from *A. fumigatus*-sensitized mice prior to the conidia challenge. Values are expressed as mean±SE; n=5-10 mice/group. *$P \leq 0.05$ compared with levels measured in the control group at day 28 after the conidia challenge.

FIG. 7A. IFN-γ levels in whole lung homogenates. FIG. 7B. IFN-γ levels in bronchoalveolar lavage samples. Both Figures: levels measured at day 28 after *A. fumigatus* conidia challenge in the control (HSA-PBS vehicle or diluent) and IL-13-PE38QQR (IL13-PE) treatment groups. *A. fumigatus*-sensitized mice received diluent or 50, 100, or 200 ng of IL13-PE every other day starting at day 14 and concluding at day 28 after a conidia challenge. Immunoreactive levels of IFN-γ were measured using a specific ELISA. The dashed line indicates IFN-γ levels in whole lung samples from *A. fumigatus*-sensitized mice prior to the conidia challenge. No IFN-γ was detected in BAL samples from *A. fumigatus*-sensitized mice prior to the conidia challenge. Values are expressed as mean±SE; n=5-10 mice/group. *$P \leq 0.05$ compared with levels measured in the control group at day 28 after the conidia challenge.

FIG. 9: FIG. 9A: Total soluble collagen levels. FIG. 9B: Whole lung transforming growth factor-β (TGF-β). Both Figures: Levels in *A. fumigatus*-sensitized Stat6-wildtype (+/+) and Stat6-deficient (−/−) mice at various times after an *A. fumigatus* conidia challenge. Whole lung levels of collagen and TGF-β were measured in both groups as described in the Examples. Values are expressed as mean±SE; n=5/group/time point. *, P<0.05, ***, P<0.001 demonstrate significant differences between Stat6+/+ and Stat6−/− mice at the same time after conidia challenge. #, P<0.05 demonstrates a significant difference in total collagen and TGF-β levels in Stat6−/− mice at days 21 and 30 after conidia.

DETAILED DESCRIPTION

Introduction

Figure 1:
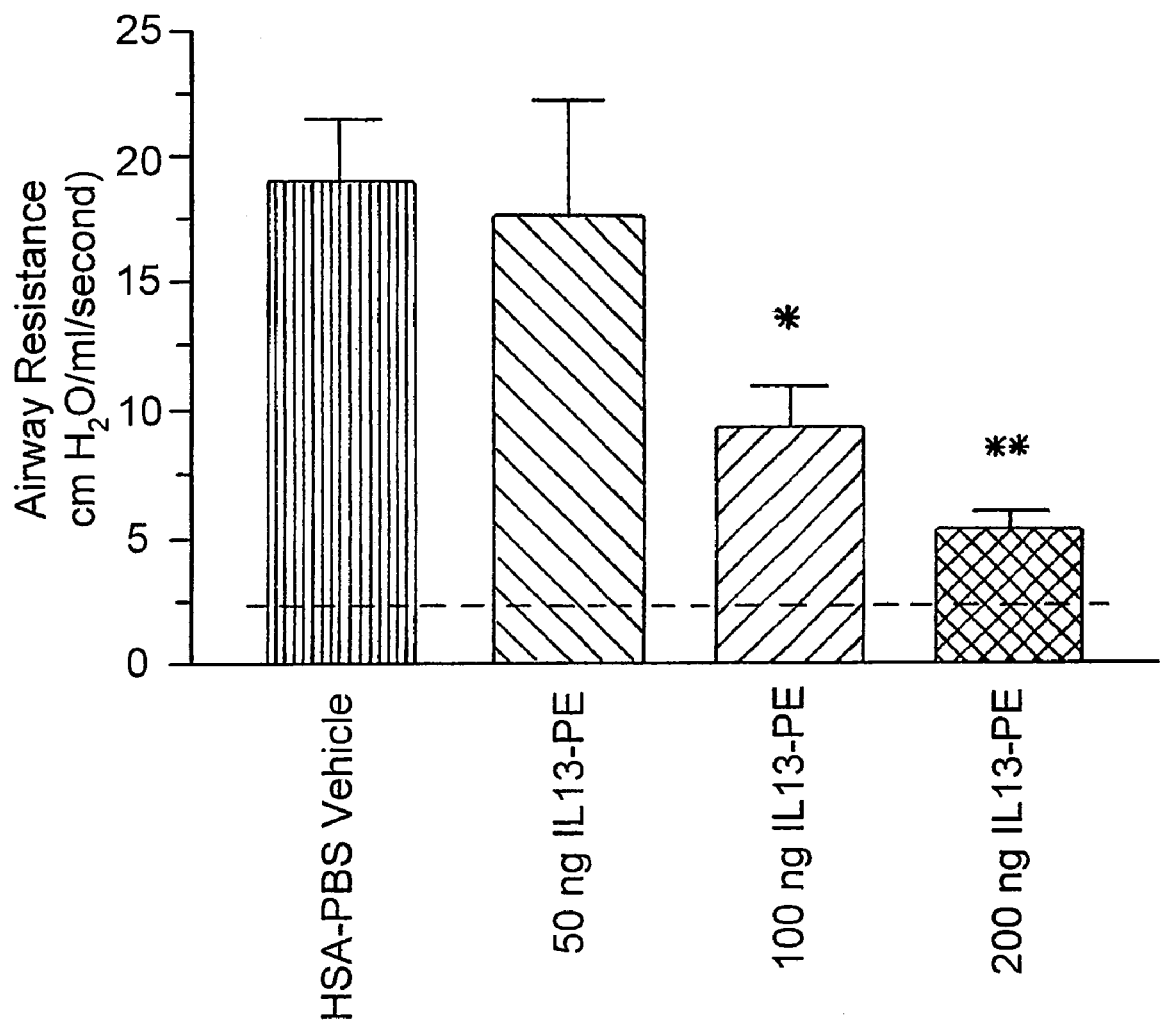
FIG. 1: Airway hyperresponsiveness at day 28 after *A. fumigatus* conidia challenge in the control (HSA-PBS vehicle or diluent) and IL-13-PE38QQR (IL 13-PE) treatment groups. *A. fumigatus*-sensitized mice received diluent or 50, 100 or 200 ng of IL13-PE every other day starting at day 14 and concluding at day 28 after a conidia challenge (see Materials and Methods). The baseline airway resistance in all groups was similar prior to the methacholine provocation and the mean baseline resistance for all four groups is indicated by the dashed line (2.5±0.3 cm H₂O/ml/sec). Peak increases in airway resistance after the intravenous injection of 125 μg/ml methacholine are shown. Values are expressed as mean±SE; n=5-10 mice/group. *P≦0.05, **P<0.01 compared with levels measured in the control treatment group at day 28 after the conidia challenge.

Surprisingly, it has now been discovered that symptoms of T$_H$2 like cytokine mediated disorders can be alleviated by administering to the lungs, to the bronchi, to the nasal passages and to the connecting passages, immunotoxins comprising a targeting moiety which binds to the IL-13 receptor, and a cytotoxin. (For ease of reference, the nasal passages, trachea, bronchi, lungs and other portions of the respiratory system will be referred to collectively herein as the "airway" or the "respiratory tract" unless another meaning is required or intended in context.)

As discussed in the Background, above, IL-4 and IL-13 producing cells are markedly increased during the course of airway inflammation associated with asthma and allergy (Devouassoux, G. et al., *J Allergy Clin Immunol* 104:811 (1999)). The distribution and number of cells expressing the IL-13 receptor ("IL-13R") in the airway are, however, not known. It therefore was not known, and could not be predicted, whether contacting cells in the airway of a mammal with an immunotoxin targeted to the IL-13 receptor ("IL-13R") would result in alleviating symptoms of asthma or of allergy.

Surprisingly, it has now been discovered that IL-13R-targeted immunotoxins can be administered to the airway of a mammal without obvious ill effect, but with alleviation of symptoms of allergy and of asthma. Administration of an exemplar immunotoxin to mice in a chronic fungal model widely accepted in the art as correlated to human asthma not only resulted in the alleviation of symptoms such as chronic airway hyperactivity, goblet cell hyperplasia, and peribronchial fibrosis, but also resulted in the avoidance of recurrence of the symptoms during the remaining time course of the study. Administration of the exemplar immunotoxin markedly reduced or abolished the whole lung expression of IL-4 receptor a (IL-4Rα) and IL-13Rα1 during *Aspergillus*-induced allergic airway disease, demonstrating that the immunotoxin eliminated cells that are responsive to IL-4 and IL-13. In a preferred embodiment, the allergy is allergic rhinitis. In view of these results, administration of IL-13R-targeted immunotoxins can also be used to decrease other allergic or asthmatic airway diseases, including those based on airborne particulates, such as diesel exhaust.

These results, set forth in the Examples herein, related specifically to symptoms of asthma and allergy. Surprisingly, it has further been discovered that eliminating IL-13 responsive cells in the respiratory tract can block inflammatory and other responses in the respiratory tract in $T_H2$-like cytokine mediated disorders. These disorders include $T_H2$-type response to infectious diseases and to viral, bacterial, fungal, and parasitic diseases. Without wishing to be bound by theory, it is believed that in some $T_H2$-like cytokine mediated disorders in which IL-13 may not be the only $T_H2$ cytokine involved in the disorder, it may function as part of a cascade and that eliminating IL-13 responsive cells in the airway may block the cascade from proceeding.

Previous studies have shown that the granulomatous response elicited by *Schistosoma mansoni* via infection and after intravenous (i.v.) injection of live *S. mansoni* eggs is dependent on the Th2-dominant cellular events mediated by IL-4 and IL-13. Studies conducted in the course of the present invention revealed that when given after the i.v. injection of live *S. mansoni* eggs, administration of an exemplar IL-13R-targeted immunotoxin significantly. arrested the development of the Th2-mediated pulmonary granulomatous response. Interestingly, the therapeutic effect of the immunotoxin appeared to be mediated through the inhibition of IL-4, IL-13, tumor necrosis factor-α (TNF-α), and monocyte chemoattractant protein-1 (MCP-1/CCL2) generation and a concomitant dramatic increase in IL-13 decoy-receptor (i.e. IL-13Rα2) expression.

In light of these results, administration of IL-13R-targeted immunotoxins can be used to shift the body's immune response in the respiratory tract to infectious and parasitic diseases from an inappropriate $T_H2$ response to a $T_H1$ response, which is more useful in combating these diseases. For example, in fungal infections, such as candida, thrush, and *Aspergillus*, immune responses with a $T_H2$ cytokine profile permit the fungus to proliferate uncontrollably. In contrast, mounting a $T_H1$ response helps bring the infection under control. Administration of IL-13R-targeted immunotoxins permits modulating the immune response to a $T_H1$ response, permitting more effective control of the infection. Similarly, in biral and bacterial infections of the respiratory tract, administration of IL-13R-targeted immunotoxins can be beneficial in shifting the immune response to a $T_H1$ response to help clear or to control the infection. The invention is particularly useful in respiratory tract infections by *Pseudomonas, Klebsiella*, and *Mycobacteria*.

In a preferred embodiment, the infectious disease is tuberculosis. Type 2 cytokines play a major role in the overaggressive collagen matrix deposition by which the body forms granulomas in an attempt to wall off the *Mycobacterium tuberculosis* ("Mtb"). Administration. of L-13R-targeted immunotoxins to the lungs eliminates or reduces the population of IL-13R-expressing cells. In light of the results in reducing granuloma formation in the *S. mansoni* model, it is expected that mammals infected with Mtb in which IL-13R-targeted immunotoxins are administered in the airway will undergo reduced formation of granulomas in the lungs. While this effect is beneficial in itself, it is further expected. that the reduction in granuloma formation around the Mtb will increase the ability of antibiotics and other conventional treatments to reach the Mtb, thereby increasing the effectiveness of those agents in inhibiting growth of the Mtb.

In addition to tuberculosis and schistosomiasis, the uses and methods of the invention are expected to be useful in reducing granulomas and other symptoms (including inflammatory and other symptoms in the lungs or other portions of the airway) in other infectious and parasitic diseases in which $T_H2$ cytokine responses play a. major role, including filariasis and Leishmania. With respect to Leishmania, it is noted that the parasite is known to induce a Type 2 response, thereby inhibiting the development of a Type 1 response. A Type 1 response, however, would be more effective in combating the infection. The use of IL-13R-targeted immunotoxins is expected to reduce the $T_H2$ response, permit the consequent upregulation of a Type 1 response, and result in a more effective control of the parasite by the patient's immune system.

Persons of skill will recognize that the role of IL-13 in mediating responses to allergy (including allergic rhinitis), asthma, and responses to infectious diseases and parasitic infections also implicates to some extent IL-4. Like many cytokines, IL-4 and IL-13 comprise some polypeptide chains that are shared, and one or more chains not shared with other another cytokine (so-called "private chains"). In the case of IL-4 and IL-13, IL-4 directly binds the IL-4 receptor alpha (IL-4Rα) and IL-13 specifically binds the IL-13Rα1 chain, but IL-4Rα and IL-13Rα1 can form a functional receptor complex that binds both ligands. IL-13 also binds with 100-fold higher affinity for IL-13Rα2 than IL-13Rα1. The IL-13Rα2 chain is a "private chain" not shared with IL-4R. The IL-13Rα2 chain does not appear to have a cytoplasmic tail thought to be necessary for signaling and is thought to function to absorb excess IL-13 or otherwise to modulate IL-13 signaling. The chain is, however, internalized into the cell, and can serve as an immunotoxin target. Since cells which express the IL-13Rα2 chain typically also express functional IL-13R, eliminating IL-13Rα2 chain cells is useful in the uses and methods of the invention.

Some of the immunotoxins contemplated for use in the uses and methods of the present invention can be expected to bind to cells expressing the IL-4R or the IL-13Rα2 chain. This is particularly true of immunotoxins in which IL-13 or a mutated IL-13 is used as a targeting moiety. The studies performed in the course of the present invention, however, indicate that the loss of any IL-4R- or IL-13Rα2 chain-expressing cells which may be killed in the course of the administration of the immunotoxins is not harmful and does not impair the effect of the administration on reducing the symptoms of the disorder for which the agent is being administered. Indeed, the loss of IL-4R-expressing cells may augment the reduction of symptoms, particularly with respect to pulmonary features which are partly dependent on IL-4 signaling. If desired, however, the effect on IL-4R-expressing cells can be eliminated by use of an immunotoxin that does not bind to chains common to both the IL-13R and the IL-4R. For example, the practitioner can use as a targeting moiety monoclonal antibodies that bind to the IL-13R but not the IL-4R. Such antibodies are conveniently generated by generating antibodies to IL-13R by conventional means, and then running the antibodies on a column containing immobilized IL-4. Any antibodies eluting through the column will serve as targeting moieties that bind IL-13R but not IL-4R. For example, one can use an antibody to the IL-13Rα2 chain, which is a chain not shared with IL-4R.

It should be noted that these diseases and disorders may initiate responses or have other pathologic effects that are not related to the $T_H2$-like cytokine response; these symptoms and aspects may not be alleviated by the methods and uses discussed herein. In preferred embodiments, the symptoms and aspects of allergy, asthma, and $T_H2$-like cytokine disorders alleviated by the uses and methods discussed herein are in or relate directly to the airway, such as inflammation, deposition of collagen matrix, and airway hyperresponsiveness.

Asthma and allergies are classified as forms of localized anaphylaxis (anaphylaxis limited to a particular tissue or organ). Some persons are at risk of anaphylactic reaction to environmental stimuli such as bee stings or exposure to certain foods. Because of the effect of the administration of IL-13R-targeted immunotoxins on reducing allergic responses in the airway, it is expected that contacting the airways of persons susceptible to anaphylaxis will serve as a prophylactic protection to reduce or alleviate the severity of the anaphylactic reaction. The IL-13R-targeted immunotoxins or nucleic acids or vectors encoding the immunotoxins administered for this purpose can be administered in the same form and manner as those administered for other allergic conditions.

Definitions

Unless defined otherwise, all technical and scientific terms used herein have the meaning commonly understood by a person skilled in the art to which this invention belongs. The following references provide a general definition of many of the terms used in this invention: Singleton et al, DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms have the meanings ascribed to them unless specified otherwise.

"IL-13" is a pleiotropic cytokine that is recognized to share many of the properties of IL-4. IL-13 has approximately 30% sequence identity with IL-4 and exhibits IL-4-like activities on monocytes/macrophages and human B cells (Minty et al., Nature, 362: 248 (1993), McKenzie et al. Proc. Natl. Acad. Sci. USA, 90: 3735 (1987)). In particular, IL-13 appears to be a potent regulator of inflammatory and immune responses. Like IL-4, IL-13 can up-regulate the monocyte/macrophage expression of CD23 and MHC class I and class II antigens, down-regulate the expression of Fc.gamma., and inhibit antibody-dependent cytotoxicity. IL-13 can also inhibit nitric oxide production as well as the expression of pro-inflammatory cytokines (e.g. IL-1, IL-6, IL-8, IL-10 and IL-12) and chemokines (MIP-1, MCP), but enhance the production of IL-1ra (e.g., Minty supra.; Mckenzie et al., supra.; Zurawski et al. Immunol. Today, 15: 19 (1994); de Wall Malefyt et al. J. Immunol., 150:180A (1993); de Wall Malefyt et al. J. Immunol., 151: 6370 (1993); Doherty et al. J. Immunol., 151: 7151 (1993); and Minty et al. Eur. cytokine Netw., 4: 99 (1993)). Recombinant IL-13 is commercially available from a number of sources (see, e.g. R & D Systems, Minneapolis, Minn., USA, and Sanofi Bio-Industries, Inc., Tervose, Pa., USA). Alternatively, a gene or a cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al. (1993) supra, and McKenzie (1987), supra).

The term "cpIL-13" is used to designate a circularly permuted (cp) IL-13. Circular permutation is functionally equivalent to taking a straight-chain molecule, fusing the ends (directly or through a linker) to form a circular molecule, and then cutting the circular molecule at a different location to form a new straight chain molecule with different termini.

The IL-13 receptor ("IL-13R") is a cell surface receptor that binds IL-13 and mediates a variety of physiological responses in various cell types. IL-13R is a heterodimeric molecule composed of two polypeptide "chains" of approximately 65 kD. The first chain is now known as the IL-13Rα1 chain, and was previously termed the IL-13Rα chain, or the IL-13α' chain. An isoform was later cloned and was called IL-13Rα. To clarify references to the two forms of the chain, this isoform was then renamed as the IL-13α2 chain. As used herein, "IL-13α2" refers to this isoform. The amino acid sequence of the IL-13Rα2 chain and the native mRNA sequence encoding it were reported by Caput, D. et al., *J. Biol. Chem.* 271, 16921-16926 (1996); both sequences were deposited in GenBank under accession number X95302.

The term "IL-13 mediated disorder" refers to a condition which is due to, or is exacerbated by, the binding of IL-13 to its receptor. In this regard, it is noted that some conditions may be initiated by the binding of IL-13 to its receptor, while in other conditions, the binding of IL-13 to its receptor is part of a cascade and results in an amplification of an organism's response to an initial activating event. The term "IL-13 mediated disorder" specifically includes asthma, allergic rhinitis, and inflammatory responses to infectious and parasitic diseases, specifically including tuberculosis, schistosomiasis, Leishmania, and filariasis.

The term "$T_H 2$-like cytokine mediated disorder" refers to any of a number of conditions known in the art as being due to or exacerbated by a $T_H 2$-like cytokine response. Persons of skill are aware that $T_H$ cells respond to activation by secretion of cytokines that fall into one of two groups: the $T_H 1$ response, in which the $T_H$ cells secrete cytokines that support inflammation and activate T cells and macrophages, or the $T_H 2$ response, in which the $T_H$ cells secrete cytokines that activate B cells and an antibody, rather than a cellular response. See, e.g., Goldsby et al. (eds) *Kuby Immunology*, W. H. Freeman and Co., New York ($4^{th}$ Ed. 2000). The $T_H 1$ and $T_H 2$ responses are considered antagonists of each other. Id. In recent years, it became appreciated that cells other than $T_H$ cells could secrete cytokines that activate these responses. Accordingly, the terms "Th1 cytokine like response" and "Th2 cytokine like response" has been used to refer to cytokine expression patterns characteristic of $T_H 1$ or of $T_H 2$ type responses. For example, cells that secrete cytokines that result in increases of $T_H 2$ cytokines such as IL-5 and IL-10 and in decreases of Th1 cytokines such as IL-12 are considered to cause a $T_H 2$ like cytokine response, see, e.g., Jutel et al., Cline Exp Allergy, 25:1108-17 (1995), while antigens that preferentially activate Th1 cytokine responses are considered to cause Th1 like cytokine responses. See, e.g., HayGlass et al., Adv Exp Med Biol 409:309-16 (1996). The term "Th2-like cytokine mediated disorder" specifically includes asthma, allergies (including allergic responses to ragweed, animal danders, and pollens), and inflammatory or other responses of the respiratory tract to infectious and parasitic diseases, including tuberculosis, schistosomiasis, Leishmania, filariasis, fungal infections such as candida, *Aspergillus, Cryptococcus neoformans*, and thrush, bacterial infections such *Pseudomonas* and *Klebsiella* infections of the lungs, and viral infections of the lungs such as respiratory syncitial virus (RSV), or of cells that traffic to the lung. It should be noted that these diseases and disorders may initiate responses or have other pathologic effects that are not related to the $T_H 2$-like cytokine response; these symptoms and aspects may not be alleviated by the methods and uses discussed herein. In preferred embodiments, the symptoms and aspects of allergy, asthma, and $T_H 2$-like cytokine disorders alleviated by the uses and methods discussed herein are in or relate to the airway. IL-13 mediated disorders are one category of Th2-like cytokine mediated disorders.

Unless otherwise required by context, as used herein, the term "airway" denotes the nasal passages, trachea, bronchial tree, lungs, and connecting passages.

"Asthma" is a chronic lung disease which, according to the National Institute on Allergy and Infectious Diseases ("NIAID"), affects an estimated 17 million Americans. In many people, asthma is considered as an allergic response in which IgE production causes a release of chemicals from mast cells, resulting in inflammation and constriction of airways in the lungs, causing coughing, wheezing, and difficulty breathing. NIAID states that nearly 500,000 Americans are hospitalized and more than 5,000 die from asthma annually. As used herein, "asthma" comprehends asthma-like inflammatory airway diseases caused by exposure to environmental pollutants or particulates, such as diesel exhaust.

"Allergy," is defined as a hypersensitivity reaction that can include hay fever, asthma, serum sickness and systemic anaphylaxis.

"Bronchial tree" refers to the network of bronchial tubes leading to the lung.

"Antibody" refers to a polypeptide ligand comprising at least a light chain or heavy chain immunoglobulin variable region which specifically recognizes and binds an epitope (e.g., an antigen). This includes intact immunoglobulins and the variants and portions of them well known in the art such as, Fab' fragments, F(ab)'$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker. The term also includes genetically engineered forms such as chimeric antibodies (e.g., humanized murine antibodies), heteroconjugate antibodies (e.g., bispecific antibodies). See also, Pierce Catalog and Handbook, 1994-1995 (Pierce Chemical Co., Rockford, Ill.); Kuby, J., *Immunology*, $3^{rd}$. Ed., W.H. Freeman & Co., New York (1997).

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

"Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols* in METHODS IN MOLECULAR BIOLOGY, Vol. 66, Glenn E. Morris, Ed (1996).

As used herein, the term "anti-IL-13 receptor" in reference to an antibody, includes reference to an antibody which is generated against an IL-13 receptor (IL-13R) or against a subunit thereof. In a particularly preferred embodiment, the antibody is generated against human IL-13R synthesized by a non-primate mammal after introduction into the animal of cDNA which encodes a human IL-13R.

A ligand or a receptor "specifically binds to" a compound analyte when the ligand or receptor functions in a binding reaction which is determinative of the presence of the analyte in a sample of heterogeneous compounds. Thus, the ligand or receptor binds preferentially to a particular analyte and does not bind in a significant amount to other compounds present in the sample. For example, a polynucleotide specifically binds to an analyte polynucleotide comprising a complementary sequence and an antibody specifically binds under immunoassay conditions to an antigen analyte bearing an epitope against which the antibody was raised.

"Immunoassay" refers to a method of detecting an analyte in a sample in which specificity for the analyte is conferred by the specific binding between an antibody and a ligand. This includes detecting an antibody analyte through specific binding between the antibody and a ligand. See Harlow and Lane (1988) ANTIBODIES, A LABORATORY MANUAL, Cold Spring Harbor Publications, New York, for a description of immunoassay formats and conditions that can be used to determine specific immunoreactivity.

A "targeting moiety" is the portion of an immunoconjugate intended to target the immunoconjugate to a cell of interest. Typically, the targeting moiety is an antibody, a scFv, a dsFv, an Fab, or an $F(ab')_2$. With respect to the IL-13 receptor, appropriate targeting moieties include IL-13, IL-13 which has been mutated by changing various residues of native sequence, but which maintain the capability to bind the IL-13 receptor, and circularly permuted IL-13 which maintains the capability to bind the IL-13R.

A "toxic moiety" is the portion of a immunotoxin which renders the immunotoxin cytotoxic to cells of interest. Most commonly, the toxic moiety is a protein cytotoxin, such as *Pseudomonas* exotoxin; however, other toxins, such as radioisotopes, can also be conjugated to the targeting moiety if desired.

Persons of skill will recognize that a molecule, such as an antibody, is considered to be a "moiety" once it is incorporated into a chimeric molecule such as an immunoconjugate. Thus, an antibody which binds the IL-13R might be considered as a targeting molecule prior to its conjugation to a toxin, but will usually be referred to as a "targeting moiety" once it is conjugated to an effector molecule, such as a cytotoxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Fusion protein" refers to a polypeptide formed by the joining of two or more polypeptides through a peptide bond formed by the amino terminus of one polypeptide and the carboxyl terminus of the other polypeptide. A fusion protein may is typically expressed as a single polypeptide from a nucleic acid sequence encoding the single contiguous fusion protein. However, a fusion protein can also be formed by the chemical coupling of the constituent polypeptides.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *PROTEINS*, W.H. Freeman and Company, New York (1984).

Two proteins are "homologs" of each other if they exist in different species, are derived from a common genetic ancestor and share at least 70% amino acid sequence identity.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Naturally-occurring" as applied to an object refers to the fact that the object can be found in nature. For example, an amino acid or nucleotide sequence that is present in an organism (including viruses) that can be isolated from a source in nature and which has not been intentionally modified by man in the laboratory is naturally-occurring.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier.

"Pharmacologically effective amount" refers to an amount of an agent effective to produce the intended pharmacological result.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON's PHARMACEUTICAL SCIENCES,: 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal.

"Administration" of a composition refers to introducing the composition into the subject by a chosen route of administration. For example, if the chosen route is intravenous, the composition is administered by introducing the composition into a vein of the subject.

"Treatment" refers to prophylactic treatment or therapeutic treatment.

"Alleviate," with reference to a symptom of a condition, refers to a reduction in the incidence or of the severity of the symptom, or both.

A "prophylactic" treatment is a treatment administered to a subject who does not exhibit signs of a disease or exhibits only early signs for the purpose of decreasing the risk of developing pathology.

A "therapeutic" treatment is, a treatment administered to a subject who exhibits signs of pathology for the purpose of diminishing or eliminating those signs.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression cassette" refers to a recombinant nucleic acid construct comprising an expression control sequence operatively linked to an expressible nucleotide sequence. An expression cassette generally comprises sufficient cis-acting elements for expression; other elements for expression can be supplied by the host cell or in vitro expression system.

"Expression vector" refers to a vector comprising an expression cassette. Expression vectors include all those known in the art, such as cosmids, plasmids (e.g., naked or contained in liposomes) and viruses that incorporate the expression cassette.

A first sequence is an "antisense sequence" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360 (1987). The method used is similar to the method described by Higgins & Sharp, *CABIOS* 5:151-153. (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g. version 7.0 (Devereaux et al., *Nuc. Acids Res.* 12:387-395 (1984).

Another example of algorithms that are suitable for determining percent sequence identity and sequence similarity are the BLAST and the BLAST 2.0 algorithm, which are described in Altschul et al., *J. Mol. Biol.* 215:403-410 (1990) and Altschul et al., *Nucleic Acids Res.* 25:3389-3402 (1977)). Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915 (1989)).

"Stringent hybridization conditions" refers to 50% formamide, 5×SSC and 1% SDS incubated at 42° C. or 5×SSC and 1% SDS incubated at 65° C., with a wash in 0.2×SSC and 0.1% SDS at 65° C.

"Naturally-occurring" as applied to an object refers to the fact that the object can be found in nature. For example, an amino acid or nucleotide sequence that is present in an organism (including viruses) that can be isolated from a source in nature and which has not been intentionally modified by man in the laboratory is naturally-occurring.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

Nucleic acid sequences encoding immunoconjugates useful in the practice of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., supra, Berger and Kimmel (eds.), supra, and Ausubel, supra. Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc., (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding anti-IL-13R antibodies can be modified to form antibodies or immunoconjugates useful in the practice of the present invention. Modification by site-directed mutagenesis is well known in the art. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-IL-13R antibody (typically an scFv) into a vector which comprises the cDNA encoding the toxic moiety. The insertion is made so that the scFv and the toxic moiety are read in frame, that is in one continuous polypeptide which contains a functional Fv region and a functional toxic moiety. In a particularly preferred embodiment, cDNA encoding PE is ligated to a scFv so that the toxin is located at the amino terminus of the scFv.

Once the nucleic acids encoding a toxic moiety, anti-p9 or p16 antibody, or an immunoconjugate of the present invention are isolated and cloned, one may express the desired protein in a recombinantly engineered cell such as bacteria, plant, yeast, insect and mammalian cells as discussed above in connection with the discussion of expression vectors encoding p9 or p16. It is expected that those of skill in the art are knowledgeable in the numerous expression systems available for expression of proteins including E. coli, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made.

One of skill would recognize that modifications can be made to a nucleic acid encoding a polypeptide of the present invention (i.e., anti-p9 or p16 antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation site, additional amino acids placed on either terminus to create conveniently located restriction sites, or additional amino acids (such as poly His) to aid in purification steps.

In addition to recombinant methods, immunoconjugates useful in the practice of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from E. coli or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

Targeting Moieties

A. Introduction

A variety of molecules can be used to target immunoconjugates, such as immunotoxins, to IL-13 receptor ("IL-13R")-expressing cells. The IL-13 receptor is a cell surface receptor that specifically binds IL-13 and mediates a variety of physiological responses in various cell types. The IL-13 receptor may be identified by contacting a cell or other sample with labeled IL-13 and detecting the amount of specific binding of IL-13 according to methods well known to those of skill in the art.

Alternatively, an anti-IL-13 receptor antibody may also be used to identify IL-13 receptors. The antibody will specifically bind to the IL-13 receptor and this binding may be detected either through detection of a conjugated label or through detection of a labeled second antibody that binds the anti-IL-13 receptor antibody.

In preferred embodiments, the targeting molecule is a molecule that binds to the IL-13R and, in preferred embodiments, the targeting molecule is a molecule that specifically binds to the IL-13R. The term "specifically binds", as used herein, when referring to a protein or polypeptide, refers to a binding reaction which is determinative of the presence of the protein or polypeptide in a heterogeneous population of proteins and other biologics. Thus, under designated conditions (e.g. immunoassay conditions in the case of an antibody), the specified ligand or antibody binds to its particular "target" protein (e.g. an IL-13R protein) and does not bind in a significant amount to other proteins present in the sample or to other proteins to which the ligand or antibody may come in contact in an organism.

Like many cytokines, the IL-13R is composed of some polypeptide chains shared with receptors for one or more other cytokine, and one or more. chains that are unique to the IL-13R (sometimes referred to by those in the art as a "private chain"). IL-13 shares some chains with the IL-4 receptor ("IL-4R"). Depending on the degree of specificity desired, therefore, the targeting molecule can be specific for an IL-13R "private chain" or for one shared with the IL-4R. For the uses and methods of the present invention, targeting molecules that bind to chains shared by the IL-13R and by the IL-4R may be used. For example, IL-13 used as a ligand can bind to both the IL-13R and to the IL-4R. In preferred embodiments, the targeting molecule binds only to the IL-13 receptor. For example, antibodies can be generated against the IL-13 receptor, and run on a column containing bound IL-4. The antibodies eluting through the column will bind to the IL-13R but not the IL4R.

In general, preferred targeting molecules for use in the present invention are anti-IL-13R antibodies, mutated anti-IL-13R antibodies that retain the capability to bind to IL-13R, IL-13, mutated IL-13 that retains the capability to bind to IL-13R, and circularly permuted IL-13.

B. Anti-IL13R Antibodies

A variety of immunoassay formats may be used to select antibodies specifically immunoreactive with an IL-13 receptor protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Similarly, assay formats for detecting specific binding of a ligand (e.g. IL-13) with its respective receptor are also well known in the art.

In a preferred embodiment the moiety utilized to specifically target the IL-13 receptor is either an antibody that specifically binds the IL-13 receptor (an anti-IL-13R antibody) or a ligand, such as IL-13, that specifically binds to the receptor.

One of skill will recognize that other molecules besides IL-13 will specifically bind to IL-13 receptors. Polyclonal and monoclonal antibodies directed against IL-13 receptors provide particularly suitable targeting molecules in the chimeric molecules of this invention. The term "antibody", as used herein, includes various forms of modified or altered antibodies, such as an intact immunoglobulin, various fragments such as an Fv fragment, an Fv fragment containing only the light and heavy chain variable regions, an Fv fragment linked by a disulfide bond (Brinkmann, et al. Proc. Natl. Acad. Sci. USA, 90: 547-551 (1993)), an Fab or (Fab)'.sub.2 fragment containing the variable regions and parts of the constant regions, a single-chain antibody and the like (Bird et al., Science 242: 424-426 (1988); Huston et al., Proc. Nat. Acad. Sci. USA 85: 5879-5883 (1988)). The antibody may be of animal (especially mouse or rat) or human origin or may be chimeric (Morrison et al., Proc Nat. Acad. Sci. USA 81: 6851-6855 (1984)) or humanized (Jones et al., Nature 321: 522-525 (1986), and published UK patent application #8707252). Methods of producing antibodies suitable for use in the present invention are well known to those skilled in the art and can be found described in such publications as Harlow & Lane, Antibodies: A Laboratory Manual, Cold Spring Harbor Laboratory (1988), and Asai, Methods in Cell Biology Vol. 37: Antibodies in Cell Biology, Academic Press, Inc. N.Y. (1993).

Antibodies that specifically bind the IL-13 receptor may be produced by a number of means well known to those of skill in the art. Typically, an immunogen, such as isolated IL-13R, is mixed with an adjuvant and animals are immunized with the mixture. When appropriately high titers of antibody to the immunogen are obtained, blood is collected from the animal and antisera are prepared. If desired, further fractionation of the antisera to enrich for antibodies reactive to the polypeptide is performed. See, e.g. Coligan, CURRENT PROTOCOLS IN IMMUNOLOGY, Wiley/Greene, N.Y. (1991); and Harlow & Lane, supra, which are incorporated herein by reference.

Monoclonal antibodies may be obtained by various techniques familiar to those skilled in the art. Description of techniques for preparing such monoclonal antibodies maybe found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, Nature 256:495-497 (1975); and particularly (Chowdhury, P. S., et al., Mol. Immunol. 34:9 (1997)), which discusses one method of generating monoclonal antibodies.

In preferred embodiments, the monoclonal antibody is a scFv. Methods of making scFv antibodies have been described. See, Huse, et al., supra; Ward, et al. Nature 341: 544-546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., Mol. Immunol. 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

One of skill in the art will recognize that there are numerous methods of isolating all or components of the IL-13 receptor for use as an antigen. For example, IL-13 receptors may be isolated by cross-linking the receptor to a labeled IL-13 by the exposure to 2 mM disuccinimidyl suberate (DSS). The labeled receptor may then be isolated according to routine methods and the isolated receptor may be used as an antigen to raise anti-IL-13 receptor antibodies as described below. Cross-linking and isolation of components of the IL-13 receptor is described in Example 3.

In a preferred embodiment, IL-13 receptors may be isolated by means of affinity chromatography. For example, it has been found that many solid tumor cells overexpress IL-13 receptors, permitting ready isolation of IL-13R. For example, approximately, 100 million renal carcinoma cells may be solubilized in detergent with protease inhibitors according to standard methods. The resulting lysate is then run through an affinity column bearing IL-13. The receptor binds to the IL-13 in the column thereby effecting an isolation from the lysate. The column is then eluted with a low pH buffer to dissociate the IL-13 receptor from the IL-13 ligand, resulting in isolated receptor. The isolated receptor may then be used as an antigen to raise anti-IL-13 receptor antibodies.

In preferred embodiments, the targeting molecule is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In a particularly preferred embodiment, the antibody is a single chain Fv ("scFv"). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced. One of skill will realize that conservative variants of the antibodies can be made. Such conservative variants employed in scFv fragments will retain critical amino acid residues necessary for correct folding and stabilizing between the $V_H$ and the $V_L$ regions. In another preferred embodiment, the antibody is a disulfide stabilized Fv ("dsFv"). Methods of making dsFvs are taught in, e.g., U.S. Pat. Nos. 6,147,203; 6,074,644; and 5,747,654. U.S. Pat. No. 5,980,895 discloses immunotoxins comprising PE molecules joined to a dsFv.

In some embodiments of the present invention, the scFv antibody is directly linked to the effector molecule ("EM") through the light chain. However, scFv antibodies can be linked to the EM via its amino or carboxyl terminus. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. No. 4,946,778, U.S. Pat. No. 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, and more preferably no more than 20 amino acids in length. In some embodiments, the peptide linker is a concatamer of the sequence Gly-Gly-Gly-Ser, preferably 2, 3, 4, 5, or 6 such sequences.

The IL-13R targeting molecules can be linked to EMs, such as cytotoxins, through the EM carboxyl terminus, the EM amino terminus, through an interior amino acid residue of the EM such as cysteine, or any combination thereof. Similarly, if the targeting molecule is an antibody, the EM can be linked directly to the heavy, light, Fc (constant region) or framework regions of the antibody. Linkage can occur through the antibody's amino or carboxyl termini, or through an interior amino acid residue. Further, multiple EM molecules (e.g., any one of from 2-10) can be linked to the antibody and/or multiple antibodies (e.g., any one of from 2-5) can be linked to an EM.

C. IL-13, Mutated IL-13, and cpIL-13

One of skill in the art will appreciate that IL-13, analogues of IL-13, and fragments of IL-13 will also specifically bind to the IL-13 receptor. For example, conservative substitutions of residues (e.g., a serine for an alanine or an aspartic acid for a glutamic acid) comprising native IL-13 will provide IL-13 analogues that also specifically bind to the IL-13 receptor. Thus, the term "IL-13", when used in reference to a targeting molecule, also includes fragments, analogues or peptide mimetics of IL-13 that also specifically bind to the IL-13 receptor.

Molecules suitable as targeting moieties include IL-13, mutated IL-13 (such as IL-13 with amino acid substitutions) that retains the capacity to bind to the IL-13 receptor, and circularly permuted IL-13 ("cpIL-13") that retains the capacity to bind to the IL-13 receptor. A number of mutants of IL-13 that retain capacity to bind IL-13 have been made and are discussed in, e.g., WO 01/34645 and WO 01/25282, both of which are incorporated herein by reference.

Circular permutation is functionally equivalent to taking a straight-chain molecule; fusing the ends (directly or through a linker) to form a circular molecule, and then cutting the circular molecule at a different location to form a new straight chain molecule with different termini (see, e.g., Goldenberg, et al. J. Mol. Biol., 165: 407-413 (1983) and Pan et al. Gene 125: 111-114 (1993)). Circular permutation thus has the effect of essentially preserving the sequence and identity of the amino acids of a protein while generating new termini at different locations. U.S. Pat. No. 6,011,002 provides guidance regarding circular permutation in general. U.S. Pat. No. 5,919,456 provides extensive teaching regarding the circular permutation of IL-13 in particular.

Toxic Moieties

A. Introduction

Toxic molecules can be bound to targeting molecules to yield chimeric molecules, such as immunotoxins. Exemplary toxins include ricin, abrin, diphtheria toxin and subunits thereof, ribotoxin, ribonuclease, saporin, and calicheamicin, as well as botulinum toxins A through F. These toxins are well known in the art and many are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and RCA120 according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Conjugating ribonucleases to targeting molecules for use as immunotoxins is discussed in, e.g., Suzuki et al., Nat Biotech 17:265-70 (1999). Exemplary ribotoxins such as α-sarcin and restrictocin are discussed in, e.g., Rathore et al., Gene 190:31-5 (1997) and Goyal and Batra, Biochem 345 Pt 2:247-54 (2000). Calicheamicins were first isolated from *Micromonospora echinospora* and are members of the enediyne antitumor antibiotic family that cause double strand breaks in DNA that lead to apoptosis. See, e.g., Lee et al., J. Antibiot 42:1070-87 (1989). The drug is the toxic moiety of an immunotoxin in clinical trials. See, e.g., Gillespie et al., Ann Oncol 11:735-41 (2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the invention, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is provided in U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., (1989), supra. The PE molecule has been extensively studied in the last decade, and a number of cytotoxic variants of the protein are known. Several immunotoxins employing PE as a toxic moiety have shown success in clinical trials.

The term "*Pseudomonas* exotoxin" as used herein may refer to a full-length native (naturally occurring) PE or to a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:7) and REDL (SEQ ID NO:8). See, e.g., Siegall, et al., *J. Biol. Chem.* 264:14256-14261 (1989). In preferred embodiments, the cytotoxic fragment of PE retains at least 50%, preferably 75%, more preferably at least 90%, and still more preferably 95% or more of the cytotoxicity of native PE. In particularly preferred embodiments, the cytotoxic fragment is more toxic than native PE.

PE employed in the uses and methods of the present invention include the native sequence modified to reduce non-specific binding, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein).

In preferred embodiments, the PE has been modified to reduce or eliminate non-specific cell binding, frequently by deleting domain Ia as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE described in, e.g., Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have deleted and the molecule commences with a Met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of amino acids 253-364 and 381-613 of PE, which is activated to its cytotoxic form upon processing within a cell (see e.g., U.S. Pat. No. 5,608,039, and Pastan et al., Biochim. Biophys. Acta 1333:C1-C6,(1997)).

In a particularly preferred embodiment, the IL-13 receptor targeted cytotoxins of this invention comprise the PE molecule designated PE38QQR. As noted, PE38 is a truncated form of PE composed of amino acids 253-364 and 381-608. In RE38QQR, the lysine residues at positions 509 and 606 are replaced by glutamine and the residue at 613 is replaced by arginine (Debinski et al. *Bioconj. Chem.*, 5: 40 (1994)).

While in preferred embodiments, the PE is PE4E, PE40, PE38, or PE38QQR, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

B. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

C. Assaying for Cytotoxicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

Administration of Nucleic Acids Encoding IL-13R-Targeted Immunotoxins

The administration of nucleic acids, including antisense molecules, or of vectors comprising nucleic acids, including antisense molecules, is particularly easy with respect to the nasal passages, airways and lungs (collectively, "airways") since the cells of the airways to be transfected are readily accessible and nucleic acids or vectors comprising them can be readily delivered to the cells by aerosol delivery. For example, U.S. Pat. Nos. 5,858,784; 5,765,353, and 5,641, 662, the contents of which are incorporated by reference, teach compositions and methods for delivering nucleic acids to lung cells by aerosolized delivery, methods for transfecting mammalian lung cells in vivo, and methods for obtaining synthesis of an encoded polypeptide. See also, U.S. Pat. Nos. 6,093,567 and 5,240,846 (concerning the transfection of lung cells in connection with cystic fibrosis).

In addition to the methods, compositions, and vectors taught in the patents referenced above, cells of the airways can be transfected with nucleic acids encoding IL-13R-targeted immunotoxins by any convenient means. In some embodiments, the nucleic acids can be injected directly into cells of the nasal passage, of the airway, or of the lung using so-called "needleless" "biolistic" devices or gene guns. The biolistic devices typically accelerate a particle, such as a gold particle coated with the nucleic acid of interest, directly into a tissue of interest. Gene guns typically accelerate a liquid containing a nucleic acid, or a dry formulation containing the nucleic acid, into the tissue by gas pressure. Such DNA can be in the form of a plasmid, can be so-called "naked" DNA, and can be circular or linearized. In some embodiments, the nucleic acids are stabilized with an excipient, often a carbohydrate such as trehalose, and may be lypophilized. Methods and devices for transfecting cells that may be utilized in the uses and methods of the present invention are well known in the art and are taught in, for example, Felgner, et al., U.S. Pat. No. 5,703,055; Furth and Hennighausen, U.S. Pat. No. 5,998, 382; Falo et al., WO 97/11605; Erdile et al., WO 99/26662; and Donnelly et al., WO 99/52463. See also, Sakaguchi et al., WO 96/12808; Volkin et al., WO 97/40839; and Robinson et al., WO 95/20660. A variety of methods are known in the art for formulating microparticles suitable for needleless injection into a tissue. See, e.g., Osborne, WO 00/13668.

It should be noted that expression of IL-13R-targeted immunotoxins does not have to occur in an IL-13R-expressing cell. It is expected that other cells will be transfected and that the expressed IL-13R-targeted immunotoxins will be secreted into the mucus or other fluid lining the exterior surface of the cells facing on the lumen of the nasal passage, airway, or lung. The IL-13R-targeted immunotoxin can then migrate in the mucus or other fluid until it reaches a cell expressing an IL-13R. In some embodiments, however, the IL-13R-targeted immunotoxins can be transferred to IL-13R-3 expressing cells by direct injection. Depending on the location to be injected, such injections can be made stereotactically, typically in conjunction with X-rays of the area of interest to assist the practitioner in placing the needle. Stereotactic injection is especially common in the case of injections of the lungs. The practitioner can also be guided in making the injections by imaging technologies such as ultrasound which permit visualization of the needle and of the area to be injected. The choice of how to access the tumor for transfection is within the expertise of the practitioner.

In some embodiments, the nucleic acids may be placed in a viral vector. Transfection by retroviral, adeno-associated virus, lentivirus, adenoviruses, and, lentiviruses pseudotyped with vesiular stomatitis virus, canarypoxvirus, and chickenpox virus vectors, for example, has been taught in the art and can be employed in the practice of the invention. In some preferred embodiments, the nucleic acids are delivered in liposomes. Liposome encapsulation is preferred for needle injection since the liposomes tend to spread somewhat more than viral vectors at an injection site and therefore have more opportunity to contact IL-13R-expressing cells. U.S. Pat. No. 5,880,103 describes several methods of delivery of nucleic acids encoding peptides. The methods include liposomal delivery of the nucleic acids (or of the synthetic peptides themselves).

Nucleic acids encoding IL-13R-targeted immunotoxins or vectors containing such nucleic acids can therefore be used for the manufacture of medicaments to introduce the IL-13R-targeted immunotoxins into IL-13R-expressing cells or cells in the vicinity of such cells, thereby killing the IL-13R expressing cells.

In some embodiments, the nucleic acids to be delivered to cells of the airway are antisense nucleic acids to reduce the expression of the IL-13R or of IL-13. In preferred forms, the antisense molecules reduce the expression of IL-13R. Typically, antisense molecules which selectively bind to mRNA encoding IL-13 or IL-13R are expressed via expression cassettes operably linked to subsequences of the respective gene and generally comprise 20-50 base long sequences in opposite orientation to the mRNA to which they are targeted. The design of antisense oligonucleotides and their use to inhibit or modulate the expression of a target polypeptide is well known in the art, as reflected by the scores of U.S. patents issued between 1996 and the filing date of this application concerning this subject, including U.S. Pat. Nos. 6,346,416; 6,344, 323; 6,339,071; 6,335,194; 6,331,399; 6,306,655; 3,606,606; 6,303,374; and 6,287,860. It should be noted that Vitravene™, an antisense drug, was approved by the FDA for marketing in 1998.

In preferred embodiments, the antisense nucleic acids to reduce expression of the IL-13R or of IL-13 are antisense molecules to IL-13, to the IL-13R, or to the IL-13Rα2 chain.

Administration of Immunotoxins

In some embodiments, the compositions for administration will, comprise a solution of the immunoconjugate dissolved in a pharmaceutically acceptable carrier, preferably an aqueous carrier. A variety of aqueous carriers can be used, e.g., buffered saline and the like. In some embodiments, the compositions can be administered by instilling them in the nasal passages. Conveniently, this can be done in the form of nose drops. This administration format is particularly useful for the alleviation of symptoms of allergic rhinitis.

In some important embodiments, the immunotoxins or nucleic acids or vectors comprising them are administered by aerosolized liquid or powder, which is inhaled by the subject into the lungs. In one group of these embodiments, the compositions comprise dry powders suitable for inhalation. A variety of compositions have been developed in the last decade for use in dry powder inhalers, as have devices for promoting the inhalation of the compositions and methods of manufacturing and handling dry powders suitable for such use. See, e.g., WO 01/78693; WO 01/78695; WO 01/68169; U.S. Pat. Nos. 6,221,338; 6,071,498; and 5,975,076; GB 2363987; and WO 00/53157.

Liquids comprising immunotoxins or nucleic acids or vectors comprising them are administered by nebulizing, atomizing or aerosolizing the liquid and permitting the subject to inhale the resulting atomized or aerosolized liquid. Medical nebulizers that generate a fine spray or nebula of a liquid for inhalation by a patient are well-known devices commonly used for the treatment of various conditions. In nebulizers, for example, a gas and a liquid are typically mixed together and directed against a baffle. As a result, the liquid is aerosolized, that is, the liquid is caused to form small particles that are suspended in the air. This aerosol of the liquid can then be inhaled into a patient's respiratory tract. A nebulizer for efficiently and reliably administering an aerosolized liquid to an inhaling patient is taught in, for example, U.S. Pat. No. 6,044,841. If desired, the liquid can also be delivered to the lung or other portion of the airway by an apparatus, such as by adapting the laparoscopic device for delivery of an aerosolized liquid claimed in U.S. Pat. No. 5,722,950.

The solutions and powders for use in the methods of the invention are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on lung volumes, body weight and the like in accordance with the particular mode of administration selected and the patient's needs.

Thus, a typical pharmaceutical immunotoxin composition for administration by the methods of the present invention would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered to alleviate symptoms of allergy, asthma, or pulmonary-related symptoms of $T_H2$-like cytokine mediated disorders such as the granulomas formed around *Mycobacterium tuberculosis* during tuberculosis infections. In these applications, compositions are administered to a patient suffering from one of these conditions, in an amount sufficient to alleviate the symptom. An amount adequate to accomplish this is defined as a "therapeutically effective dose." Amounts effective for this use will depend upon the severity of the disease and the general state of the patient's health. An effective amount of the compound is that which provides either subjective relief of the symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release formulations of the immunoconjugate compositions can be administered, particularly as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y. pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992), both of which are incorporated herein by reference.

Polymers can be used for ion-controlled release of immunoconjugate compositions. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,811, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins are included a variety of disease conditions caused by specific human cells that may be eliminated by the toxic action of the fusion protein. One preferred application for the immunotoxins of the invention is the treatment of IL-13R expressing cells in the bronchial tree or nasal passages, or both.

EXAMPLES

The following examples are offered to illustrate, but not to limit the claimed invention.

Example 1

This Example sets forth the materials and methods used in the studies reported in Examples 2 and 3.

Murine Model of Chronic Fungal-Induced Allergic Airway Disease

Specific-pathogen free (SPF), female CBA/J mice were purchased from the Jackson Laboratories (Bar Harbor, Me.) and were maintained in a SPF facility for the duration of the studies reported herein. Prior approval for mouse usage was obtained from the University Laboratory of Animal Medicine facility at the University of Michigan Medical School. Systemic sensitization of mice to a commercially available preparation of soluble *A. fumigatus* antigens was performed as previously described (Hogaboam, C. M. et al., *Aspergillus fumigatus. Am. J. Pathol.* 156:723 (2000)). Seven days after the third intranasal challenge, each mouse received $5.0 \times 10^6$ *A. fumigatus* conidia suspended in 30 µl of 0.1% Tween-80 via the intratracheal route (Hogaboam, C. M. et al., *Aspergillus fumigatus. Am. J. Pathol.* 156:723 (2000)).

IL-13-PE38QQR Therapy During Fungal-Induced Allergic Airway Disease

IL-13-PE38QQR (IL13-PE) is a recombinant chimeric fusion protein comprised of human IL-13 and a mutated *Pseudomonas* exotoxin, and it has been previously used to target IL-13 receptor-expressing tumor cells (Husain, S. R. et al., *Blood* 95:3506 (2000); Kawakami, K. et al., *Hum Gene Ther* 11:1829 (2000)). The previous studies have demonstrated that IL13-PE is cytotoxic when incorporated into cells that express IL-4Rα, IL-13Rα1, and IL-13Rα2. Because this chimeric molecule had not been previously employed in a model of allergic airway disease, a pilot study was conducted to determine a range of doses of IL13-PE that were appropriate for in vivo testing. This preliminary study showed that 50 ng of IL13-PE in 1 ml of tissue culture medium had a minor effect on the survival of cultured pulmonary fibroblasts whereas 200 ng/ml of this chimeric protein markedly attenuated fibroblast survival by greater than 60%. Based on these preliminary observations, groups of five to ten *A. fumigatus*-sensitized mice received 50, 100 or 200 ng of IL13-PE dissolved in 20 µl of phosphate buffered saline containing 0.25% human serum albumin (HSA-PBS or diluent) via an intranasal bolus. IL-13 receptor-positive cells were targeted with IL13-PE from days 14 to 28 after the conidia challenge to coincide with marked increases in IL-13 receptor and protein levels in this model (Blease, K. et al., *J. Immunol.* 166:5219 (2001)). In addition, since *A. fumigatus* conidia are typically absent in the airways of *A. fumigatus*-sensitized mice at day 14 after an intratracheal conidia challenge (Hogaboam, C. M. et al., *Aspergillus fumigatus. Am. J. Pathol.* 156:723 (2000)), this time was selected as the starting point for IL13-PE treatment to avoid any confounding effects of IL13-PE on the innate immune response required for the clearance of conidia from allergic mice (Blease, K. et al., *J Immunol* 165:2603 (2000); Blease, K. et al., *J Immunol* 166:1832 (2001)). Day 14 after conidia also corresponds with peak peribronchial accumulations of eosinophils and CD4+ T cell, significant airway hyperresponsiveness to methacholine, goblet cell hyperplasia, and sub-epithelial collagen deposition in *A. fumigatus*-sensitized mice (Hogaboam, C. M. et al., *Aspergillus fumigatus. Am. J. Pathol.* 156:723 (2000)). Another group of ten *A. fumigatus*-sensitized mice received 20 µl of diluent via the same route beginning at day 14 and concluding on day 28 after conidia.

Measurement of Bronchial Hyperresponsiveness

At day 28 after the *A. fumigatus* conidia challenge, bronchial hyperresponsiveness in IL13-PE-treated and control mice was measured in a Buxco™ plethysmograph (Buxco, Troy, N.Y.) as previously described (Hogaboam, C. M. et al., *Aspergillus fumigatus. Am. J. Pathol.* 156:723 (2000)). Sodium pentobarbital (Butler Co., Columbus, Ohio; 0.04 mg/g of mouse body weight) was used to anesthetize each mouse prior to its intubation for ventilation with a Harvard pump ventilator (Harvard Apparatus, Reno, Nev.). The following ventilation parameters were used: tidal volume=0.25 ml, breathing frequency=120/min, and positive end-expiratory pressure≅3 cm $H_2O$. Within the sealed plethysmograph mouse chamber, transrespiratory pressure (i.e. Δ tracheal pressure–Δ mouse chamber pressure) and inspiratory volume or flow were continuously monitored online by an adjacent computer, and airway resistance was calculated by the division of the transpulmonary pressure by the change in inspiratory volume. Following a baseline period in the mouse chamber, each mouse received doses of methacholine ranging from 62.5 to 250 µg/kg of methacholine by tail vein injection, and airway responsiveness to this bronchoconstrictor was again calculated online. The data shown herein is focused on a dose of 125-µg/kg methacholine because this methacholine dose failed to elicit a response in non-sensitized mice but elicited maximal changes in airway hyperresponsiveness in *A. fumigatus*-sensitized mice after the conidia challenge. At the conclusion of the assessment of airway responsiveness, a bronchoalveolar lavage (BAL) was performed with 1 ml of normal saline. Approximately 500 µl of blood was then removed from each mouse and transferred to a microcentrifuge tube. Sera were obtained after the sample was centrifuged at 10,000 rpm for 5 min. Whole lungs were finally dissected from each mouse and snap frozen in liquid $N_2$ or prepared for histological analysis.

Morphometric Analysis of Leukocyte Accumulation in BAL Samples

Lymphocytes and macrophages were enumerated in BAL samples cytospun (Shandon Scientific, Runcorn, UK) onto coded microscope slides. Each slide was stained with a Wright-Giemsa differential stain, and the average number of each cell type was determined after counting a total of 300 cells in 10-20 high-powered fields (HPF; 1000×) per slide. A total of $1 \times 10^6$ BAL cells were cytospun onto each slide to compensate for differences in cell retrieval.

Whole Lung Histological Analysis

Whole lungs from both groups of mice at day 28 after *A. fumigatus* conidia challenge were fully inflated with 10% formalin, dissected and placed in fresh formalin for 24 h. Routine histological techniques were used to paraffin-embed the entire lung, and 5 µm sections of whole lung were stained with hematoxylin and eosin (H & E) or with Periodic Acid Schiff (PAS). Inflammatory infiltrates and structural alterations were examined around small airways and adjacent blood vessels using light microscopy at a magnification of 200×.

Preparation of cDNA and Reverse Transcriptase (RT)-PCR Amplification

Total RNA was prepared from whole lung samples removed from mice in the IL13-PE-treated and control groups at day 28 after the conidia challenge. RNA was isolated using TRIzol® Reagent according to the manufacturer's (Life Technologies, Gibco BRL) directions. The purified RNA was subsequently reverse transcribed into cDNA utilizing a BRL reverse transcription kit and oligo (dT) 12-18 primers. The amplification buffer contained 50 mM KCl, 10 mM Tris-HCl (pH 8.3, and 2.5 mM $MgCl_2$). Specific oligonucleotide primers were added (200 ng/sample) to the buffer; along with 5 µl of reverse transcribed cDNA sample. The following murine oligonucleotide primers were used: IL-4 receptor α sense—GAGTGAGTGGAGTCCTAGCATC (SEQ ID NO:1), IL-4 receptor α antisense—GCTGAAG-TAACAGAACAGGC (SEQ ID NO:2); IL-13 receptor α1 sense—GAATTTGAGCGTCTCTGTCGAA (SEQ ID NO:3), IL-13 receptor α1 antisense—GGTTATGCCAAAT-GCACTTGAG (SEQ ID NO:4); IL-13 receptor α2 sense—

ATGGCTTTTGTGCATATCAGATGCT (SEQ ID NO:5), IL-13 receptor α2 antisense—CAGGTGTGCTC-CATTTCATTCTAAT (SEQ ID NO:6).

These mixtures were then first incubated for 5 min at 94° C. and amplified using the following cycling parameters: IL-4Rα: cycled 38 times at 94° C. for 30 s, 58° C. for 45 s, and elongated at 72° C. for 70 s. IL-13α1R: cycled 38 times at 94° C. for 30 s, 66° C. for 60 s, and elongated at 72° C. for 70 s. IL-13α2R: cycled 38 times at 94° C. for 30 s, 66° C. for 60 s, and elongated at 72° C. for 70 s. After amplification the samples were separated on a 2% agarose gel containing 0.3 µg/ml of ethidium bromide and bands visualized and photographed using a translucent UV source.

ELISA and Total Soluble Collagen Analysis

Murine IL-13, IL-4, IL-12, IFN-γ, and C10 chemokine levels were measured in 50-µl samples from whole lung homogenates using a standardized sandwich ELISA technique previously described in detail (Evanoff, H. et al., *Immunol. Invest.* 21:39 (1992)). BAL fluids from the diluent and IL13-PE groups were also screened for IFN-γ. Each ELISA was screened to ensure antibody specificity and recombinant murine cytokines, and chemokines were used to generate the standard curves from which the concentrations present in the samples were derived. The limit of ELISA detection for each cytokine was consistently above 50 pg/ml. The Sircol™ Collagen Assay (Biocolor Ltd., Belfast, Ireland) was used to measure the soluble forms of collagen present in the same lung homogenates. This assay was developed from the Sirius Red-based histochemical procedure. The cytokine and collagen levels in each sample were normalized to total protein levels measured using the Bradford assay.

Serum levels of IgE, IgG1 and IgG2a at day 28 after conidia in the diluent and IL13-PE treatment groups were analyzed using complementary capture and detection antibody pairs for IgE, IgG1 and IgG2a (PharMingen, San Diego, Calif.). Immunoglobulin ELISAs were performed according to the, manufacturer's directions. Duplicate sera samples were diluted to 1:100 for IgE determination and 1:10 for determination of IgG levels. Immunoglobulin levels were then calculated from optical density readings at 492 nm, and immunoglobulin concentrations were calculated from a standard curve generated using recombinant IgE, IgG1 or IgG2a (both standard curves ranged from 5-2000 pg/ml).

Statistical Analysis

All results are expressed as mean i standard error of the mean (SE). A one-way ANOVA and a Dunnett's Multiple Comparisons Test were used to reveal statistical differences between the control group and the IL13-PE treatment groups at day 28 after the conidia challenge; $P<0.05$ was considered statistically significant.

Example 2

The following Example sets forth the results of certain studies conducted in the course of the present invention.

IL-13-PE38QQR Therapy Significantly Reduced Airway Hyperresponsiveness During Chronic Fungal-Induced Allergic Airway Disease.

Airway hyperresponsiveness following a systemic methacholine challenge is a persistent feature of chronic fungal allergic airway disease in mice (Hogaboam, C. M. et al., *Aspergillus fumigatus. Am. J. Pathol.* 156:723 (2000)). As shown in FIG. 1, the airway resistance measured in the group of mice that received diluent from day 14 to 28 after the conidia challenge was $19.2\pm4.6$ cm $H_2O$/ml/sec, and this represented an approximately 8-fold increase above the baseline resistance (dashed line shown in FIG. 1). Mice that received 50 ng of IL13-PE from day 14 to 28 after conidia exhibited airway hyperresponsiveness following methacholine provocation that was similar to that elicited in the control group at day 28. However, airway resistance in mice that received 100 ng of IL13-PE over the same time period was significantly ($P\leqq0.05$) lower than that measured in the control group ($19.2\pm4.6$ vs. $9.4\pm2.9$ cm $H_2O$/ml/sec; FIG. 1). Likewise, mice that received 200 ng of IL13-PE exhibited significantly ($P\leqq0.01$) lower methacholine-induced airway resistance compared with the control group ($19.2\pm4.6$ vs. $5.4\pm1.4$ cm $H_2O$/ml/sec; FIG. 1). These data suggested that, in a dose-dependent manner, IL13-PE inhibited airway hyperresponsiveness associated with chronic fungal-induced Allergic Airway Disease.

Administration of 200-ng IL-13-PE38QQR Significantly Reduced the Numbers of T Lymphocytes in the Bronchoalveolar Lavage (BAL) from Mice with Chronic Fungal Induced Allergic Airway Disease.

Previous studies have demonstrated that T lymphocytes are the primary effectors of airway hyperresponsiveness (Corry, D. B. et al., *Mol Med* 4:344 (1998)), and that both IL-4 (Cohn, L. et al., *J Immunol* 161:3813 (1998)) and IL-13 (Grunig, G. et al., *Science* 282:2261 (1998)) have major, and possibly distinct, roles in this response. Th2 lymphocytes appear to be the primary source of IL-4 (Corry, D. B. et al., *Mol Med* 4:344 (1998)), whereas alveolar macrophage appears to be the primary lung source of IL-13 during atopic asthma (Prieto, J., et al., *Respir Med* 94:806 (2000)). Because both types of cells also respond to IL-4 and IL-13 in a receptor-dependent manner (Murata, T. et al., *Biochem Biophys Res Commun* 238:90 (1997); Graber, P. et al., *Eur J Immunol* 28:4286 (1998)), it was examined whether IL13-PE therapy during chronic allergic airway responses to *Aspergillus* affected the numbers of T cells and macrophages in the airways of these mice. T lymphocytes (FIG. 2A) and macrophages (FIG. 2B) were enumerated in BAL samples from all groups of mice at day 28 after conidia challenge. Only the 200-ng IL13-PE treatment significantly reduced the number of T lymphocytes present in BAL samples compared with numbers of these cells in similar samples from the control group (FIG. 2A). None of the IL13-PE treatments significantly altered the numbers of BAL macrophages compared with number of BAL macrophages in the diluent group (FIG. 2B). Furthermore, few eosinophils and neutrophils were identified in BAL samples from all groups at day 28 after the conidia challenge, and these findings were consistent with previous observations in this model (Hogaboam, C. M. et al., *Aspergillus fumigatus. Am. J. Pathol.* 156:723 (2000); Blease, K. et al., *J Immunol* 165:2603 (2000); Blease, K. et al., *J Immunol* 166:1832 (2001); Blease, K. et al., *J Immunol* 165:1564 (2000)). Thus, the 200-ng IL13-PE treatment significantly reduced T lymphocyte but not macrophage numbers in the airways of *A. fumigatus*-sensitized mice exposed to *A. fumigatus* conidia.

Administration of IL-13-PE38QQR Significantly Attenuated the Peribronchial Inflammation and Goblet Cell Hyperplasia Characteristic of Chronic Fungal-Induced Allergic Airway Disease.

As previously reported (Hogaboam, C. M. et al., *Aspergillus fumigatus. Am. J. Pathol.* 156:723 (2000)), the introduction of conidia into *A. fumigatus*-sensitized mice promotes a marked and persistent peribronchial accumulation of T lymphocytes and mononuclear cells. In the present study, pronounced airway inflammation was observed in allergic mice that received diluent alone. In contrast, the airways of mice in all three IL13-PE treatment groups exhibited a clear paucity of inflammatory leukocytes, and the greatest reduction in peribronchial inflammation was observed in whole lung sections from mice that received 200 ng of IL13-PE. The airways of SPF mice have few, if any, mucus-producing goblet cells, so an increase in the number of these cells reflects an induction of mucin-gene expression. In the present study, goblet cells were easily identified in the bronchial epithelium of allergic mice that received diluent, or 50 ng of IL13-PE. However, only scattered goblet cells were detected in the airways of mice that received 100 ng of IL13-PE and the airways of mice treated with the highest dose of IL13-PE completely lacked PAS-positive goblet cells. Therefore, the therapeutic effects of IL13-PE were manifest at a histological level as evidenced by decreased peribronchial inflammation and goblet cell hyperplasia/mucus production.

Administration of 200-ng IL-13-PE38QQR Significantly Attenuated Peribronchial Fibrosis in Mice with Chronic Fungal-Induced Allergic Airway Disease.

Figure 3:
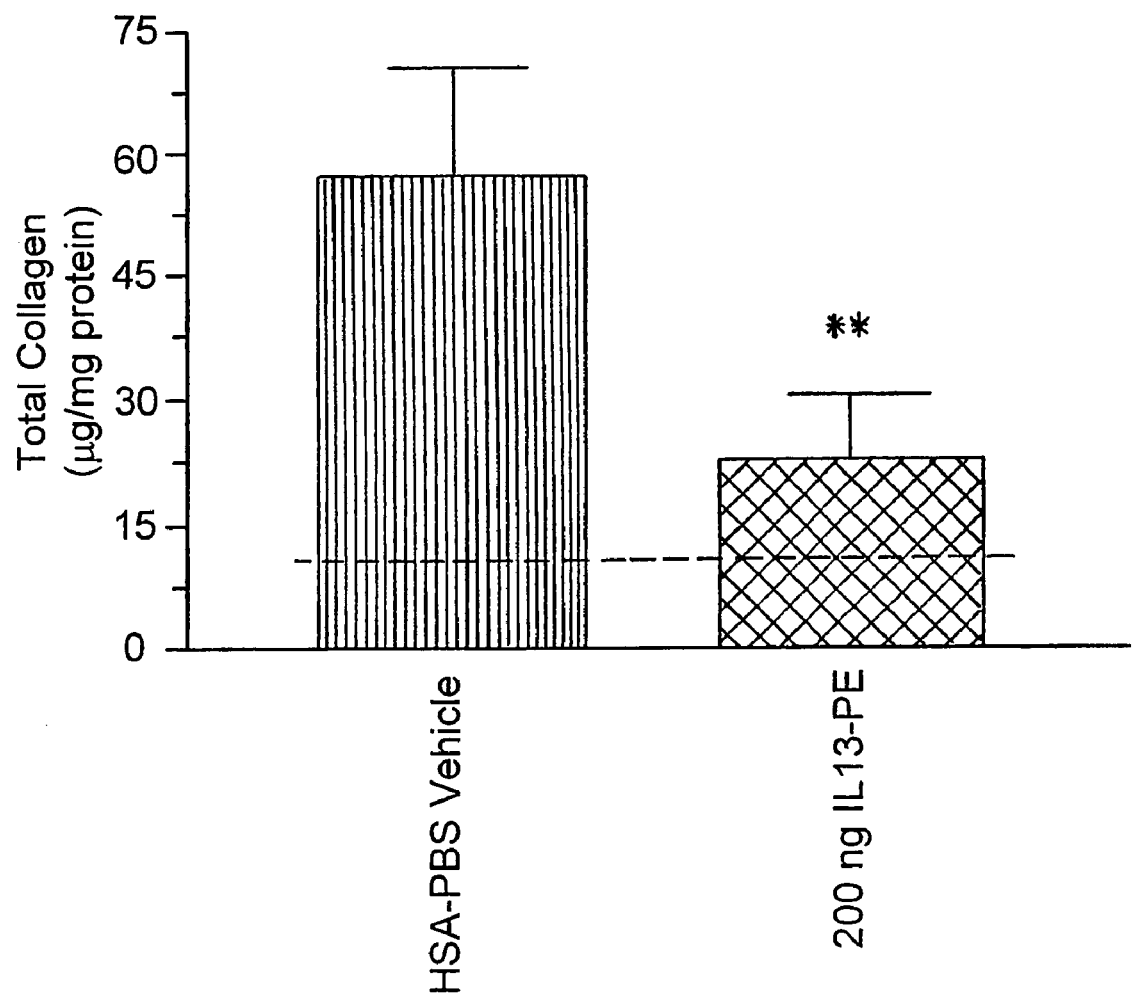
FIG. 3: Total collagen levels in whole lung homogenates at day 28 after *A. fumigatus* conidia challenge in the control (HSA-PBS vehicle) and IL-13-PE38QQR (IL13-PE) treatment groups. *A. fumigatus*-sensitized mice received diluent or 200 ng of IL13-PE every other day starting at day 14 and concluding at day 28 after a conidia challenge (see Materials and Methods). Total collagen levels were measured as described in the Materials and Methods section, and the dashed line indicates the mean total soluble collagen levels in *A. fumigatus*-sensitized mice prior to the conidia challenge (10±3 μg/mg protein). Values are expressed as mean±SE; n=10 mice/group. **P±0.01 compared with levels measured in the control treatment group at day 28 after the conidia challenge.

Peribronchial fibrosis is another prominent feature of the remodeled airway in mice with chronic fungal-induced allergic airway disease (Hogaboam, C. M. et al., *Aspergillus fumigatus. Am. J. Pathol.* 156:723 (2000)) and previous studies have shown that IL-13 is a major mediator of fibroblast activation and tissue fibrosis (Doucet, C. et al., *J Clin Invest* 101:2129 (1998); Oriente, A. et al., *J Pharmacol Exp Ther* 292:988 (2000); Chiaramonte, M. G. et al., *J. Clin. Invest.* 104:777 (1999)). In the present study, the peribronchial distribution of extracellular matrix and fibroblasts was pronounced around the airways of the control group of mice at day 28 after the conidia challenge. Conversely, peribronchial fibrosis was markedly diminished around the airways of mice that received 200 ng of IL13-PE from days 14 to 28 after the conidia challenge. Histological examination of lungs from the other two IL13-PE treatment groups revealed little effect of lower doses of this chimeric protein on peribronchial fibrosis. Analysis of total collagen levels in whole lung homogenates from the diluent and 200 ng IL13-PE treatment groups of mice confirmed that less peribronchial fibrosis was present in IL13-PE-treated mice at day 28 after the conidia challenge (FIG. 3). Again, the two lower doses of IL13-PE did not reduce total soluble collagen levels in whole lung samples. Taken together, these data suggest that targeting lung cells that recognize IL-13 significantly reduced the degree of peribronchial fibrosis associated with chronic fungal allergic airway disease in mice.

Administration of 200-ng IL-13-PE38QQR During Chronic Fungal-Induced Allergic Airway Disease Dramatically Reduced Whole Lung mRNA Levels of IL-13 Receptor α1 and IL-4 Receptor.

Figure 4:
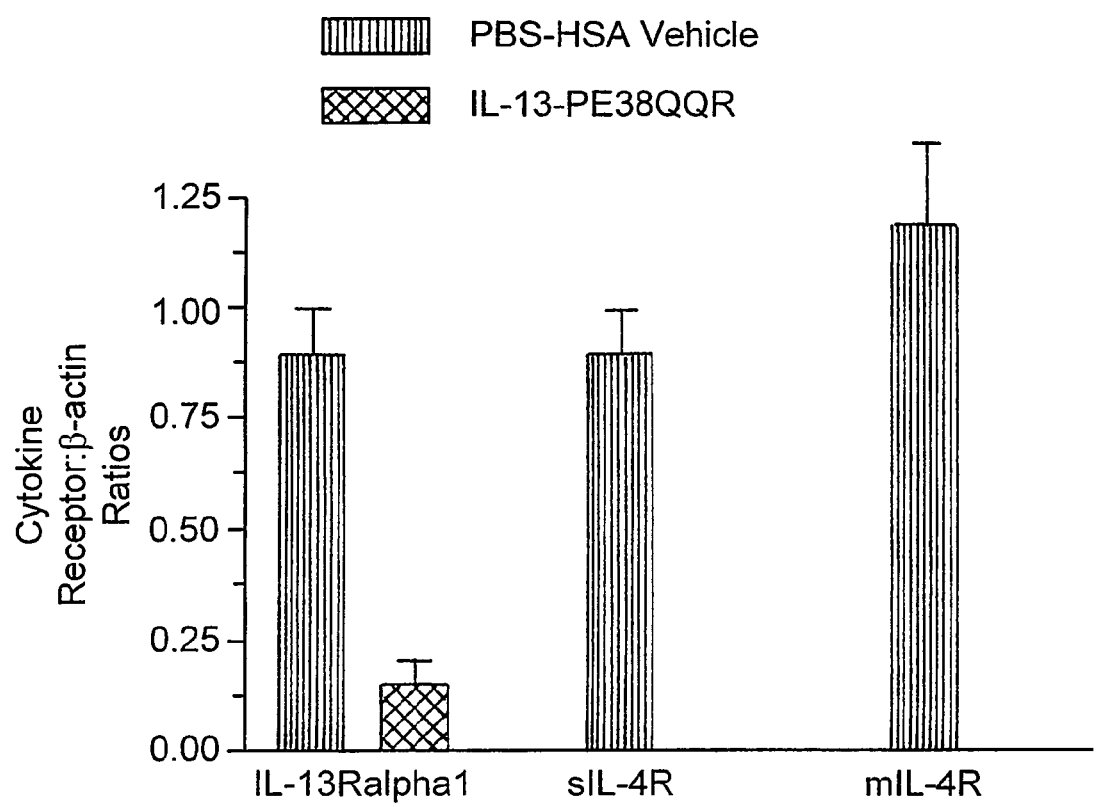
FIG. 4: RT-PCR analysis of β-actin, IL-13 receptorα1 (IL-13Rα1) and IL-4 receptor α in whole lung samples from *A. fumigatus*-sensitized mice at day 28 after the conidia challenge after diluent or 200-ng IL-13-PE38QQR (IL13-PE) treatment for 14 days. At day 28 after the conidia challenge, whole lung mRNA for IL-13Rα1 and IL4Rα were prominent in mice that received the diluent alone. Conversely, the 200-ng IL13-PE therapy markedly diminished or abolished the whole lung mRNA levels of all three receptors. Although IL-13Rα2 mRNA was expressed in whole lung samples from non-sensitized mice, this receptor was not detected in whole lung samples from either treatment group of allergic mice. Densitometry analysis was used to determine the ratios of IL-13Rα1, sIL-4Rα, and mIL-4Rα mRNA: β-actin mRNA in both treatment groups of allergic mice. These ratios confirmed that the mRNA levels for sIL-4Rα, mIL-4Rα and IL-13Rα1 were markedly reduced or abolished in the 200-ng IL13-PE treatment group compared with the diluent group.

It was determined whether the 200-ng IL13-PE treatment modulated mRNA levels of these receptors in the lungs of *A. fumigatus*-sensitized mice challenged with conidia 28 days previously. Whole lung mRNA levels from control- and IL13-PE-treated *A. fumigatus*-sensitized mice were analyzed for IL-13Rα1, IL-13Rα2 and IL-4Rα (both soluble and membrane associated isoforms of IL-4R) expression using RT-PCR. The whole lung levels of IL-13Rα1 mRNA were markedly reduced whereas mRNA for soluble and membrane-associated IL-4Rα were absent in mice that received the 200-ng IL13-PE treatment from days 14 to 28 compared with mice that received diluent over the same time. The ratio of cytokine receptor:β-actin based on densitometry analysis is shown in FIG. 4. In contrast, the 50- and 100-ng IL13-PE treatments did not markedly reduce mRNA levels of IL-13Rα1 and IL-4Rα in whole lung samples compared with the respective diluent alone group. Interestingly, no IL-13Rα2 was detected in any group at day 28 after the conidia challenge, whereas this IL-13R chain was detected in whole lungs taken from non-allergic mice. Taken together, these data showed that the IL13-PE treatment abolished the whole lung mRNA for IL-13Rα1 and IL-4Rα suggesting that administration of chimeric immunotoxins markedly reduced the numbers of IL-13-responsive cells in the lung.

Administration of 200-ng IL-13-PE38QQR Did Not Significantly Affect Circulating Levels of IgE, but Significantly Reduced IgG1 and Significantly Increased IgG2α.

Serum levels of total IgE, IgG1 and IgG2a are summarized in FIG. 5. Following the diluent or IL13-PE treatment at day 28 after conidia, all groups of mice exhibited similar levels of serum IgE suggesting that the IL13-PE treatments did not affect the production of IgE in this model. IgG1 and IgG2a levels are shown in FIGS. 5B & C, respectively. At day 28 after conidia, IgG1 levels were significantly decreased in the 200-ng IL13-PE treatment group, but not the other IL13-PE treatment groups, compared with the day 28 diluent group (FIG. 5B). However, IgG2a levels were significantly higher in the 200-ng IL13-PE treatment group than IgG2a levels measured at day 28 in the diluent group (FIG. 5C). Thus, these data show that the 200-ng IL13-PE treatment inhibited the production of IgG1, which is normally associated with a Th2 immune response, and promoted the production of IgG2a, which is normally associated with a Th1 immune response.

Administration of 200-ng IL-13-PE38QQR Significantly Increased Whole Lung Levels of IL-13, but not IL-4 or IL-12.

Whole lung levels of EL-13, IL-4 and IL-12 were measured in all four-treatment groups at day 28 after the conidia challenge and these ELISA results are summarized in FIG. 6. All three cytokines were elevated above baseline levels detected in *A. fumigatus*-sensitized mice prior to the conidia challenge (dashed lines shown in FIG. 6). Neither the 50- or 100-ng IL13-PE treatments significantly altered whole lung levels of IL-13 (panel A), IL-4 (panel B) and IL-12 (panel C) compared with the control group. Whole lung IL-13 levels were significantly elevated in the 200-ng IL13-PE treatment group compared with the control group (FIG. 6A), but IL-4 and IL-12 levels did not differ between this IL13-PE treatment group and the control group (FIGS. 6B & C, respectively). Thus, these data show that IL13-PE therapy did not inhibit lung levels of IL-13, IL-4 and IL-12 in this model. In addition, it appears that administration of 200-ng IL13-PE reduced the number of IL-13-responsive cells in the lung, considering that whole lung levels of IL-13 were significantly increased in this treatment group.

The Administration of 200-ng IL-13-PE38QQR Significantly Increased BAL and Whole Lung Levels of IFN-γ.

Figure 7:
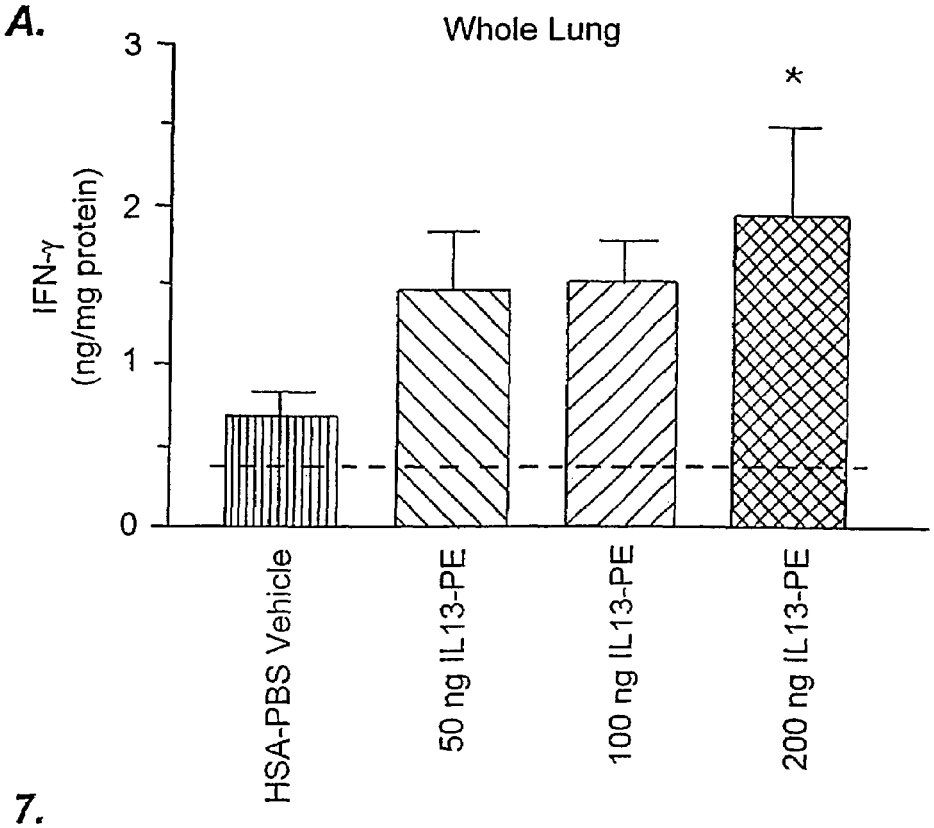
FIG. 7.
Figure 7:
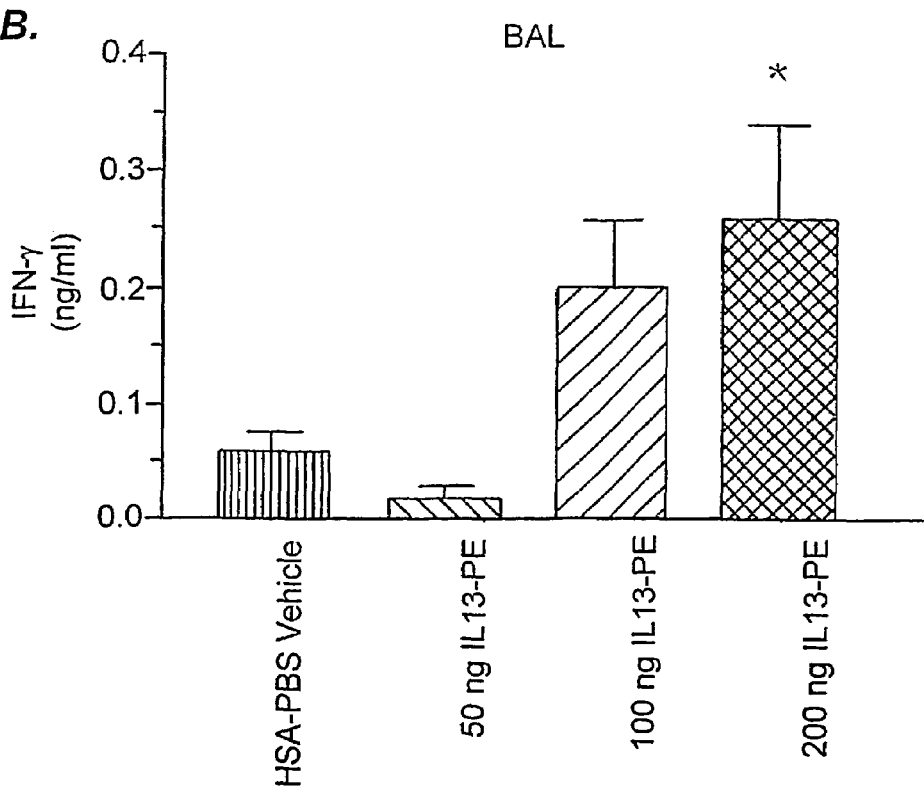

Previous studies have shown that IFN-γ is a potent inhibitor of many of the physiological and histological features of allergic airway disease induced by ovalbumin (Cohn, L. et al., *J Exp Med* 190:1309 (1999)) and *A. fumigatus* conidia (Blease, K. et al., *J Immunol* 165:1564 (2000)). The effect of the diluent and IL13-PE therapies on whole lung and BAL levels of IFN-γ is shown in FIG. 7. Markedly greater amounts of IFN-γ were detected in both compartments at day 28 after the conidia challenge compared with IFN-γ levels measured in similar samples from *A. fumigatus*-sensitized mice prior to the conidia challenge. Whole lung IFN-γ levels were increased in all of the IL13-PE treatment groups but this elevation reached statistical significance in the 200-ng IL13-PE treatment alone (FIG. 7A). Likewise, immunoreactive IFN-γ levels were increased in BAL samples from the 100- and 200-ng IL13-PE treatment groups, but only BAL IFN-γ levels in the latter group reached statistical significance compared with BAL levels from the control group (FIG. 7B). These data demonstrated that the Th1 cytokine response in *A.*

*fumigatus*-sensitized mice was significantly increased at day 28 after the conidia challenge and intranasal IL13-PE chimeric protein therapy.

Example 3

This Example discusses the results of the studies reported in the previous Example.

There is considerable evidence that asthma is an inflammatory disease of the airways that is caused by an imbalance in the activity of lung-associated T lymphocytes (Liu, A. H. *Allergy Asthma Proc* 21:227 (2000); Prieto, J., et al., *Respir Med* 94:806.(2000); Jones, P. D. et al., *Med Hypotheses* 55:40-(2000)). Specifically, asthma is characterized by a predominance of Th2 lymphocytes in the airways that appear to generate abnormal quantities of IL-4, IL-5 and IL-13 (Colavita, A. M. et al., *Clin Chest Med* 21:263 (2000) *Proc Soc Exp Biol Med* 215:11 (1997)). The effect of increased levels of Th2 cytokines in the asthmatic airways appears to be magnified by a relative deficiency in the levels of the Th1 cytokine, IFN-γ, produced by Th1 lymphocytes (Renzi, P. M. et al., *Am J Respir Crit Care Med* 159:1417 (1999)). Nevertheless, previous attempts to amplify Th1-mediated responses using recombinant IL-12 (Bryan, S. A. et al., *Lancet* 356:2149 (2000)) or inhibit Th2-mediated responses using anti-IL-5 therapy (Leckie, M. J. et al., *Lancet* 356:2144 (2000)) were modestly successful in the treatment of clinical asthma. Clinical asthmatic responses triggered by *A. fumigatus* mirror this abnormal cytokine pattern since pulmonary levels of Th2 cytokines are substantially higher than levels of Th1 cytokines.

The present studies examined the utility of selective targeting of lung cells that bind IL-13 with a toxin. This was facilitated by the delivery of a exemplar chimeric protein that contained human IL-13 and a derivative of *Pseudomonas* exotoxin, PE38QQR. IL-13-PE38QQR or IL13-PE has been used successfully in the eradication of IL-13R-positive tumors (Husain, S. R. et al., *Blood* 95:3506 (2000); Kawakami, K. et al., *Hum Gene Ther* 11:1829 (2000)). In the present study, it was observed that IL13-PE therapy in mice with established fungal allergic airway disease markedly reduced IL-13Rα1 mRNA levels in the lung and dose-dependently reversed the airway hyperresponsiveness and remodeling typically associated with this model. Most notably, the intranasal administration of 200 ng of IL13-PE from day 14 to day 28 after conidia challenge markedly increased the lung-associated levels of IFN-γ suggesting that the targeting of IL-13-responsive cells was effective in promoting levels of this anti-allergic cytokine (Cohn, L. et al., *J Exp Med* 190: 1309 (1999)).

Lung cells that bind IL-13 were specifically targeted during chronic airway response to *Aspergillus* in mice because of the evidence that this Th2 cytokine is prominently expressed during clinical asthma (Huang, S. K. et al., *J Immunol* 155: 2688 (1995); Corry, D. B. *Curr Opin Immunol* 11:610 (1999)) and has a major and distinct role during experimental allergic airway disease (Grunig, G. et al., *Science* 282:2261 (1998); Wills-Karp, M., *Science* 282:2258 (1998); Webb, D. C. et al., *J Immunol* 165:108 (2000)). It is important to note that IL-4 and IL-13 share heteromultimeric receptor complexes of variable composition. The biologic responses induced by IL-4 or IL-13 requires a complex interaction of signaling pathways and regulators (Jiang, H. et al., *J Allergy Clin Immunol* 105: 1063.(2000)). The classical IL-4 receptor is found on hematopoietic cells and consists of IL-4Rα and IL-2Rγ (or γ chain) whereas the alternative form of IL-4 receptor consists of the IL-4Rα and IL-13Rα1 chains (Murata, T. et al., *Blood* 91:3884 (1998)). Since the alternative IL-4 receptor contains IL-13Rα1, it can also recognize IL-13 and it appears that this receptor is the major IL-13R in hematopoietic and nonhematopoietic cells (Murata, T. et al., *Int. J. Molecular Medicine* 1:551 (1998); Obiri, N. I. et al., *J Biol Chem* 270:8797 (1995)). An additional receptor, IL-13Rα2, binds to IL-13 with 100-fold higher affinity than IL-13Rα1, but appears to lack the cytoplasmic domain necessary for intracellular signaling (Osawa, M. et al., *Immunogenetics* 51:974 (2000)). Previous studies have demonstrated that IL13-PE effectively binds to both IL-13 receptors, but exhibits a much higher affinity for IL-13Rα2 than for IL-13Rα (Kawakami, K. et al., *Blood* 97:2673 (2001)). In the present study, we observed that administration of 200-ng IL13-PE markedly reduced mRNA levels of membrane and soluble IL-4Rα, as well as IL-13Rα1, and increased whole lung IL-13 levels in the lungs of allergic mice. These findings indicate that administration of 200-ng IL13-PE successfully targeted cells that normally express IL-13Rα1 as well as lung-associated cells that are expressing IL-4Rα. Interestingly, IL-13Rα2 mRNA was only detected in whole lung samples from non-sensitized, SPF mice; mRNA for this IL-13 receptor was not detected in any lung samples from *A. fumigatus*-sensitized mice prior to or after conidia challenge. This finding is intriguing in light of growing evidence that IL-13Rα2 may function as a decoy receptor for IL-13, thereby limiting the biologic effects of IL-13 (Feng, N. et al., *Lab Invest* 78:591 (1998)). Furthermore, the lack of IL-13Rα2 in the lungs of allergic mice may be one explanation for the persistence of allergic airway disease in *A. fumigatus*-sensitized mice exposed to fungal conidia.

Given that T lymphocytes are the primary effectors during a wide array of allergic airway responses (Corry, D. B. et al., *Mol Med* 4:344 (1998); MacLean, J. A. et al., *Am J Respir Cell Mol Biol* 20:379 (1999); Krinzman, S. J. et al., *Am J Physiol* 271:L476 (1996)), it is clear that this cell and the mediators it produces are appropriate targets during the treatment of atopic asthma (Kon, O. M. et al., *Int Arch Allergy Immunol* 118:133 (1999)). It has been previously observed that despite the fact that eosinophils are the most abundant and major effector cell type in the airways up to day 14 after a conidia challenge in *A. fumigatus*-sensitized mice, T lymphocytes are the predominant cellular effectors in this model at later times (Hogaboam, C. M. et al., *Aspergillus fumigatus. Am. J. Pathol.* 156:723 (2000)). Furthermore, enhancing IL-12 (Bryan, S. A. et al., *Lancet* 356:2149 (2000)) or neutralizing IL-5 (Leckie, M. J. et al., *Lancet* 356:2144 (2000)) during clinical asthma has been shown to have little effect on airway responsiveness to spasmogen or antigen challenge, despite the fact that these treatments markedly reduced blood and sputum eosinophil numbers. In the present study, a prominent consequence of IL13-PE treatment was the marked and dramatic reduction in the numbers of T lymphocytes in and around the airways of *A. fumigatus*-sensitized mice challenged with conidia 28 days previously. Activated T lymphocytes highly express IL-4Rα, but unlike B lymphocytes and monocytes, resting or activated T cells exhibit little or no surface expression of IL-13Rα1 (Murata, T. et al., *Biochem Biophys Res Commun* 238:90 (1997); Graber, P. et al., *Eur J Immunol* 28:4286 (1998)). Therefore, it is not immediately clear from the current study whether the IL13-PE treatment directly killed T lymphocytes present in the lung, altered the apoptotic status of these cells, or inhibited mechanisms that promote the emigration of these cells into the lungs. Support for the latter possibility comes in the form of preliminary observations that the IL13-PE therapy significantly inhibited the production of a potent T cell chemoattractant, C10 chemokine. Since C10 chemokine has a major proinflammatory role during acute *A. fumigatus*-induced allergic airway disease (Hogaboam, C. M. et al., *J Immunol* 162:6071 (1999)), further studies are necessary to determine whether a reduction in C10 levels could account for the decreased numbers of T lymphocytes in this allergic airway model.

The importance of airway remodeling during clinical asthma remains controversial (Bento, A. M. et al., *Allergy Asthma Proc* 19:353 (1998); Krishnaswamy, G. et al., *V.H.S.J.* 4:44 (1999) Boulet, L. P. et al., *Can Respir J* 5:16 (1998)) but postmortem studies clearly reveal that airway wall thickening is present in asthmatic patients, and this observation appears to correlate to the severity of airway hyperresponsiveness and airflow obstruction (Niimi, A. et al., *Am J Respir Crit Care Med* 162:1518 (2000); Djukanovic, R. *J Allergy Clin Immunol* 105:522 (2000); Vignola, A. M. et al., *J Allergy Clin Immunol* 105:514 (2000)). Airway remodeling is normally characterized by the activation of cells that form the structural and support elements of the airway including epithelial cells, smooth muscle, fibroblasts and endothelial cells (Bento, A. M. et al., *Allergy Asthma Proc* 19:353 (1998)). Asthma is also characterized by increased mucus production that in turn can contribute to airway obstruction (Barnes, P. J. *Br J Clin Pharmacol* 42:3 (1996)). Cohn and colleagues (Cohn, L. et al., *J Immunol* 162:6178 (1999)) have shown that although IL-5, eosinophils, or mast cells are not essential, signaling through the IL-4 receptor is critical for mucus production in the airways of allergic mice. Furthermore, IL-13 exerts a major role in many of these events as evidenced by the profound nonspecific airway hyperresponsiveness, mucus cell metaplasia, and obstruction in mice with the targeted. pulmonary expression of IL-13 (Zhu, Z. et al., *J Clin Invest* 103:779 (1999)). Consistent with these findings is the demonstration that the exogenous delivery of sIL-13Rα2-Fc effectively reduced the hepatic fibrosis associated with schistosomiasis (Chiaramonte, M. G. et al., *J. Clin. Invest.* 104:777 (1999)). Administration of 200-ng IL13-PE had a profound effect on all of the pathological events associated with chronic airway responses to *Aspergillus*. Also of major significance was the finding that administration of 200-ng IL13-PE successfully reversed these features of allergic airway disease. Airway hyperresponsiveness and airway remodeling are well-established features at two weeks after the introduction of *A. fumigatus* conidia into *A. fumigatus*-sensitized mice (Hogaboam, C. M. et al., *Aspergillus fumigatus*. *Am. J. Pathol.* 156:723 (2000)). Thus, the delayed targeting of IL-13-responsive lung cells ameliorates all of the features of established fungal asthma including airway hyperresponsiveness and airway remodeling.

The administration of IL13-PE during chronic fungal-induced allergic airway disease was also associated with a significant increase in the pulmonary levels of IFN-γ, but not IL-4 or IL-12. The effect of IL13-PE on IFN-γ levels coincides with other successful forms of immunotherapy in asthmatics that appear to reduce pulmonary symptoms through promotion of Th1 responses (Jutel, M. et al., *J Immunol* 154:4187 (1995); Durham, S. R. et al., *J Allergy Clin Immunol* 97:1356 (1996); Varney, V. A. et al., *J Clin Invest* 92:644 (1993)) that appear to be suppressed in the background during atopic asthma (Magnan, A. O. et al., *Am J Respir Crit Care Med* 161:1790 (2000)). Investigators have recently proposed that the prevalence of asthma (a Th2 disorder) is inversely proportional to the prevalence of tuberculosis and enteric infection (Th1 disorders) (Jones, P. D. et al., *Med Hypotheses* 55:40 (2000)). Although the development of Th2 cells is impaired in IL-13-deficient mice (McKenzie, G. J. et al., *Immunity* 9:423 (1998)), IL-13, in contrast to IL-4, does not appear to regulate Th-cell differentiation (de Vries, J. E. *J Allergy Clin Immunol* 102:165 (199.8)). Consistent with this observation, it has been noted that the systemic immunoneutralization of IL-4 but not IL-13 during chronic fungal-induced allergic airway disease augments spleen levels of IFN-γ (Blease, K. et al., *J. Immunol.* 166:5219 (2001)). Thus, the administration of IL13-PE in the fungal-induced allergic airway disease model promoted the release of IFN-γ.

In conclusion, IL-13 has been shown to be a central mediator in airway inflammation, hyperreactivity, increased number of goblet cells and excess mucus, all pulmonary features that characterize asthma (Cohn, L. et al., *J Exp Med* 190:1309 (1999); Grunig, G. et al., *Science* 282:2261 (1998); Wills-Karp, M., *Science* 282:2258 (1998); Zuhdi Alimam, M. et al., *Am J Respir Cell Mol Biol* 22:253 (2000)). Given its distinct and dynamic role in the development and maintenance of so many features of asthma, it is clearly important to characterize strategies that safely and effectively target cells that respond to this cytokine. In the present study, prolonged intranasal instillation of a chimeric protein that selectively targeted lung cells expressing IL-13 receptors was well tolerated and effective in the treatment of asthmatic airway disease, thereby obviating the need for antibody or receptor antagonist therapies (de Vries, J. E. et al., *J Allergy Clin Immunol* 103:S492 (1999)).

Example 4

This Example discusses the contribution of signal transducers and activators of transcription (Stat) proteins to asthma and to allergic conditions.

Allergic and asthmatic events elicited through IL-4 and IL-13 receptors involve a group of that Stat proteins, following their phosphorylation by cytokine receptor-associated Janus (JAK) kinases and migration into the nucleus, initiate cytokine responsive gene transcription (Takeda et al., *Cytokine Growth Factor Rev*, 11(3): 199-207 (2000); Wurster et al., *Oncogene*, 19(21): 2577-84 (2000); Murata T et al., *Int J Hematol*, 69(1): 13-20 (1999)). Of the currently described Stat proteins, Stat6 appears to have the most prominent role during IL-4- and IL-13-mediated responses including Th2 differentiation (Kaplan et al., *J Leukoc Biol*, 64(1): 2-5 (1998)) and immunoglobulin class switching to IgE (Kaplan et al., *Immunity*, 4(3): 313-9 (1996)). Variants of Stat6 are present in clinical atopic asthma (Gao et al., *J Med Genet*, 37(5): 380-2 (2000)), and linkage analysis suggests that Stat6 is situated in the chromosomal region containing candidate genes for atopy and asthma (Barnes et al., *J Allergy Clin Immunol*, 104(2 Pt 1): 485-91 (1999)), although the latter finding has garnered controversy (Heinzmann et al., *Clin Exp Allergy*, 30(11): 1555-61 (2000)). At present, the most convincing data implicating Stat6 in allergic airway diseases is derived from experimental studies. Initial examination of mice lacking Stat6 function due to gene deletion revealed that Stat6-deficient (Stat64–/–) mice fail to generate IgE and a Th2 cytokine response and consequently failed to develop airway inflammation, airway hyperresponsiveness, or goblet cell hyperplasia during soluble ovalbumin (OVA)-induced allergic airway disease (Kuperman et al., *J Exp Med*, 187(6): 939-48 (1998); Akimoto et al., *J Exp Med*, 187(9): 1537-42 (1998); Miyata et al., *Clin Exp Allergy*, 29(1): 114-23 (1999)). Subsequent studies in a similar model of OVA-induced allergic airway disease revealed that IL-5 could reconstitute many of the features of this disease in Stat6–/– mice (Tomkinson et al., *Am J Respir Crit Care Med*, 160(4): 1283-91 (1999)). More recent data suggests that Stat6-independent allergic inflammation can arise in the context of chronic OVA allergen challenge (Trifilieff et al., *Br J Pharmacol*, 130(7): 1581-8 (2000)), but it is currently unknown whether IL-4 and IL-13 contribute to Stat6-independent events during allergic airway disease.

Thus, the role of Stat6 during chronic allergic airway disease has been unknown. One useful model for studying the role of Stat6 is the use of the fungus *A. fumigatus* (Hogaboam et al., *Am. J. Pathol.*, 156: 723-732 (2000)) in mice. This murine model recapitulates many of the features of clinical fungal asthma including chronic airway inflammation, airway hyperreactivity, and goblet cell hyperplasia (Kauffman et al., *Am J Respir Crit Care Med*, 151(6): 2109-15; discussion 2116 (1995)). In addition, these airway features persist for several weeks in *A. fumigatus*-sensitized mice that receive a single intrapulmonary challenge with *A. fumigatus* conidia (Blease et al., *J Immunol*, 165(5): 2603-11 (2000), Blease et al., *J Immunol*, 165(3): 1564-72 (2000)). The studies below examine the role of Stat6 in the airway inflammatory and remodeling events during the development of chronic fungal asthma.

Example 5

This Example sets forth the materials and methods used in the studies reported in Examples 6 and 7.

Mice.

The generation of Stat6−/− mice has been previously described in detail (Kaplan et al., *Immunity*, 4(3): 313-9 (1996)). Stat6−/− were backcrossed 10 generations onto a BALB/c genetic background and were bred as homozygotes in the Indiana University Laboratory Animal Resource Center. Wild-type BALB/c (Stat6+/+) mice were purchased from Harlan Bioproducts (Indianapolis, Ind.).

A Chronic Model of *A. fumigatus*-Induced Allergic Asthma.

A model of chronic allergic airway disease induced by *A. fumigatus* conidia that is characterized by airway hyperreactivity, lung inflammation, eosinophilia, mucus hypersecretion, goblet cell hyperplasia, and subepithelial fibrosis has previously been described (Hogaboam et al., *Am. J. Pathol.*, 156: 723-732 (2000); Blease et al., *J Immunol*, 165(5): 2603-11 (2000); Blease et al., *J Immunol*, 165(3): 1564-72 (2000)). Stat6+/+ or Stat6−/− mice were similarly sensitized to a commercially available preparation of soluble *A. fumigatus* antigens. Seven days after the third intranasal challenge, each mouse received $5.0 \times 10^6$ *A. fumigatus* conidia suspended in 30 µl of PBS tween 80 (0.1%; vol/vol) via the intratracheal route (Hogaboam et al., *Am. J. Pathol.*, 156: 723-732 (2000)).

To determine the role of IL-4 and IL-13 in the development of fungus-induced allergic airway disease in the absence of Stat6, IL-13-PE38QQR (IL13-PE) was used to target IL-13 receptor-expressing cells. Based on preliminary observations, a group of ten *A. fumigatus*-sensitized Stat6−/− mice received 200 ng of IL13-PE dissolved in 20 µl of phosphate-buffered saline containing 0.25% human serum albumin (HSA-PBS) via an intranasal bolus once daily. IL-13 receptor-positive cells were targeted with IL13-PE from days 37 to 44 after conidia challenge. Another group of ten *A. fumigatus*-sensitized Stat6−/− mice received 20 µl of IL13-PE vehicle alone once daily via the same route beginning at day 37 and concluding to day 44 after conidia.

Measurement of Bronchial Hyperresponsiveness.

Immediately prior to and at days 21, 30, 38, and 44 after an intratracheal *A. fumigatus* conidia challenge, bronchial hyperresponsiveness was assessed in a Buxco™ plethysmograph (Buxco, Troy, N.Y.) as previously described (Hogaboam et al., *Am. J. Pathol.*, 156: 723-732 (2000)). Sodium pentobarbital (Butler Co., Columbus, Ohio; 0.04 mg/g of mouse body weight) was used to anesthetize mice prior to their intubation and ventilation was carried out with a Harvard pump ventilator (Harvard Apparatus, Reno, Nev.). Once baseline airway resistance was established, 5 µg of methacholine was introduced into each mouse via a cannulated tail vein, and airway hyperresponsiveness was monitored for approximately 3 min. The peak increase in airway resistance was then recorded. After the assessment of airway hyperresponsiveness, approximately 500 µl of blood was removed from each mouse via ocular bleed and centrifuged at 900×g for 10 min to yield serum. A bronchoalveolar lavage (BAL) was then performed using 1 ml of filter-sterilized normal saline. Finally, whole lungs were dissected from each mouse and snap frozen in liquid $N_2$ or fixed in 10% formalin for histological analysis (see below).

Morphometric Analysis of Leukocyte Accumulation in BAL Samples.

Macrophages, eosinophils, neutrophils, and T cells were quantified in BAL samples cytospun (Shandon Scientific, Runcorn, UK) onto coded microscope slides. Each slide was stained with a Wright-Giemsa differential stain, and the average number of each cell type was determined after counting a total of 300 cells in 10-20 high-powered fields (HPF; 1000×) per slide. A total of $1 \times 10^6$ BAL cells were cytospun onto each slide to compensate for differences in cell retrieval.

ELISA, IgE, and Collagen Analysis.

Murine IL-4, IL-13, TGF-β, MCP-1, RANTES, and eotaxin protein levels were determined in 50-µl samples from whole lung homogenates using a standardized sandwich ELISA technique previously described in detail (Evanoff et al., *Immunol. Invest.*, 21: 39-49 (1992)). Total IgE levels were measured in serum samples using a specific ELISA. All ELISAs were screened to ensure the specificity of each antibody used. Nunc-immuno ELISA plates (MaxiSorp) were coated with the appropriate polyclonal capture antibody (R&D Systems, Minneapolis, Minn.) at a dilution of 1-5 µg/ml of coating buffer (in M: 0.6 NaCl; 0.26 $H_3BO_4$; 0.08 NaOH; pH 9.6) overnight at 4° C. The unbound capture antibody was washed away, and each plate was blocked with 2% BSA-PBS for 1 h at 37° C. Each ELISA plate was then washed three times with PBS tween 20 (0.05%; vol/vol), and 50 µl of undiluted or diluted (1:10) whole lung homogenate were added to duplicate wells and incubated for 1 h at 37° C. Following the incubation period, the ELISA plates were thoroughly washed, and the appropriate biotinylated polyclonal detection antibody (3.5 µg/ml) was added. After washing the plates 45 min later, streptavidin-peroxidase (1:5000 dilution, Bio-Rad Laboratories, Richmond, Calif.) was added to each well, incubated for 30 min, and then thoroughly washed again. A chromagen substrate solution (Bio-Rad Laboratories) was added, and optical readings at 492 nm were obtained using an ELISA plate scanner. Recombinant murine cytokines and chemokines (R&D Systems, Rochester, Minn.) were used to generate the standard curves from which the sample concentrations were derived. The limit of ELISA detection for each cytokine was consistently above 50 pg/ml. The Sircol™ Collagen Assay (Biocolor Ltd., Belfast, Ireland) was used to measure the soluble forms of collagen present in the same lung homogenates. This assay was developed from the Sirius Red based histochemical procedure. The cytokine and collagen levels in each sample were normalized to total protein levels measured using the Bradford assay.

Whole Lung Histological Analysis.

Whole lungs from *A. fumigatus*-sensitized Stat6+/+ and Stat6−/− mice prior to and at various times after *A. fumigatus* conidia challenge were fully inflated with 10% formalin, dissected, and placed in fresh 10% formalin for 24 h. Routine histological techniques were used to paraffin-embed the entire lung, and 5 µm sections of whole lung were stained with periodic acid-Schiff reagent (PAS) or Masson trichrome. Morphologic evaluations of inflammatory infiltrates and structural alterations were determined around blood vessels and airways using light microscopy at a magnification of 1000×.

Statistical Analysis.

All results are expressed as mean ± standard error of the mean (SE). A Student's. T test or Analysis of variance (ANOVA) and a Student-Newman-Keuls Multiple Comparison test were used to determine statistical significance between Stat6+/+ and; Stat6−/− mice at various times after the conidia challenge; $P<0.05$ was considered statistically significant.

Example 6

This Example sets forth the results of certain studies regarding the role of Stat6 in asthma and allergic disease.

Stat6-Deficient Mice Exhibit No IgE, Markedly Diminished Goblet Cell Hyperplasia, and Reduced Airways Inflammation During Chronic Fungal Asthma.

Consistent with previous studies, Stat6−/− mice failed to show the generation of serum IgE at any time in the chronic fungal model. Total IgE levels in Stat6+/+ mice exceeded 5 µg/ml of serum at days 21-44 after conidia, whereas total IgE levels in Stat6−/− mice were below the limit of ELISA detection at these same times. Pronounced goblet cell hyperplasia and peribronchial inflammation are characteristically found in the airways following the induction of fungus-induced asthma (Hogaboam et al., *Am. J. Pathol.*, 156: 723-732 (2000)). PAS staining of whole lung sections from *A. fumigatus*-sensitized Stat6+/+ mice revealed a significant increase in goblet cells and mucus, as indicated by magenta staining 30, 38, and 44 days after conidia challenge. Major accumulations of leukocytes around these airways were also observed at all time points. Compared with the Stat6+/+ group, little mucus and minor peribronchial accumulations of leukocytes were detected in the lungs of Stat6−/− mice at 30, 38, or 44 days after conidia challenge in *A. fumigatus*-sensitized mice. This data suggested that goblet cell hyperplasia and peribronchial inflammation during chronic fungal asthma is Stat6-dependent.

Whole Lung Deficits in Macrophage Chemoattractant Protein-1 (MCP-1); Regulated on Activation, Normal T-Cell Expressed and Secreted (RANTES); and Eotaxin in Stat6-Deficient Mice During Chronic Fungal Asthma.

Previous in vitro studies have shown that Stat6 activation is required for the generation of the CC chemokine eotaxin by airway epithelial cells (Matsukura et al., *J Immunol*, 163(12): 6876-83 (1999)) and endothelial cells (Goebeler et al., *Immunology*, 91(3): 450-7 (1997)). Other studies have shown that the synthesis of CC chemokines such as macrophage-derived chemokine and T cell activation gene-3 by primary Th2 cells in culture is also dependent on Stat6 (Zhang et al., *J Immunol*, 165(1): 10-4 (2000)). To determine whether Stat6 deficiency affected the lung levels of eotaxin and other pro-allergic CC chemokines such as MCP-1 and RANTES during chronic fungal asthma, whole lung samples from Stat6+/+ and Stat6−/− mice were-analyzed at days 21, 30, 38, and 44 after the conidia challenge. Whole lung levels of MCP-1, RANTES, and eotaxin were significantly decreased in Stat6−/− mice compared with Stat6+/+ mice at nearly all times examined after the conidia challenge. One exception to this trend was noted at day 30 after the conidia challenge when whole lung levels of eotaxin did not differ between the two groups of mice. Furthermore, it is important to note that significantly higher levels of all three CC chemokines were present in the lungs of Stat6−/− mice at days 30-44 after conidia compared with whole lung levels of these chemokines measured in the day 21 group of Stat6−/− mice. These findings suggested that Stat6 was necessary, in part, for the full expression of MCP-1, eotaxin, and RANTES during chronic fungal asthma.

Stat6-Deficient Mice Develop Airway Hyperresponsiveness During Chronic Fungal Asthma.

Figure 8:
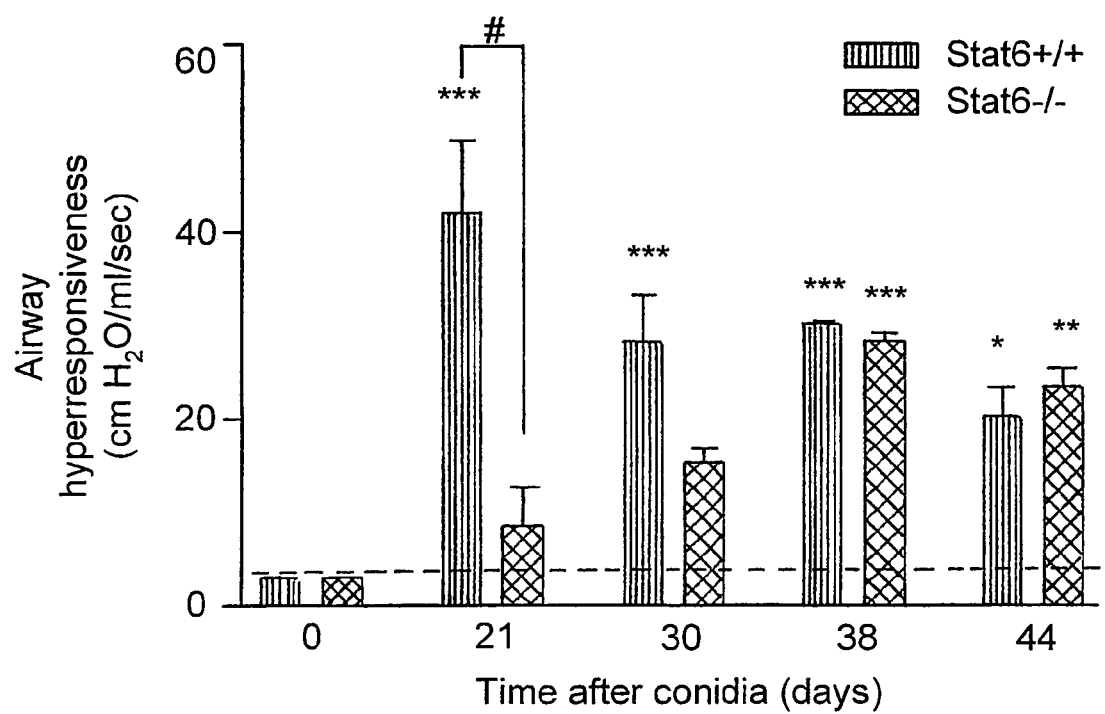
FIG. 8: Airway hyperresponsiveness in *A. fumigatus*-sensitized Stat6-wildtype (+/+) and Stat6-deficient (−/−) mice before and at various times after an *A. fumigatus* conidia challenge. Airway resistance (units=cm H$_2$O/ml/sec) was calculated at each time point prior to (dashed line) and after methacholine (5 µg; i.v.). Values are expressed as mean±SE; n=5/group/time point. *, P<0.05, , P<0.01 and *, P<0.001 demonstrate significant differences in airway resistance compared to levels prior to conidia challenge (time=0). #, P<0.05 demonstrates a significant difference in airway resistance between Stat6+/+ and Stat6−/− mice at day 21 after conidia.

Airway hyperresponsiveness is a persistent and complicating feature of fungus-induced asthma (Kauffman et al., *Am J Respir Crit Care Med*, 151(6): 2109-15; discussion 2116 (1995)). Stat6+/+ mice sensitized to *A. fumigatus* antigen exhibited significantly elevated airway hyperresponsiveness in response to methacholine 21 days after conidia challenge compared with airway responses to methacholine measured in these mice prior to the conidia challenge (FIG. 8). Furthermore, airway hyperresponsiveness. remained significantly elevated in Stat6+/+ mice at days 30, 38, and 44 after the conidia challenge. In contrast, Stat6−/− mice exhibited significantly less airway hyperresponsiveness at day 21 after the conidia challenge compared with Stat6+/+ mice at the same time (FIG. 8). However, Stat6−/− mice exhibited airway hyperresponsiveness similar to that measured in Stat6+/+ mice at days 30, 38, and 44 after conidia (FIG. 8). Thus, these data suggested that airway hyperresponsiveness ultimately manifests in Stat6−/− mice during chronic fungal asthma.

Increased T Cell Recruitment into the Airways of Stat6-Deficient Mice at Day 30 after Conidia.

The infiltration of eosinophils and lymphocytes into the airways has been shown to play a key role in the development of allergic airway disease (Gelfand, *Allergy Asthma Proc*, 19(6): 365-9 (1998)). Given that airway hyperresponsiveness and peribronchial fibrosis were present at day 30, but not at day 21 after conidia in Stat6−/− mice, we examined the appearance of these features of allergic disease was associated with increased leukocyte numbers in the BAL. No significant differences in eosinophil, neutrophil, or macrophage numbers were measured between Stat6+/+ or Stat6−/− mice at any time after conidia. At day 21 after the conidia challenge in *A. fumigatus*-sensitized Stat6+/+ mice, approximately 50% of the cells in the BAL were T cells, whereas T cells comprised less than 1% of the cells in the BAL from Stat6−/− mice at this time. However, at day 30 after the conidia challenge, T cells were prominent in the BAL from both Stat6+/+ and Stat6−/− mice, comprising greater than 20% of the total cells in the BAL. Thus, these findings suggest that the appearance of airway hyperresponsiveness in Stat6−/− mice subsequent to day 30 after conidia may be related to the augmented recruitment of T cells into the airways of these mice.

Peribronchial Fibrosis Occurs in the Absence of Stat6 During Chronic Fungal Asthma.

Previous studies have demonstrated a role for Stat6 in the development of granulomas and collagen deposition (Kaplan et al., *J Immunol*, 160(4): 1850-6 (1998)); therefore, the role of Stat6 in the development of peribronchial fibrosis following the induction of chronic fungal asthma was investigated. Total collagen levels measured in whole lung homogenates were significantly attenuated in Stat6−/− mice compared to Stat6+/+ mice 21 days after conidia challenge. However, total collagen levels in the lungs of Stat6−/− mice were markedly increased at later time points after conidia challenge. No significant differences in collagen levels were detected between Stat6+/+ and Stat6−/− mice 30, 38, or 44 days after conidia challenge in *A. fumigatus*-sensitized mice. Histological analysis of whole lung sections taken from Stat6+/+ and Stat6−/− mice at 30, 38, and 44 days after conidia challenge confirmed these findings. At day 30 after conidia, the increase in total collagen in whole lung samples from Stat6−/− mice coincided with a significant increase in levels of the profibrotic cytokine, TGF-β (FIG. 9B). Thus, the appearance of peribronchial fibrosis was delayed in Stat6−/− mice compared with Stat6+/+ mice, and changes in total lung collagen in the former group coincided with an increase in lung levels of TGF-β.

Temporal Changes in Whole Lung Levels of IL-4 and IL-13 in Stat6−/− Mice During Chronic Fungal Asthma.

To determine whether the absence of Stat6 during chronic fungal asthma influenced levels of Th2 cytokines such as IL-4 and IL-13, whole lung levels of both cytokines were measured at days 21, 30, 38, and 44 after the conidia challenge in *A. fumigatus*-sensitized Stat6+/+ and Stat6−/− mice. Whole lung IL-4 protein levels increased in a time-dependent manner in both groups. At days 21 and 30 after conidia, IL-4 levels in Stat6−/− mice were significantly lower than levels measured in Stat6+/+ at the same time points. However, at days 38 and 44, whole lung IL-4 levels were comparable in both groups. The greatest levels of IL-13 in Stat6+/+ mice were detected at day 30 after conidia. Whole lung IL-13 levels in Stat6−/− mice were significantly lower than levels measured in their wildtype counterparts at the day 21 following the conidia challenge. However, at all subsequent times examined, IL-13 levels were similar in the two groups.

The Development of Airway Hyperresponsiveness in Stat6−/− Mice During Chronic Fungal Asthma is Dependent on IL-13 Receptor Expression.

Our findings show that IL13-PE reverses all of the airway features of chronic fungal asthma when administered from day 14 to 28 after the conidia challenge. In the present study, Stat6−/− mice were treated for seven consecutive days with IL13-PE, and airway hyperresponsiveness following methacholine was determined 44 days after conidia challenge. Airway hyperresponsiveness in Stat6−/− mice treated with vehicle increased significantly after methacholine administration (3.8±0.1 to 19.6±4.1 cm $H_2O$/ml/sec). In contrast, mice treated with IL13-PE exhibited no significant increase in airway hyperresponsiveness from basal levels after methacholine administration. The IL13-PE treatment also completely abolished the presence of T cells, eosinophils, and neutrophils present in BAL samples from Stat6−/− mice at day 44 after conidia.

Histological analysis of whole lung sections from both treatment groups of Stat6−/− mice revealed that peribronchial inflammation was markedly diminished in lung sections from IL13-PE-treated Stat6−/− mice in contrast to Stat6−/− mice that received the vehicle for IL13-PE alone. Examination of trichrome-stained whole lung sections revealed that peribronchial fibrosis was prominent in both Stat6−/− treatment groups. These qualitative findings were confirmed using a quantitative collagen assay. Essentially, IL13-PE therapy from days 38 to 44 after conidia did not reverse the peribronchial fibrosis evident at day 44 after conidia. These data suggest that the development of airway hyperresponsiveness, but not peribronchial fibrosis, in Stat6−/− mice is dependent on IL-13 receptor-expressing cells.

Example 7

This Example discusses the results of the studies set forth in the previous Example.

Given the clinical and experimental relevance of IL-4 and IL-13 during the, development of several features of allergic asthma (Grunig G et al., *Science*, 282(5397): 2261-3 (1998); Wills-Karp et al., *Science*, 282(5397): 2258-61 (1998); Zhu et al., *J Clin Invest*, 103(6): 779-88 (1999)), the cellular and molecular pathways these Th2 cytokines exploit have received considerable research attention. A number of previous experimental studies have established a prominent role for Stat6 signaling during the development of various features of allergic asthma,(Kuperman et al., *J Exp Med*, 187(6): 939-48 (1998); Akimoto et al., *J Exp Med*, 187(9): 1537-42 (1998); Miyata et al., *Clin Exp Allergy*, 29(1): 114-23 (1999); Tomkinson et al., *Am J Respir Crit Care Med*, 160(4): 1283-91 (1999); Trifilieff et al., *Br J Pharmacol*, 130(7): 1581-8 (2000)). These studies clearly showed that the induction of Th2 responses were severely impaired during acute allergen challenge in previously sensitized Stat6−/− mice. However, more recent studies by Trifilieff et al. (Trifilieff et al., *Br J Pharmacol*, 130(7): 1581-8 (2000)) demonstrated that OVA-sensitized Stat6−/− mice could acquire some features of allergic airway disease following a chronic OVA challenge. Given these more recent findings in allergic Stat6−/− mice, we investigated whether Stat6-deficiency would affect the development of chronic fungus-induced asthma characterized by persistent airway hyperresponsiveness and airway remodeling. In the present study, we demonstrated that goblet cell hyperplasia and peribronchial inflammation were largely absent from *A. fumigatus*-sensitized Stat6−/− mice at all times examined after their challenge with *A. fumigatus* conidia. However, allergic Stat6−/− mice ultimately acquired many of the same features of allergic airway disease observed in Stat6-wildtype (+/+) mice after the conidia challenge, particularly airway hyperresponsiveness and peribronchial fibrosis. Additional experiments demonstrated that the selective targeting of IL-13-responsive cells in the lung using IL13-PE abolished airway hyperresponsiveness in Stat6−/− mice. Thus, the present studies highlight that certain prominent characteristics of chronic allergic airway disease can eventually develop in the absence of Stat6, but Stat6-independent airway hyperresponsiveness relies on the presence of IL-13-responsive cells in the lung.

Stat6 appeared to modulate a number of features of chronic fungal asthma regardless of when these parameters were analyzed. First, the present studies confirmed previous observations (Kuperman et al., *J Exp Med*, 187(6): 939-48 (1998)) (Tomkinson et al., *Am J Respir Crit Care Med*, 160(4): 1283-91 (1999)) that serum IgE generation and goblet cell hyperplasia during allergic airway disease unequivocally require Stat6 signaling. Mucus overproduction and goblet cell hyperplasia are characteristic of the remodeled asthmatic airway (Vignola et al., *J Allergy Clin Immunol*, 105(2 Pt 2): 514-517 (2000)), and the appearance of goblet cells in the airways is a Th2-mediated response (Cohn et al., *J Immunol*, 162(10): 6178-83 (1999)) (Cohn et al., *J Exp Med*, 190(9): 1309-18 (1999)). Second, the intensity of allergic airway inflammation was markedly diminished in Stat6−/− mice compared with their wildtype counterparts. Although it was noted that T cell accumulation in the airways of allergic Stat6−/− mice did progressively increase during the course of fungal asthma, the lymphocyte counts in the BAL of Stat6−/− mice remained considerably lower than similar counts in BALs from Stat6+/+ mice. These finding were consistent with those of Trifilieff et al. (Trifilieff et al., *Br J Pharmacol*, 130(7): 1581-8 (2000)) who demonstrated that the airway inflammatory response was only partially mediated by Stat6 in the context of a chronic OVA challenge. Third, it was observed that Stat6 deficiency significantly attenuated the levels of major pro-allergic CC chemokines such as MCP-1, RANTES, and eotaxin (Lukacs et al., *J Clin Invest*, 104(8):

995-9 (1999)). These findings are consistent with results showing that Stat6 was necessary for TNF-α and IL-4 to promote eotaxin gene expression in human airway epithelial cells (Matsukura et al., *J Immunol,* 163(12): 6876-83 (1999)) and for IL-13 to induce MCP-1 in endothelial cells (Goebeler et al., *Immunology,* 91(3): 450-7 (1997)). Our finding that RANTES/CCL5 was also decreased in Stat6−/− mice during chronic fungal asthma was novel; previous studies suggested that this chemokine was a product of Th1 cells (Zhang et al., *J Immunol,* 165(1): 10-4 (2000)). The present study demonstrated that a number of major characteristics of chronic fungal asthma in Stat6+/+ mice were absent or diminished in Stat6−/− mice at all times after conidia challenge.

Persistent airway hyperresponsiveness and airway remodeling due to excessive collagen deposition and subepithelial fibrosis characterize fungus-induced asthma (Hogaboam et al., *Am. J. Pathol.,* 156: 723-732 (2000)). In light of previous studies showing that OVA-sensitized and -challenged Stat6−/− mice remained hyporesponsive to a methacholine challenge (Kuperman et al., *J Exp Med,* 187(6): 939-48 (1998); Akimoto et al., *J Exp Med,* 187(9): 1537-42 (1998); Trifilieff et al., *Br J Pharmacol,* 130(7): 1581-8 (2000)), the delayed appearance of methacholine-induced airway hyperresponsiveness in Stat6−/− mice during chronic fungal asthma was a novel and surprising finding from the present studies. Additionally, the development of pulmonary fibrosis was unique to the present studies, as it had been previously reported that Stat6−/− mice failed to develop pulmonary and hepatic fibrosis in the context of granuloma formation induced by *Schistosoma mansoni* eggs (Kaplan et al., *J Immunol,* 160(4): 1850-6 (1998)). Airway hyperresponsiveness and peribronchial fibrosis were significantly reduced at day 21 after conidia challenge in Stat6−/− mice compared with their wildtype controls, but at all subsequent times after conidia, Stat6−/− mice exhibited vigorous methacholine-induced bronchoconstriction and peribronchial fibrosis comparable to Stat6+/+ mice. Furthermore, the appearance of peribronchial fibrosis at day 30 in the Stat6−/− mice was associated with a significant increase in whole lung levels of the profibrotic cytokine, TGF-β. The discrepancy between the findings herein and those of previous investigators may be linked to the manner in which Stat6−/− mice were sensitized and challenged with allergen, the genetic background of the Stat6−/− mice examined (i.e. BALB/c vs. C57BL/6), and/or the duration over which the features of allergic airway disease was monitored.

Biologic Th2 responses elicited by IL-4 and IL-13 binding to their appropriate receptors involves a complex array of signaling pathways and regulators of which Stat6 appears to be the major contributor (Jiang et al., *J Allergy Clin Immunol,* 105(6 Pt 1): 1063-70 (2000)). The lack of Th2 responses in Stat6−/− mice during acute allergic airway disease was consistent with initial in vitro studies demonstrating the Stat6 requirement for IL-4-induced Th2 cell differentiation and immunoglobulin class switching to IgE (Kaplan et al., *Immunity,* 4(3): 313-9 (1996)). However, more recently, it was shown that NK T cells, which do not require IL-4 for maturation, produce IL-4 in the absence of Stat6. (Kaplan et al., *J Immunol,* 163(12): 6536-40 (1999)). In the present study, Stat6-independent pathways were activated leading to the appearance of airway hyperresponsiveness and peribronchial fibrosis at time points after day 21 post conidia. Although these alternative pathways were not specifically examined in the present study, it is probable that cell-signaling pathways involving Stat3 (Arinobu et al., *Biochem Biophys Res Commun,* 277(2): 317-24 (2000)) and/or phosphatidylinositol 3-kinase (Ceponis et al., *J Biol Chem,* 275(37): 29132-7 (2000)) compensated for the absence of Stat6 at day 30-44 after the conidia challenge. Furthermore, Th2-mediated inflammatory disease progressed in the absence of Stat6 and IL-4 when the transcriptional repressor that shares DNA-binding motifs with Stats, BCL-6, was deleted from mice (Dent et al., *Proc Natl Acad Sci USA,* 95(23): 13823-8 (1998)). Thus, the ultimate development of airway disease in *A. fumigatus*-sensitized Stat6−/− mice after an *A. fumigatus* conidia challenge presumably reflects the fact that other cell signaling pathways are activated in the chronic stages of this model.

The time-dependent increases in whole lung levels of IL-4 and IL-13 in Stat6−/− mice relative to Stat6+/+ mice appeared to correlate with the advent of airway hyperresponsiveness and peribronchial fibrosis in Stat6−/− mice. T cells were presumably the source of IL-4 and IL-13 since increased levels of both cytokines correlated with an increased accumulation of lymphocytes in the airways of Stat6−/− mice at days 30-44 after the conidia challenge. The present studies investigated whether the targeting of IL-13-responsive cells with IL13-PE, a chimeric protein consisting of IL-13 and *Pseudomonas* exotoxin, would reverse the Stat6-independent features of the chronic asthma model. Stat6−/− mice were treated daily with IL13-PE from days 38 to 44 after the conidia challenge, and airway hyperresponsiveness and peribronchial fibrosis were examined at day 44 after conidia. Administration of IL13-PE abolished the presence of T cells, eosinophils, and neutrophils in the BAL and significantly reduced the airway hyperresponsiveness to methacholine in Stat6−/− mice. However, administration of IL13-PE did not appear to have an effect on the peribronchial fibrosis manifest in Stat6−/− mice at day 44 after the conidia challenge. These data differ from previous findings that showed IL13-PE treatment from days 14 to 28 after the conidia challenge in *A. fumigatus*-sensitized CBA/J mice prevented the appearance of peribronchial fibrosis at day 28. The discrepancy between the previous findings and those from the present study may be related to the fact that IL13-PE therapy is necessary during the time of fibroblast activation and matrix deposition. It appears that the peribronchial fibrotic process is complete in Stat6−/− mice by day 38 after the conidia challenge and is consequently impervious to IL13-PE therapy. Thus, the Stat6-independent events leading to airway inflammation and hyperresponsiveness in Stat6−/− mice were dependent on the presence of lung cells that responded to IL-13.

In conclusion, while IL-4 and IL-13 have been shown to be central mediators in the development of fungus-induced asthma, the role of Stat6-mediated signaling had not been previously investigated during the course of this disease. The data presented herein demonstrate that Stat6 was absolutely required for goblet cell hyperplasia but other features of chronic fungal asthma including airway inflammation, airway hyperresponsiveness, and peribronchial fibrosis could develop in the absence of Stat6. However, all Stat6-independent events required IL-13 since the depletion of IL-13-responsive cells in the lung reversed many prominent features of chronic fungal asthma in Stat6−/− mice. The administration of IL13-PE obviates the need to target multiple signal transduction pathways involved in the Th2 responses leading to chronic fungal asthma.

Example 8

This Example sets forth the background for the studies reported in Examples 9-11.

Previous studies have shown that the granulomatous response elicited by *Schistosoma mansoni* via infection (Metwali et al., J Immunol, 157:4546-4553 (1996); Kaplan et al., J Immunol, 160:1850-1856 (1998); Chiaramonte et al., J. Clin. Invest., 104:777-785 (1999); Boros et al., Infect Immun, 67:1187-1193 (1999); Jankovic et al., J Immunol, 163:337-342 (1999); Fallon et al., J Immunol, 164:2585-2591 (2000)), after intravenous (i.v.) injection of live S. mansoni eggs (Kaplan et al., J Immunol, 160:1850-1856 (1998); Cheever et al., J Immunol, 153:753-759 (1994); Pearce et al., Int Immunol, 8:435-444 (1996); Subramanian et al., J Immunol, 158:5914-5920 (1997); Chiaramonte et al., J Immunol, 162:920-930 (1999); McKenzie et al., J Exp Med, 189:1565-1572 (1999); Townsend et al., J Exp Med, 191:1069-1076 (2000)) or after i.v. injection of S. mansoni egg-antigen coated Sephadex beads (Chensue et al., J. Immunol., 148:900-906 (1992); Ruth et al., Cytokine, 12:432-444 (2000)) is dependent on the Th2-dominant cellular events mediated by IL-4 and IL-13. These previous findings were derived from studies that employed cytokine immunoneutralization, gene-knockout technology or receptor decoy strategies designed to target IL-4, IL-13, both cytokines, or their receptors. For example, anti-IL-4 treatment markedly inhibited granuloma formation in the lungs of mice i.v. challenged with eggs (Cheever et al., J Immunol, 153:753-759 (1994)). Similarly, IL-4 knockout or deficient (−/−) mice have been observed to generate a modestly smaller granulomatous response to intravenously introduced S. mansoni eggs compared with appropriate wild-type mice (Pearce et al., Int Immunol, 8:435-444 (1996)). The specific role for IL-13 following S. mansoni infection (Chiaramonte et al., J. Clin. Invest., 104:777-785 (1999)) and pulmonary embolization of S. mansoni eggs (Chiaramonte et al., J Immunol, 162:920-930 (1999)) was elucidated using a soluble IL-13Rα2-Fc; this IL-13 inhibitor markedly attenuated granuloma development, pulmonary eosinophilia, and pathological hepatic and pulmonary fibrosis. However, the greatest attenuation of the synchronous pulmonary granulomatous response to S. mansoni eggs has been observed in signal transducer and activator of transcription (Stat)-6 deficient mice (Kaplan et al., J Immunol, 160:1850-1856 (1998)) and in IL-4/IL-13−/− mice (McKenzie et al., J Exp Med, 189:1565-1572 (1999)). Together, these previous studies highlight that IL-4 and IL-13 have redundant roles during S. mansoni-induced granuloma formation.

In the studies reported in the Examples below, the effect of an exemplar IL-13 targeted immunotoxin (IL-13-PE38QQR, hereinafter "IL13-PE") was examined during synchronous S. mansoni egg-induced pulmonary granuloma formation. The studies reported herein show that when given immediately after or as late as eight days following the i.v. injection of live S. mansoni eggs, IL13-PE treatment significantly arrested the development of the Th2-mediated pulmonary granulomatous response. Interestingly, the therapeutic effect of IL13-PE appeared to be mediated through the inhibition of IL-4, IL-13, tumor necrosis factor-α (TNF-α), and monocyte chemoattractant protein-1 (MCP-1/CCL2) generation and. a concomitant dramatic increase in IL-13 decoy receptor (i.e. IL-13Rα2) expression.

Example 9

This Example sets forth the material, methods, and procedures used in the studies discussed in Examples 10 and 11.

S. mansoni Egg Pulmonary Granuloma Model

Primary, synchronous pulmonary granulomas were induced in female, CBA/J mice (6-8 wks; Jackson Laboratories, Bar Harbor, Me.) following the i.v. injection of 3000 live, mature S. mansoni eggs. Live S. mansoni eggs were derived from Swiss-Webster mice heavily infected with S. mansoni (courtesy of Dr. Fred Lewis, Biomedical Research Laboratory, Rockville, Md.) according to previously described methods (Lukacs et al., J Exp Med, 177:1551-1559 (1993)). The primary model of Schistosoma egg-induced lung inflammation has been used extensively to characterize the synchronous pulmonary granulomatous response (Warren et al., Am J Trop Med Hyg, 19:291-304; Boros, D. L., Immunobiology, 191:441-450 (1994)) and model the evolution of the Th2 response (Lohning et al., J Immunol, 162:3882-3889).

IL-13-PE Therapy During Pulmonary Granulomatous Responses to Embolized S. mansoni Eggs Two dosing protocols were employed in the present studies. In the first protocol, groups of ten mice received 200 ng/dose of IL13-PE dissolved in 10 µl of phosphate buffered saline (PBS) containing 0.25% human serum albumin (HSA-PBS or diluent) via an intranasal bolus starting immediately after and every other day until day 8 after the S. mansoni egg challenge. Mice were then examined at days 8 and 16 after the induction of the pulmonary granulomatous response. In the second protocol, groups of five mice received 200 or 1000 ng/dose of IL13-PE, or diluent starting at day 8 and continuing every other day until day 16 after the egg challenge, at which time the pulmonary granulomatous response was examined. In both protocols, control groups received the appropriate volume of diluent alone over the same time course.

Lung Histological and Morphometric Analysis

Whole lungs from IL13-PE and control groups of mice (n=5/group) at days 8 and 16 after the S. mansoni egg challenge were fully inflated with 10% formalin, dissected and placed in fresh formalin for 24 h. Routine histological techniques were used to paraffin-embed the entire lung, and 5 µm sections of whole lung were stained with hematoxylin and eosin (H&E) or with Masson trichrome. Inflammatory infiltrates and structural alterations were examined around pulmonary granulomas containing a single egg using light microscopy at a magnification of 200×. Morphometric analysis of egg granuloma size and Masson trichrome staining was performed as previously described in detail (Hogaboam et al., Am J Pathol, 153:1861-1872 (1998)). Granuloma eosinophils were counted in high-powered fields at a magnification of 1000×. Quantitative digital analysis of Masson trichrome-stained slides was also preformed in order to determine the cross-sectional area in each granuloma that was occupied by collagen (Hogaboam et al., Am J Pathol, 153:1861-1872 (1998)).

Culture of Dispersed Lung and Spleen Cells

Whole lungs from IL13-PE and control groups of mice (n=5/group) were removed at day 8 and 16 after S. mansoni egg embolization. A portion of the right lobe and the spleen from each mouse was then processed according to methods described in detail elsewhere (Hogaboam et al., J Immunol, 159:5585-5593 (1997)). Briefly, lung and spleen were mechanically dissociated by grinding each organ over fine steel mesh, individual cells were quantified using a hemocytometer, and $2 \times 10^6$ dispersed cells were added to each well of 6-well tissue culture plates (Corning Inc., Corning, N.Y.). Triplicate wells were left unstimulated or exposed to 5 µg of purified S. mansoni egg antigen. Tissue culture plates containing dispersed lung or spleen cells were then maintained in a 37° C. incubator for 48 h, after which time cell free supernatants were removed for ELISA analysis (see below).

ELISA Analysis

Murine RANTES/CCL5, macrophage-derived chemokine (MDC/CCL22), C10 chemokine/CCL6, macrophage inflammatory protein-1 alpha (MIP-1α/CCL3), and IL-12 levels were measured in 50-µl samples from cell free supernatants using a standardized sandwich ELISA technique previously described in detail (Evanoff et al., *Immunol. Invest.*, 21:39-49 (1992)). Each ELISA was screened to ensure antibody specificity and recombinant murine cytokines, and chemokines were used to generate the standard curves from which the concentrations present in the samples were derived. The limit of ELISA detection for each cytokine was consistently above 50 pg/nil. The cytokine levels in each sample were normalized to total protein levels measured using the Bradford assay. Serum levels of total IgE, IgG1 and IgG2a in the IL13-PE treatment and control groups were analyzed using complementary capture and detection antibody pairs for IgE, IgG1 and IgG2a according to the manufacturer's directions (PharMingen, San Diego, Calif.). Duplicate sera samples were diluted to 1:100 for IgE determination and 1:1000 for determination of IgG1 and IgG2a levels. Immunoglobulin levels were then calculated from optical density readings at 492 nm, and Ig concentrations were calculated from a standard curve generated using recombinant IgE, IgG1 or IgG2a (all three standard curves ranged from 5-2000 pg/ml).

Pulmonary Fibroblast Culture

The left lung from the IL13-PE-treated and control groups (n=5/group) at days 8 and 16 after the *S. mansoni* egg challenge was prepared as previously described (Hogaboam et al., *J Immunol*, 163:2193-2201 (1999)) to obtain pure primary cultures of lung fibroblasts. In brief, the whole lung sample from each group was finely dispersed on steel mesh and the dispersed cells were then placed into 150 cm$^2$ cell culture flasks (Corning Inc., Corning, N.Y.). These cultured lung cells were serially passaged a total of 5 times to yield pure populations of lung fibroblasts (Hogaboam et al., *J Immunol*, 163:2193-2201 (1999)). The purified fibroblasts were then added to 24-well (at 1×10$^3$ cells/well) or 6-well (at 1×10$^5$ cells/well) tissue culture plates. To triplicate wells (in the 6-well plates) the following was added: medium alone, or medium+IL13-PE (0, 10, 200, or 1000 ng/ml). To other triplicate wells (in the 24-well plates) the following were added: 10 ng/ml of cytokine (IL-4, IFN-γ, IL-10, IL-12, or IL-13) for 48 h with the addition of 200 ng/ml of IL13-PE at 24 h. Fibroblast proliferation was assessed in 24-well plates via [$^3$H]thymidine incorporation (10 μCi/well) and RNA was isolated from lung fibroblasts in the 6-well tissue culture plates.

Preparation of cDNA and Reverse Transcriptase (RT)-PCR Amplification

Total RNA was prepared from the right lung samples removed from mice in the IL13-PE-treated and control groups (n=10/group) at days 8 and 16 after the egg challenge, and from the cultured pulmonary fibroblasts grown from the same groups at day 16 after the *S. mansoni* egg challenge. RNA was isolated using TRIzol® Reagent according to the manufacturer's (Life Technologies, Gibco BRL) directions. The purified RNA was subsequently reverse transcribed into cDNA utilizing a BRL reverse transcription kit and oligo (dT)12-18 primers. The amplification buffer contained 50 mM KCl, 10 mM Tris-HCl (pH 8.3, and 2.5 mM MgCl$_2$). Specific oligonucleotide primers were added (200 ng/sample) to the buffer, along with 1 μl of reverse transcribed cDNA sample. The following murine oligonucleotide primers (5'-3' sequences) were used for RT-PCR analysis:

```
IL-4 receptor α sense -
CCGCACTTCCACGTGTGA,           (SEQ ID NO:9)

IL-4 receptor α antisense -
CTGAAGTAACAGAACAGGC;          (SEQ ID NO:10)

IL-13 receptor α1 sense -
GAATTTGAGCGTCTCTGTCGAA,       (SEQ ID NO:11)

IL-13 receptor α1 antisense -
GGTTATGCCAAATGCACTTGAG;       (SEQ ID NO:12)

IL-13 receptor α2 sense -
ATGGCTTTTGTGCATATCAGAT,       (SEQ ID NO:13)

IL-13 receptor α2 antisense -
CAGGTGTGCTCCATTTCATTCT;       (SEQ ID NO:14)

Procollagen I sense -
TCGTGACCGTGACCTTGCG,          (SEQ ID NO:15)

Procollagen I antisense -
GAGGCACAGACGGCTGAGTAG;        (SEQ ID NO:16)

Procollagen III sense-
AGCCACCTTGGTCAGTCCTA,         (SEQ ID NO:17)

Procollagen III antisense-
TTCCTCCCACTCCAGACTTG.         (SEQ ID NO:18)
```

These mixtures were then first incubated for 4 min at 94° C. and amplified using the following cycling parameters: IL-4Rα:, Procollagen I, and Procollagen III cycled 38 times at 94° C. for 30 s, 55° C. for 45 s, and elongated at 72° C. for 60 s. IL-13α1R: cycled 38 times at 94° C. for 30 s, 66° C. for 60 s, and elongated at 72° C. for 60 s. IL-13α2R: cycled 38 times at 94° C. for 30 s, 66° C. for 60 s, and elongated at 72° C. for 60 s. After amplification the samples were separated on a 2% agarose gel containing 0.3 μg/ml of ethidium bromide and bands visualized and photographed using a translucent UV source.

Real-Time TAQMAN PCR Analysis.

Total RNA was isolated from right lobes of the lung and culture pulmonary fibroblast samples at days 0, 8, and 16 after the *S. mansoni* egg challenge as described above. A total of 0.5 μg of total RNA was reverse transcribed to yield cDNA, and IL-13Rα2, IL-13, IFN-γ, TNF-α, IL-5, MCP-1/CCL2, and MIP-1α gene expression was analyzed by real-time quantitative RT-PCR procedure using an ABI PRISM 7700 Sequence Detection System (Applied Biosystems, Foster City, Calif.). GAPDH was analyzed as an internal control. All primers and probes were purchased from Applied Biosystems. Gene expression was normalized to GAPDH before the fold change in gene expression was calculated. The fold increases in IL-4, IL-13 or IL-13Rα2 gene expression were calculated via the comparison of gene expression of these cytokines and cytokine receptor during the granulomatous response to that detected before the i.v. injection of eggs (i.e. T=0). All mRNA levels prior to egg embolization were assigned an arbitrary value of 1.

Statistical Analysis

All results are expressed as mean±standard error of the mean (SE). A one-way ANOVA and a Dunnett's Multiple Comparisons Test or a Students T test were used to reveal statistical differences between the control group and the IL13-PE treatment groups prior to and at day 8 and 16 after the *S. mansoni* egg challenge; P<0.05 was considered statistically significant.

Example 10

This Example sets forth the results of the studies regarding the *S. mansoni* egg model.

IL-13-PE Therapy Arrested *S. mansoni* Egg-Induced Pulmonary Granuloma Formation.

After treatment according to Protocol 1, pulmonary granulomas in IL13-PE-treated mice were significantly ($P<0.01$) smaller at day 8 (the final day of the 200 ng/dose-IL13-PE treatment) and ($P<0.001$) at day 16 compared with control-treated mice at the same times after the S. mansoni egg challenge. Mice treated with IL13-PE according to Protocol 2 also exhibited significantly ($P<0.01$) smaller granulomas, but this effect was only observed in the group of S. mansoni egg-challenged mice that received 1000 ng/dose of IL13-PE every other day from day 8 to day 16. Thus, administration of IL13-PE markedly arrested the development of pulmonary granulomas around S. mansoni ova in naïve mice. Unless otherwise noted, the data provided below was obtained from mice examined in Protocol 1.

IL-13-PE Therapy Significantly Increased Whole Lung Gene Expression of IL-13R 2.

RT-PCR analysis revealed that the expression of both receptors IL-4R$\alpha$ and IL-13R$\alpha$1 was constitutively present in whole lung samples from naïve mice. Following S. mansoni egg embolization, IL-4R$\alpha$ and IL-13R$\alpha$1 gene expression was increased at days 8 and 16 in the PBS control groups. In contrast, gene expression for both receptors was markedly inhibited at days 8 and 16 after egg challenge in the IL13-PE-treated groups. Because we found that RT-PCR analysis was not sufficiently sensitive enough to detect IL-13R$\alpha$2 expression in whole lung samples, quantitative TAQMAN PCR analysis was used to examine temporal changes in this decoy receptor for IL-13. Whole lung expression of IL-13R$\alpha$2 was not altered in the control group during the course of the S. mansoni egg challenge in the control group. Conversely, IL-13R$\alpha$2 gene expression was increased at day 8 and statistically significantly increased at day 16 when compared to the control group at the same time after the egg embolization. Taken together, these data indicate that IL13-PE targeted cells expressing receptors that recognize IL-4 and IL-13 while concomitantly increasing the pulmonary expression of the IL-13 decoy receptor.

Administration of IL-13-PE Did Not Significantly Reduce Circulating Levels of IgE, IgG1 or IgG2a.

Serum levels of total IgE, IgG1 and IgG2a are summarized in Table A. When administered according to Protocol 1, IL13-PE treatment from day 0 to day 8 after S. mansoni egg embolization did not significantly affect circulating levels of IgE, IgG1 and IgG2a. Serum levels of IgG1 were significantly increased at day 16 after egg embolization in the IL13-PE-treated group compared with the control group at the same time. Thus, these data suggested that IL13-PE did not specifically target Ig producing cells during S. mansoni egg challenge.

Administration of IL-13-PE Significantly Reduced the Presence of Eosinophils and Collagen in Pulmonary Granulomas.

S. mansoni egg granulomas are composed of a number of immune and non-immune cells including eosinophils, macrophages, lymphocytes, neutrophils, mast cells and fibroblasts (Metwali et al., J Immunol, 157:4546-4553 (1996)). Given the strong Th2-driven response invoked by the S. mansoni egg, eosinophils typically comprise between 50-70% of the cells present in the circumoval granulomas (Chiaramonte et al., J Immunol, 162:920-930 (1999)). The average pulmonary granuloma size was markedly reduced at both times after the egg challenge in the IL13-PE-treatment groups. However, despite the reduced size of granulomas at day 8 in the IL13-PE-treated group, eosinophils were prominent around S. mansoni eggs at this time. Quantification of eosinophils around pulmonary granulomas confirmed that similar numbers of eosinophils were present in both groups at day 8, despite the significant differences in the size of the granulomas. The diminution of granuloma size in the IL13-PE-treated groups appeared to be due to the marked absence of mononuclear cells in these lesions. However, significantly fewer eosinophils were detected in pulmonary granulomas from the IL13-PE treatment group at day 16 after the S. mansoni ova challenge. Specifically, only 3 of 15 granulomas examined in the IL13-PE-treated group contained eosinophils.

In the present study, the peribronchial distribution of extracellular matrix and fibroblasts, revealed by the Masson trichrome stain, was pronounced in the granulomas of the control groups at days 8 and 16 after the S. mansoni egg challenge. In contrast, Masson trichrome staining appeared to be much less prominent in granulomas in the IL13-PE treatment groups at both time points after the egg challenge. This observation was confirmed by RT-PCR in which the levels of procollagen I mRNA expression were significantly lower in the IL13-PE treatment groups at days 8 and 16 after the egg challenge. It was also noted that the relative involvement of total collagen deposition in the cross-sectional area of pulmonary egg granulomas in IL13-PE-treated mice was significantly reduced at day 8 but not day 16 after the egg challenge. It is important to note again that the granulomas in the both IL13-PE-treated groups were significantly smaller than those measured in the appropriate control groups. Taken together, these data indicate that targeting lung cells that recognize IL-4 and IL-13 significantly reduced the degree of peribronchial fibrosis associated with S. mansoni egg-induced pulmonary granulomas.

IL-13-PE Therapy Prevented the Significant Increase in Whole Lung Gene Expression of IL-13 and IL-4 Following S. mansoni Egg Challenge.

We next examined whether the IL13-PE treatment employed in Protocol 1 affected the gene expression of IL-13, IL-4, and IFN-$\gamma$ in whole lung samples at days 0, 8, and 16 after S. mansoni egg challenge. At day 8 after the egg challenge, IL-13 and IL-4 gene expression were increased 70- and 125-fold, respectively, in the control group. In contrast, whole lung gene expression of both Th2 cytokines was markedly lower in the IL13-PE-treated group at this time. A similar profile was noted at day 16 after the egg challenge where IL-4 and IL-13 gene expression was significantly increased above levels measured at day 0 while IL13-PE treated lungs did not exhibit this significant increase. Since IL-4/IL-13-/- mice exhibit a marked increase in IFN-$\gamma$ levels during intrapulmonary S. mansoni egg challenge (McKenzie et al., J Exp Med, 189:1565-1572 (1999)), we determined whether a similar shift in IFN-$\gamma$ levels occurred in IL13-PE-treated mice. Significantly ($P=0.0329$) less whole lung IFN-$\gamma$ gene expression was observed in the IL13-PE-treated group compared with the control group at day 8 after the egg challenge. At day 16, both groups exhibited similar gene expression for IFN-$\gamma$. These data showed that IL13-PE targeted cells that generated IL-13 and IL-4, but this same treatment also negatively affected IFN-$\gamma$ expressing cells in the lung during S. mansoni egg challenge.

IL-13-PE Therapy Prevented the Significant Increase in Whole Lung Gene Expression of TNF- and MCP-1/CCL2 Following S. mansoni Egg Challenge.

TNF-, IL-5, MCP-1/CCL2, and MIP-1/CCL3 gene expression were examined in whole lung samples. TNF-$\alpha$ and MCP-1/CCL2 gene expression was significantly increased in whole lung samples in the control group at day 8 compared with corresponding gene expression at day 0. Similar significant increases in TNF-$\alpha$ and MCP-1/CCL2 were not detected in IL13-PE-treated mice at either day 8 or 16 after the egg challenge. In addition, elevations in gene expression for IL-5 and MIP-1α/CCL3 were detected in the control groups at both days after the egg challenge, but these increases were not statistically different from gene expression measured at day 0. Whole lung gene expression for these two mediators was also lower in the IL13-PE treated groups at days 8 and 16 after *S. mansoni* egg challenge. These data indicate that the IL13-PE treatment also targeted cells with the capacity to generate cytokines and chemokines that have been previously shown to contribute to the granulomatous response to *S. mansoni* eggs (Boros, D. L., *Immunobiology*, 191:441-450 (1994); Matsukawa et al., *Microsc Res Tech*, 53:298-306 (2001)).

IL-13-PE Therapy Significantly Reduced *S. mansoni* Antigen-Induced Chemokine Synthesis by Cells Cultured from Whole Lung Samples.

A number of previous studies have shown that the granulomatous response to *S. mansoni* eggs and antigens requires the concerted actions of chemotactic cytokines or chemokines (Lukacs et al., *Chem Immunol*, 72:102-120 (1999)). These experiments addressed whether IL13-PE targeted cells in the lung that could respond to *S. mansoni* egg antigen and subsequently generate chemokines. The incubation of dispersed lung cells from control mice at day 8 after egg challenge with *S. mansoni* egg antigen resulted in a significant elevation in RANTES/CCL5, MDC/CCL22, C10/CCL6, and MIP-1α/CCL6 in cell free supernatants compared with supernatants from similarly challenged and equivalent numbers ($2 \times 10^6$ cells/well) of dispersed lung cells from naïve mice (i.e. day 0). Two million *S. mansoni* egg antigen-challenged lung cells from IL13-PE-treated mice at day 8 after egg challenge did not exhibit similar increases in chemokine generation, and C10/CCL6 and MIP-1α/CCL3 levels were actually significantly decreased compared with *S. mansoni* egg antigen-challenged lung cells from naïve mice. These data suggested that IL13-PE targeted *S. mansoni* egg antigen-responsive cells typically associated with this pulmonary granulomatous response.

IL-13-PE Significantly Increased IL-12 Production by Cells Cultured from Whole Lung and Spleen Samples.

Previous studies have shown that IL-12 is a potent inhibitor of the granulomatous and Th2 responses evoked by *S. mansoni* (Wynn et al., *J Exp Med*, 179:1551-1561 (1994); Wynn et al., *Nature*, 376:594-596 (1995); Boros et al., *Infect Immun*, 67:1187-1193 (1999); Hoffmann et al., *J Immunol*, 161:4201-4210 (1998); Mountford et al., *Immunology*, 97:588-594 (1999)). The effect of IL13-PE on IL-12 synthesis by dispersed lung cells and spleen cells was examined. Dispersed lung cells ($2 \times 10^6$ cells/well) from the control and IL13-PE-treated groups at day 8 after the egg challenge produced significantly higher amounts of IL-12 upon *S. mansoni* egg antigen (SEA) challenge-compare with similar number of cells from; naïve mice activated in the same manner. However, it was noteworthy that unstimulated cultures of dispersed lung cells from IL13-PE-treated mice also released significantly increased amounts of IL-12 compared with naïve lung cells. The effect of IL13-PE on IL-12 synthesis appeared to be limited to the lung since no significant differences were detected among the spleen cell cultures examined. These data indicate that IL13-PE significantly altered the generation of IL-12 in the lung, and this effect may have partly accounted for the effect of this chimeric protein on the granulomatous response to *S. mansoni* eggs.

IL-13-PE Inhibits Proliferation and Procollagen III Expression in Cultured Pulmonary Fibroblasts Derived from *S. mansoni* Egg Granulomas.

The direct effect of IL13-PE on cultured pulmonary fibroblast proliferation and receptor expression was examined. Pulmonary fibroblasts were purified from whole lung samples removed from untreated mice at day 16 after the *S. mansoni* egg embolization. These cultured pulmonary fibroblasts exhibited aggressive proliferative characteristics, but the exposure of these cultured fibroblasts to 200 or 1000 ng/ml of IL13-PE significantly reduced their proliferation as determined by [$^3$H]thymidine incorporation. RT-PCR analysis of mRNA from cultured pulmonary fibroblasts after their exposure to IL13-PE revealed that this chimeric protein also significantly reduced the gene expression of procollagen III; the greatest inhibitory effect on procollagen III gene expression was observed when these cells were exposed to 1000 ng/ml of IL13-PE. Thus, these findings demonstrated that IL13-PE targeted fibroblasts and markedly inhibited the proliferative and procollagen III synthesis of these cells.

IL-13-PE Induces IL-13Rα2 Gene Expression in Cultured Pulmonary Fibroblasts Derived from *S. mansoni* Egg Granulomas.

The intriguing finding that IL13-PE treatment significantly increased IL-13Rα2 expression in whole lung samples led us to examine whether this effect was related to changes in pulmonary fibroblasts. We therefore examined the effect of IL13-PE on the proliferation of cultured lung fibroblasts and the ability of these cells to express IL-13Rα2 following their exposure to IL13-PE. Of some surprise was the finding that those fibroblasts that remained after IL13-PE exposure displayed a significant, dose-related increase in IL-13Rα2 gene expression. This increase may have been related to an effect mediated by IL-13 in this fusion protein considering that recombinant IL-13 was a potent inducer of IL-13Rα2 gene expression in pulmonary fibroblasts when IL13-PE (200 ng/ml)was present in the culture. Together, these data evidenced that IL13-PE targeted pulmonary fibroblasts (presumably accounting for the significant decrease in fibroblast proliferation) and induced IL-13Rα2 gene expression in surviving fibroblasts (presumably accounting for the marked increase in IL-13Rα2 in whole lung samples from IL13-PE-treated mice).

Example 11

This Example discusses the results set forth in Example 10.

The present studies explored the effect of an exemplar IL-13R-targeted immunotoxin, IL13-PE38QQR ("IL13-PE"), containing human IL-13 and a modified *Pseudomonas* exotoxin, on the aggressive granulomatous and Th2 responses driven by intravenously introduced *S. mansoni* eggs (Grzych et al., *J Immunol*, 146:1322-1327 (1991)). IL13-PE (Debinski et al., *J Biol Chem*, 270:16775-16780 (1995)) has been previously used to successfully target human cancer cells expressing functional IL-4 and IL-13 receptors in vitro (Murata et al., *Int J Mol Med*, 1:551-557 (1998); Debinski et al., *Clin Cancer Res*, 1:1253-1258 (1995); Husain et al., *Clin Cancer Res*, 3:151-156 (1997); Debinski et al., *Int J Cancer*, 76:547-551 (1998)) and in vivo (Husain et al., *Blood*, 95:3506-3513 (2000); Kawakami et al., *Cancer Res*, 61:6194-6200 (2001); Husain et al., *Int. J. Cancer*, 92:168-175 (2001)). Because IL13-PE targeted IL-4Rα- and IL-13Rα1-positive cells in the lungs of mice challenged with live *S. mansoni* eggs (observed in the present study), this chimeric protein provides an effective therapy for attenuating the granulomatous and Th2 responses invoked by *S. mansoni* eggs.

The data shown herein demonstrate that the intranasal administration of IL13-PE, whether given immediately after (according to Protocol 1) or at day 8 (according to Protocol 2) following *S. mansoni* egg injection, significantly reduced most of the major Th2-mediated features of this model including enhanced Th2 cytokine generation, eosinophil persistence in the granuloma, and the fibrotic response around *S. mansoni* eggs. More importantly, these Th2-associated features did not reappear upon the cessation of IL13-PE treatment suggesting that IL13-PE effectively targets the effector cells that modulate the ova-induced granulomatous response. Also of major interest was the finding that IL13-PE upregulated the expression of the decoy IL-13 receptor (IL-13Rα2) in whole lung samples and in cultured fibroblasts. These findings demonstrate that IL13-PE not only eliminates IL-13 responsive fibroblasts, it also induces IL-13Rα2 chain, which can block the effects of IL-13. Taken together these findings demonstrate that IL13-PE significantly attenuates the effects of IL-4 and IL-13 during the immune response to *S. mansoni* ova.

Considerable research attention has been directed at identifying the specific temporal roles of several inflammatory and immune mediators in the development of synchronous *S. mansoni*-induced egg granulomas in the lung. Early studies pointed to distinct roles for arachidonic acid metabolites such as prostaglandins (Chensue et al., *Am J Pathol*, 111:78-87 (1983)) and leukotrienes (Kunkel et al., *J Clin Invest*, 74:514-524 (1984)) in the pulmonary granulomatous response. More recently, attention has turned to cytokines and gene analysis revealed that the introduction of *S. mansoni* eggs into mice initiated a unique pattern of cytokine expression dominated by IFN-γ, interleukin-1beta (IL-1-β), and IL-6 at day 1; IL-2, IL-4, and IL-10 at day 3; TNF-α and IL-5 at day 6 (Wynn et al., *J Immunol*, 151:1430-1440 (1993)). When *S. mansoni* ova-challenged mice received either anti-IL-2 or anti-IL-4 antibodies, the size of the egg granulomas were significantly reduced in both groups of treated mice (Wynn et al., *J Immunol*, 151:1430-1440 (1993)). Additional studies highlighted that IL-1-β (Chensue et al., *J Immunol*, 151:3654-3662 (1993)) and TNF-α (via intercellular adhesion molecule-l) (Lukacs et al., *J Immunol*, 152:5883-5889 (1994)) both contribute to the development of *S. mansoni* egg granulomas in the lung. A number of recent studies have addressed the relative importance of the Th2 response to the pulmonary granulomatous response. These studies have revealed that Th2 cells (Wynn et al., *J Immunol*, 151:1430-1440 (1993)) and eosinophils (Rumbley et al., *J Immunol*, 162:1003-1009 (1999)), which generate IL-4, strongly promote the development of granulomas whereas natural killer cells (NK cells) presumably generating IFN-γ and IL-12 suppress this formation of this lesion (Wynn et al., *J Exp Med*, 179:1551-1561 (1994)). Further studies in cytokine gene deficient mice outlined the relative importance of individual as well as synergistic actions of these cytokines in the pulmonary granulomatous response: IL-10−/− exhibited a mixed Th1 and Th2 response with reduced granulomas; IL-4−/− mice exhibited diminished Th2 response and modest reductions in granuloma size; IL-4/IL-10−/− mice exhibited a completely defective pulmonary granuloma formation process and a Th1 cytokine response; IL-12/IL-10−/− mice exhibited an exaggerated Th2 cytokine response (Wynn et al., *J Immunol*, 159: 5014-5023 (1997)). The granulomatous and Th2 response to *S. mansoni* eggs has also been shown to be dependent on the contribution of B7-2 (a CD28/CTLA4 ligand) (Subramanian et al., *J Immunol*, 158:5914-5920 (1997)), Stat-6−/− (Kaplan et al., *J Immunol*, 160:1850-1856 (1998)) and IL-13 (Chiaramonte et al., *J Immunol*, 162:920-930 (1999)). Ultimately, it was the finding that IL-4/IL-13−/− mice fail to develop any evidence of a granulomatous or Th2 response to *S. mansoni* eggs that clearly demonstrated the unequivocal role of both Th2 cytokines in this response (McKenzie et al., *J Exp Med*, 189:1565-1572 (1999)).

Clearly, the data derived from gene knockout mice show that IL-4 and IL-13 act in concert to promote an aggressive response to *S. mansoni* eggs revealing the need to explore therapeutics that target these cytokines or the cells they activate (Kaplan et al., *J Immunol*, 160:1850-1856 (1998); McKenzie et al., *J Exp Med*, 189:1565-1572 (1999)). The recent studies by Chiaramonte et al (Chiaramonte et al., *J Immunol*, 162:920-930 (1999)) also highlighted this fact in showing that a soluble IL-13Rα2-Fc fusion protein administered by i.p. injection significantly reduced serum IgE levels and the size of egg granulomas, but this soluble IL-13 antagonist only attenuated the Th2 cytokine response, eosinophilia and the fibrotic response when it was administered to IL-4−/− mice after *S. mansoni* egg challenge. In the present study, IL13-PE treatment appeared to target IL-4R- and IL-13R-expressing cells since both IL-4Rα and IL-13Rα1 gene expression was markedly reduced in mice that received this chimeric protein. At this point the characteristics of the targeted cells are unknown, but considering that IL-4 and IL-13 gene expression were all markedly reduced at days 8 and 16 after the egg challenge it is probable that CD4+ T cells were targeted by IL13-PE. Previous studies have shown that the production of both cytokines is largely dependent upon the presence of CD4+ T cells (Chiaramonte et al., *J Immunol*, 162:920-930 (1999)). In addition, we have previously observed that IL13-PE treatment significantly reduced the numbers of CD4+ T cells in the lung during chronic fungal asthma (CMH unpublished findings). However, other cells that concurrently express IL-4 and/or IL-13 receptors, and generate these cytokines include mast cells, basophils, NK cells, B cells and monocytes (Brombacher, F., *Bioessays*, 22:646-656 (2000)). The targeting of these other cells may also explain the reduction in whole lung gene expression of TNF-α, and in chemokines such as macrophage inflammatory protein-1 alpha (MIP-1α/CCL3) and monocyte chemoattractant protein-1 (MCP-1/CCL2). The latter two chemokines contribute to the development of synchronous pulmonary granulomas after *S. mansoni* egg challenge (Lukacs et al., *Journal of Experimental Medicine*, 177:1551-1559 (1993); Chensue et al., *Am J Pathol*, 146:130-138 (1995); Gao et al., *J Exp Med*, 185:1959-1968 (1997)). Other deficiencies in chemokine generation were noted in experiments designed to assess the antigen recall of mixed cultures of lung cells. These studies showed that lung cells from day 8 (post egg challenge) lungs exposed to IL13-PE had a markedly reduced capacity to generate RANTES/CCL5, MDC/CCL22, C10/CCL6 and MIP-1α/CCL3 compared with day 8 lungs cells from the control group. The lack of chemokine generation in the IL13-PE-treated group may explain the diminished number of leukocytes that were present in the granulomas of these treated mice. Specifically, the diminished numbers of eosinophils in the granulomas of IL13-PE-treated mice may have reflected the diminished levels of major eosinophils chemoattractants such as C10/CCL6, RANTES/CCL5 and MIP-1α/CCL3 (Conti et al., *Allergy Asthma Proc*, 20:205-208 (1999)).

Because naïve Stat6−/− (Kaplan et al., *J Immunol*, 160: 1850-1856 (1998)) and IL-4/IL-13−/− (McKenzie et al., *J Exp Med*, 189:1565-1572 (1999)) mice appear to develop an SEA-specific Th1 response when intravenously challenged with *S. mansoni* eggs, we examined whether IL13-PE treatment promoted a similar Th1 response. The studies reported in the previous Examples employing IL13-PE therapy in a model of chronic fungal asthma showed that targeting IL-4 and IL-13-responsive cells resulted in significantly increased levels of IFN-γ in the lung. In the present study, examination of whole lung samples revealed that IFN-γ gene expression levels were significantly decreased (at day 8) by the IL13-PE treatment employed in Protocol 1. However, analysis of dispersed cells from whole lungs of IL13-PE treated mice at day 5 after *S. mansoni* egg challenge revealed enhanced SEA-induced IL-12 production. This finding is particularly interesting in light of the potent down-regulatory effect of IL-12 on the development of *S. mansoni* egg-induced granulomatous responses (Wynn et al., *Nature*, 376:594-596 (1995); Wynn et al., *J Immunol*, 154:4701-4709 (1995); Todt et al., *Scand J Immunol*, 52:385-392 (2000)). However, these findings are somewhat tempered by recent findings from Stat4−/− mice, which lack IL-12-mediated immune responses (Kaplan et al., *Nature*, 382:174-177 (1996)), in which pulmonary granuloma formation was modestly inhibited during *S. mansoni* infection (Kaplan et al., *J Immunol*, 160:1850-1856 (1998)). Regardless of the precise role invoked by Th1-type cytokines during *S. mansoni* egg granuloma formation, it was apparent from the present study that IL13-PE treatment did not appear to promote an aggressive Th1 cytokine response as a result of its diminution of the Th2 cytokine response.

The decrease in procollagen I gene levels in whole lung samples from IL13-PE-treated mice compared with their appropriate controls suggests that this chimeric protein targets the survival and actions of pulmonary fibroblasts. Although the fibrotic response was significantly decreased in IL13-PE-treated mice (corresponding to the significantly smaller granulomas in these mice), the fibrotic response did not appear completely inhibited by the targeting of IL-4 and IL-13 responsive lung cells with this chimeric protein. Examination of the relative contribution of collagen to the cross-sectional area of the egg granulomas confirmed that collagen remained a major component of the diminished granuloma in IL13-PE-treated mice. This finding is clearly important in light of the finding that IL-4−/− and IL-4/IL-13−/− mice develop severe liver-pathology and die following infection by *S. mansoni* and this susceptibility appeared to be related to the lack of containment of the egg antigens by a fibrotic matrix (Fallon et al., *J Immunol*, 164:2585-2591 (2000)). Thus, any successful therapy directed at IL-4 and IL-13 during a *S. mansoni* egg challenge should limit but not completely inhibit the fibrotic response; IL13-PE appears to meet this criterion in the context of a pulmonary *S. mansoni* egg challenge.

Lung fibroblasts express receptors that recognize IL-4 and IL-13 (Murata et al., *Int Immunol*, 10:1103-1110 (1998); Doucet et al., *Int Immunol*, 10:1421-1433 (1998)) and both cytokines promote the proliferation and synthetic activities of these cells. In this study, pulmonary fibroblasts cultured from day 16 lungs (i.e. day 16 after egg embolization) exhibited a baseline aggressive proliferative profile. However, IL13-PE at 200 and 1000 ng/ml effectively targeted the proliferation of these cells as evidenced by a decrease in [$^3$H]thymidine incorporation. IL13-PE also effectively inhibited the gene expression of procollagen III, a major procollagen produced by pulmonary fibroblasts during clinical pulmonary fibrosis (Weissler, J. C., *Am J Med Sci* 297:91-104 (1989)). Of particular interest was the observation that IL13-PE induced the expression of IL-13Rα2 in the surviving cells.

In conclusion, the data presented herein demonstrate the therapeutic effect of targeting IL-4R and IL-13R expressing cells with a chimeric protein comprised of human IL-13 and *Pseudomonas* exotoxin during *S. mansoni* egg-induced pulmonary granuloma formation. The exemplar immunotoxin IL13-PE effectively arrested the pulmonary granulomatous and the corresponding Th2 response adding further weight to the contention that both IL-4 and IL-13 are important targets in this model. These results also hold promise in the clinical treatment of chronic *S. mansoni* egg pathology with the goal of preventing the development of severe disease.

Table A: Serum levels of IgE, IgG1 and IgG2a at days 0, 8, and 16 after *S. mansoni* egg injection. Mice were treated with IL13-PE or diluent according to Protocol 1. Values are expressed as mean±SE; n=5 mice/group. *P≦0.05 compared with Ig levels measured at day 0.

| Ig Isotype (μg/ml) | Time after *S. mansoni* Egg Injection | | | | |
| --- | --- | --- | --- | --- | --- |
| | Day 0 | Day 8 (Control) | Day 8 (+IL13-PE) | Day 16 (Control) | Day 16 (+IL13-PE) |
| IgE | N.D. | N.D. | N.D. | 6.5 ± 0.2 | 8.3 ± 1.4 |
| IgG1 | 11.4 ± 1.8 | 21 ± 3.9 | 18.3 ± 3.7 | 16.8 ± 0.6 | 29 ± 0.6* |
| IgG2a | 34 ± 5.8 | 88.7 ± 15 | 78.2 ± 2.2 | 69.2 ± 5.1 | 90 ± 24 |

N.D.—none detected
*P ≦ 0.05 compared with serum IgG1 levels measured at day 0.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for alleviating a respiratory tract symptom of a $T_H2$-type cytokine mediated disorder in a mammal, said method comprising contacting an IL-13 receptor-expressing cell in some or all of a respiratory tract of said mammal with a chimeric molecule comprising a toxin moiety and a targeting moiety that specifically binds to an IL-13 receptor.

2. A method of claim 1, wherein said chimeric molecule is administered intranasally.

3. A method of claim 1, wherein said chimeric molecule is administered into a lung or a bronchial tree.

4. A method of claim 1, wherein the targeting moiety is selected from the group consisting of: an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor.

5. A method of claim 1, wherein the $T_H2$-type cytokine mediated disorder alleviated is an allergy, asthma, tuberculosis, parasitic infection, viral infection, bacterial infection, or fungal infection.

6. A method of claim 5, wherein the $T_H2$-type cytokine mediated disorder alleviated is asthma.

7. A method of claim 5, wherein the $T_H2$-type cytokine mediated disorder alleviated is an allergy.

8. A method of claim 6, wherein the symptom of asthma alleviated is airway hyperresponsiveness.

9. A method for alleviating a respiratory tract symptom of peribronchial fibrosis response in a mammal, said method comprising contacting an IL-13 receptor-expressing cell in some or all of a respiratory tract of said mammal with a chimeric molecule comprising a toxin moiety and a targeting moiety that specifically binds to an IL-13 receptor, thereby alleviating a symptom of peribronchial fibrosis.

10. The method of claim 9, wherein said chimeric molecule is administered intranasally.

11. The method of claim 9, wherein said chimeric molecule is administered into a bronchial tree or lung.

12. The method of claim 9, wherein said chimeric molecule is an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor, and said toxin moiety is a mutated *Pseudomonas* exotoxin A.

13. The method of claim 9, wherein said chimeric molecule is in a pharmaceutically acceptable carrier.

14. A method for alleviating a respiratory tract symptom of pulmonary fibrosis in a mammal, said method comprising contacting an IL-13 receptor-expressing cell in some or all of a respiratory tract of said mammal with a chimeric molecule comprising a toxin moiety and a targeting moiety that specifically binds to an IL-13 receptor, thereby alleviating a symptom of pulmonary fibrosis.

15. The method of claim 14, wherein said chimeric molecule is administered intranasally.

16. The method of claim 14, wherein said chimeric molecule is administered into a bronchial tree or lung.

17. The method of claim 14, wherein said targeting moiety is an anti-IL-13 receptor antibody, a fragment thereof capable of binding an IL-13 receptor, IL-13 or a fragment thereof capable of binding to an IL-13 receptor, and a mutated IL-13 or a fragment thereof capable of binding to an IL-13 receptor, and said toxin moiety is a mutated *Pseudomonas* exotoxin A.

18. The method of claim 14, wherein said chimeric molecule is in a pharmaceutically acceptable carrier.

* * * * *

UNITED STATES PATENT AND TRADEMARK OFFICE
CERTIFICATE OF CORRECTION

PATENT NO.       : 7,541,040 B2
APPLICATION NO.  : 10/497804
DATED            : June 2, 2009
INVENTOR(S)      : Raj K. Puri et al.

It is certified that error appears in the above-identified patent and that said Letters Patent is hereby corrected as shown below:

**At column 2, line 31, after the text "et al.," and concluding at Column 3, line 5 before "*Am J Respir Cell Mol Biol* 18:60" the following text should be deleted:**

"which the host processor has highest access priority to that memory section after completion of transfer of isochronous messages, but before completion of transfer of all messages.

These and other advantageous aspects of the bus system according to the invention will be described in more detail using the following figures.

FIG. 1 shows a bus system

FIG. 2 shows a sequence of time frames

FIG. 3 shows a transaction descriptor

FIG. 1 shows a USB system. The system contains a USB host 1, USB connections 17$a,b$ and USB devices 18$a,b$. The USB host 1 contains a processor 10, a bus control unit 12, a common memory 14, all connected via an internal bus 16. The bus control unit 12 contains a host controller 120, a first memory 122$a$, a second memory 122$b$, a first access control unit 124$a$ and a second access control unit 124$b$. The first and second memory 122$a,b$ are coupled to the internal bus 16 via first and second access control unit 124$a,b$ respectively, via a first access port of each of these access control units 124$a,b$.

The host controller 120 is connected to the USB connections 17$a,b$. Furthermore, the host controller 120 is connected to the internal bus 16, to a control input of the first and second access control unit 124$a,b$ and to the first and second memory 122$a,b$ via second ports of the first and second access control unit 124$a,b$. The host controller 120 has an interrupt line 15 coupled to processor 10.

In operation the system transfers messages to and from USB devices 18$a,b$ via USB connections 17$a,b$. Data from the messages is produced or consumed by processor

UNITED STATES PATENT AND TRADEMARK OFFICE
CERTIFICATE OF CORRECTION

PATENT NO.       : 7,541,040 B2
APPLICATION NO.  : 10/497804
DATED            : June 2, 2009
INVENTOR(S)      : Raj K. Puri et al.

It is certified that error appears in the above-identified patent and that said Letters Patent is hereby corrected as shown below:

10. In case data has to be sent to a USB device 18*a,b* processor 10 writes this data into one of the common memory 14 or first or second memory 122*a,b* (directly or using DMA)."

Signed and Sealed this

Twenty-seventh Day of October, 2009

David J. Kappos
*Director of the United States Patent and Trademark Office*